United States Patent
Mui et al.

(10) Patent No.: US 8,956,824 B2
(45) Date of Patent: Feb. 17, 2015

(54) METHODS FOR IDENTIFYING ALLOSTERIC MODULATORS OF SHIP POLYPEPTIDES

(75) Inventors: Alice Mui, Burnaby (CA); Christopher Ong, Vancouver (CA); Gerald Krystal, Vancouver (CA); Raymond Andersen, Vancouver (CA)

(73) Assignee: British Columbia Cancer Agency Branch, Vancouver, BC (CA)

(*) Notice: Subject to any disclaimer, the term of this patent is extended or adjusted under 35 U.S.C. 154(b) by 954 days.

(21) Appl. No.: 12/478,402

(22) Filed: Jun. 4, 2009

(65) Prior Publication Data

US 2010/0311094 A1 Dec. 9, 2010

Related U.S. Application Data

(63) Continuation of application No. PCT/CA2007/002194, filed on Dec. 4, 2007.

(60) Provisional application No. 60/868,453, filed on Dec. 4, 2006.

(51) Int. Cl.
- *C12Q 1/42* (2006.01)
- *G01N 33/53* (2006.01)
- *C07K 14/00* (2006.01)
- *A61K 39/00* (2006.01)
- *G01N 33/573* (2006.01)

(52) U.S. Cl.
CPC .............. *C12Q 1/42* (2013.01); *G01N 33/573* (2013.01); *G01N 2333/916* (2013.01)
USPC ............ 435/21; 435/7.1; 530/350; 424/198.1

(58) Field of Classification Search
None
See application file for complete search history.

(56) References Cited

U.S. PATENT DOCUMENTS

| | | |
|---|---|---|
| 4,554,101 A | 11/1985 | Hopp |
| 6,147,344 A | 11/2000 | Annis et al. |
| 6,207,861 B1 | 3/2001 | Nash et al. |
| 6,283,903 B1 | 9/2001 | Onuki et al. |
| 6,581,013 B1 | 6/2003 | Annis et al. |
| 6,691,046 B2 | 2/2004 | Tyler |
| 6,694,267 B2 | 2/2004 | Kalghatgi |
| 6,714,875 B1 | 3/2004 | Nash et al. |
| 6,721,665 B2 | 4/2004 | Birnbaum et al. |
| 6,841,532 B2 | 1/2005 | Krystal et al. |
| 2006/0223749 A1 | 10/2006 | Desponts et al. |
| 2010/0099737 A1 | 4/2010 | Krystal et al. |

FOREIGN PATENT DOCUMENTS

| | | |
|---|---|---|
| CA | 2422868 | 3/2002 |
| WO | WO 97/10252 | 3/1997 |
| WO | WO97/12039 | * 4/1997 |
| WO | WO 02/24233 | 3/2002 |
| WO | WO 03/033517 | 4/2003 |
| WO | WO 2004/032880 | 4/2004 |

OTHER PUBLICATIONS

Barber et al., "PI3Kgamma Inhibition Blocks Glomerulonephritis and Extends Lifespan in a Mouse Model of Systemic Lupus," Nat Med. 11:933-935 (2005).
Bertram et al, "Inhibition of the Phosphatidylinositol 3-Kinase Pathway Promotes Autocrine Fas-Induced Death of Phosphatase and Tensin Homologue-Deficient Prostate Cancer Cells," Cancer Res. 66:4781-4788 (2006).
Bindoli et al., Biochemical and toxicological properties of the oxidation products of catecholamines, Free Radic Biol Med. 13:391-405 (1992).
Campbell et al., "Allosteric activation of PTEN phosphatase by phosphatidylinositol 4,5-bisphosphate," J Biol Chem. 278:33617-33620 (2003).
Camps et al., "Blockade of PI3Kgamma Suppresses Joint Inflammation and Damage in Mouse Models of Rheumatoid Arthritis," Nat Med. 11:936-943 (2005).
Coggeshall, K.M., "Inhibitory signaling by B cell Fc gamma Rllb.," Curr. Opin. Immunol 10(3): 306-312 (1998). (Abstract only).
Damen et al., "The 145-kDa protein induced to associate with Shc by multiple cytokines is an inositol tetraphosphate and phosphatidylinositol 3,4,5-triphosphate 5phosphatase," Proc Natl Acad Sci USA. 93:1689-1693 (1996).
Damen et al., "Multiple Forms of the SH2-Containing Inositol Posphate, SHIP, are Generated by the C-Terminal Truncation," Blood. 92:1199-1205 (1998).
Deane et al., Phosphoinositide 3-Kinase: Diverse Roles in Immune Cell Activation,PAnnu Rev Immunol. 22:563-598 (2004).
Djouder et al., "Rac and phosphatidylinositol 3-kinase regulate the protein kinase B in Fc epsilon RI signaling in RBL 2H3 mast cells," J Immunol. 166:1627-1634 (2001).
Dowler et al., "Protein lipid overlay assay," Sci STKE. PL6 (2002).
Fan et al., "A dual PI3 kinase/mTOR inhibitor reveals emergent efficacy in glioma," Cancer Cell. 9:341-349 (2006).
Galanos et al., "Mechanisms of endotoxin shock and endotoxin hypersensitivity," Immunobiology. 187:346-356 (1993).
Henikoff et al., "Amino acid substitution matrices from protein blocks," Proc. Natl. Acad. Sci. USA. 89: 10915-10919 (1992).
Hennessy et al., "Exploiting the PI3K/AKT pathway for cancer drug discovery," Nat Rev Drug Discov. 4:988-1004 (2005).

(Continued)

*Primary Examiner* — Robert Landsman
*Assistant Examiner* — Bruce D Hissong
(74) *Attorney, Agent, or Firm* — Greenberg Traurig, LLP; Chinh H. Pham; Fang Xie

(57) ABSTRACT

This invention provides a method for identifying allosteric modulators of a SHIP polypeptide, wherein said SHIP polypeptide is contacted with a test compound, and wherein said SHIP polypeptide comprises an allosteric site selected from the group consisting of a SHIP C2 domain and a SHIP PH domain.

37 Claims, 22 Drawing Sheets

(56) References Cited

OTHER PUBLICATIONS

Huber et al., "The src homology 2-containing inositol phosphatase (SHIP) is the gatekeeper of mast cell degranulation," Proc Natl Acad Sci USA. 95:11330-11335 (1998).
Huber et al., "The role of SHIP in mast cell degranulation and IgE-induced mast cell survival," Immunol Lett. 82:17-21 (2002).
Hyun et al., "Anti-inflammatory effects of nitric oxide-releasing hydrocortisone NCX 1022, in a murine model of contact dermatitis," Br J Pharmacol. 143: 618-625 (2004).
Kalesnikoff et al., "SHIP negatively regulates IgE + antigen-induced IL-6 production in mast cells by inhibiting NF-kappa B activity," J Immunol 168: 4737-4746 (2002).
Karlin et al., "Methods for assessing the statistical significance of molecular sequence features by using general scoring schemes," Proc. Natl. Acad. Sci. USA.. 87: 2264-2268 (1990).
Kemp et al., "Anaphylaxis: a review of causes and mechanisms," J Allergy Clin Immunol. 110:341-348 (2002).
Kitaura et al., "Akt-dependent cytokine production in mast cells," J Exp Med. 192:729-740 (2000).
Knight et al., "Features of selective kinase inhibitors," Chem Biol. 12:621-637 (2005).
Knight et al., "A pharmacological map of the PI3-K family defines a role for p110alpha in insulin signaling," Cell. 125:733-747 (2006).
Krahn et al., "Two distinct waves of membrane-proximal B cell antigen receptor signaling differentially regulated by Src homology 2-containing inositol polyphosphate 5-phosphatase," J Immunol. 172: 331-339 (2004).
Lucas et al., "A Novel Spliced Form of SH-2 Containing Inositol Phosphatase is Expressed During Development," Blood. 93:1922-1933 (1999).
Luo et al., "Possible dominant-negative mutation of the SHIP gene in acute myeloid leukemia," Leukemia. 17:1-8 (2003).
Ng et al., "Non-radioactive method to measure CD45 protein tyrosine phosphatase activity isolated directly from cells," Journal of Immunological Methods, 179, pp. 177-185 (1995).
Ohashi et al., "Modulating autoimmunity pick your PI3 kinase," Nat Med. 11:924-925 (2005).
Ong et al., "Small-molecule agonists of SHEP1 inhibit the phosphoinositide 3-kinase pathway in hematopoietic cells," Blood. 110(6): 1942-1949 (2007).
Sattler et al., "BCR/ABL directly inhibits expression of SHIP, an SH2-containing polyinositol-5-phosphatase involved in the regulation of hematopoiesis," Mol Cell Biol. 19:7473-7480 (1999).
Schaletzky et al., "Phosphatidylinositol-5-phosphate activation and conserved substrate specificity of the myotubularin phosphatidylinositol 3-phosphatases," Curr Biol. 13:504-509 (2003).
Simon, J. A., "Using isoform-specific inhibitors to target lipid kinases," Cell. 125: 647-649 (2006).
Sly et al., "LPS-induced upregulation of SHIP is essential for endotoxin tolerance," Immunity 21:227-239 (2004).
Sly et al., "SHIP, SHIP2, and PTEN activities are regulated in vivo by modulation of their protein levels: SHIP is up-regulated in macrophages and mast cells by lipopolysaccharide," Exp Hematol. 31:1170-1181 (2003).
Sonderman et al., "C2 Can Do It, Too," Cell: Previews. 158-160 (2005).
Sweeney et al., "Decoding protein-protein interactions through combinatorial chemistry: sequence specificity of SHP-1, SHP-2 and SHIP SHP2 domains," Biochemistry. 44(45): 14932-14947(2005).
Tu et al., "Embryonic and Hematopoietic Stem Cells Express a Novel SH2-Containing Inositol 5 ¢-Phosphatase Isoform that Partners with the Grb-Adapter Protein," Blood. 98: 2028-2038 (2001).
Vivanco et al., "The phosphatidylinositol 3-Kinase AKT pathway in human cancer," Nat Rev Cancer. 2:489-501 (2002).
Vonakis et al., "Src homology 2 domain-containing inositol 5' phosphatase is negatively associated with histamine release to human recombinant histamine-releasing factor in human basophils," J Allergy Clin Immunol. 108:822-831 (2001).
Wolf et al., "Cloning of the Genomic Locus of Mouse SH2 Containing Inositol 5-Phosphatase (SHIP) and a Novel 110-kDa Aplice Isoform, SHIPdelta," Genomics. 69: 104-112 (2000).
Workman et al., "Drugging the PI3 kinome," Nat Biotechnol. 24:794-796 (2006).
Yang et al., "Synthesis of Pelorol and Analogues: Activators of the Inositol 5Phosphatase SHIP," Org Lett. 7: 1073-1076 (2005).
Young et al., "The Mouse Ear Inflammatory Response to Topical Arachidonic Acid," J Invest Dermatol. 82: 367-371 (1984).
International Search Report issued in International Application No. PCT/CA2007/002194 mailed on Mar. 25, 2008.
Efanov et al., "A novel glucokinase activator modulates pancreatic islet and hepatocyte function," Endocrinology 146 (9): 3696-3701 (2005).
Shou et al., "Activation of CYP3A4: Evidence for the Simultaneous Binding of Two Substrates in a Cytochrome P450 Active Site," Biochemistry. 33: 6450-6455 (1994).
European Search Report issued in European application No. 07855476.3 mailed on Feb. 5, 2010.
European Office Action issued in European application No. 07855476.3 mailed on May 10, 2010.
European Office Action issued in European application No. 07855476.3 mailed on Dec. 15, 2010.
European Office Action issued in European application No. 07855476.3 mailed on May 11, 2011.

\* cited by examiner

A

B

B

| | | | |
|---|---|---|---|
| Human | 1 | MVPCWNHGNITRSKAEELLSRTGKDGSFLVRASESISRAYALCVLYRNCVYTYRILPNED | 60 |
| | | MVP WNHGNITRSKAEELLSR GKDGSFLVRASESI RA ALCVL+RNCVYTYRILPNED | |
| Mouse | 4 | MVPGWNHGNITRSKAEELLSRAGKDGSFLVRASESIPRACALCVLFRNCVYTYRILPNED | 63 |
| Human | 61 | DKFTVQASEGVSMRFFTKLDQLIEFYKKENMGLVTHLQYPVPLEEEDTGDDPEEDTESVV | 120 |
| | | DKFTVQASEGV MRFFTKLDQLI+FYKKENMGLVTHLQYPVPLEEED D+ EEDTESV+ | |
| Mouse | 64 | DKFTVQASEGVPMRFFTKLDQLIDFYKKENMGLVTHLQYPVPLEEEDAIDEAEEDTESVM | 123 |
| Human | 121 | SPPELPPRNIPLTASSCEAKEVPFSNENPRATETSRPSLSETLFQRLQSMDTSGLPEEHL | 180 |
| | | SPPELPPRNIP++A EAK++P + ENPRA E +R SLSETLFQRLQSMDTSGLPEEHL | |
| Mouse | 124 | SPPELPPRNIPMSAGPSEAKDLPLATENPRAPEVTRLSLSETLFQRLQSMDTSGLPEEHL | 183 |
| Human | 181 | KAIQDYLSTQLAQDSEFVKTGSSSLPHLKKLTTLLCKELYGEVIRTLPSLESLQRLFDQQ | 240 |
| | | KAIQDYLSTQL DS+F+KTGSS+LPHLKKL +LLCKEL+GEVIRTLPSLESLQRLFDQQ | |
| Mouse | 184 | KAIQDYLSTQLLLDSDFLKTGSSNLPHLKKLMSLLCKELHGEVIRTLPSLESLQRLFDQQ | 243 |
| Human | 241 | LSPGLRPRPQVPGEANPINMVSKLSQLTSLLSSIEDKVKALLHEGPESPHRPSLIPPVTF | 300 |
| | | LSPGLRPRPQVPGEA+PI MV+KLSQLTSLLSSIEDKVK+LLHEG ES +R SLIPPVTF | |
| Mouse | 244 | LSPGLRPRPQVPGEASPITMVAKLSQLTSLLSSIEDKVKSLLHEGSESTNRRSLIPPVTF | 303 |
| Human | 301 | EVKAESLGIPQKMQLKVDVESGKLIIKKSKDGSEDKFYSHKKILQLIKSQKFLNKLVILV | 360 |
| | | EVK+ESLGIPQKM LKVDVESGKLI+KKSKDGSEDKFYSHKKILQLIKSQKFLNKLVILV | |
| Mouse | 304 | EVKSESLGIPQKMHLKVDVESGKLIVKKSKDGSEDKFYSHKKILQLIKSQKFLNKLVILV | 363 |
| Human | 361 | ETEKEKILRKEYVFADSKKREGFCQLLQQMKNKHSEQPEPDMITIFIGTWNMGNAPPPKK | 420 |
| | | ETEKEKILRKEYVFADSKKREGFCQLLQQMKNKHSEQPEPDMITIFIGTWNMGNAPPPKK | |
| Mouse | 364 | ETEKEKILRKEYVFADSKKREGFCQLLQQMKNKHSEQPEPDMITIFIGTWNMGNAPPPKK | 423 |
| Human | 421 | ITSWFLSKGQGKTRDDSADYIPHDIYVIGTQEDPLSEKEWLEILKHSLQEITSVTFKTVA | 480 |
| | | ITSWFLSKGQGKTRDDSADYIPHDIYVIGTQEDPL EKEWLE+L+HSLQE+TS+TFKTVA | |
| Mouse | 424 | ITSWFLSKGQGKTRDDSADYIPHDIYVIGTQEDPLGEKEWLELLRHSLQEVTSMTFKTVA | 483 |
| Human | 481 | IHTLWNIRIVVLAKPEHENRISHICTDNVKTGIANTLGNKGAVGVSFMFNGTSLGFVNSH | 540 |
| | | IHTLWNIRIVVLAKPEHENRISHICTDNVKTGIANTLGNKGAVGVSFMFNGTSLGFVNSH | |
| Mouse | 484 | IHTLWNIRIVVLAKPEHENRISHICTDNVKTGIANTLGNKGAVGVSFMFNGTSLGFVNSH | 543 |
| Human | 541 | LTSGSEKKLRRNQNYMNILRFLALGDKKLSPFNITHRFTHLFWFGDLNYRVDLPTWEAET | 600 |
| | | LTSGSEKKLRRNQNYMNILRFLALGDKKLSPFNITHRFTHLFW GDLNYRV+LPTWEAE | |
| Mouse | 544 | LTSGSEKKLRRNQNYMNILRFLALGDKKLSPFNITHRFTHLFWLGDLNYRVELPTWEAEA | 603 |
| Human | 601 | IIQKIKQQQYADLLSHDQLLTERREQKVFLHFEEEEITFAPTYRFERLTRDKYAYTKQKA | 660 |
| | | IIQKIKQQQY+DLL+HDQLL ER++QKVFLHFEEEEITFAPTYRFERLTRDKYAYTKQKA | |
| Mouse | 604 | IIQKIKQQQYSDLLAHDQLLLERKDQKVFLHFEEEEITFAPTYRFERLTRDKYAYTKQKA | 663 |
| Human | 661 | TGMKYNLPSWCDRVLWKSYPLVHVVCQSYGSTSDIMTSDHSPVFATFEAGVTSQFVSKNG | 720 |
| | | TGMKYNLPSWCDRVLWKSYPLVHVVCQSYGSTSDIMTSDHSPVFATFEAGVTSQFVSKNG | |
| Mouse | 664 | TGMKYNLPSWCDRVLWKSYPLVHVVCQSYGSTSDIMTSDHSPVFATFEAGVTSQFVSKNG | 723 |
| Human | 721 | PGTVDSQGQIEFLRCYATLKTKSQTKFYLEFHSSCLESFVKSQEGENEEGSEGELVVKFG | 780 |
| | | PGTVDSQGQIEFL CYATLKTKSQTKFYLEFHSSCLESFVKSQEGENEEGSEGELVV+FG | |
| Mouse | 724 | PGTVDSQGQIEFLACYATLKTKSQTKFYLEFHSSCLESFVKSQEGENEEGSEGELVVRFG | 783 |
| Human | 781 | ETLPKLKPIISDPEYLLDQHILISIKSSDSDESYGEGCIALRLEATETQLPIYTPLTHHG | 840 |
| | | ETLPKLKPIISDPEYLLDQHILISIKSSDSDESYGEGCIALRLE TE Q PIYTPLTHHG | |
| Mouse | 784 | ETLPKLKPIISDPEYLLDQHILISIKSSDSDESYGEGCIALRLETTEAQHPIYTPLTHHG | 843 |
| Human | 841 | ELTGHFQGEIKLQTSQGKTREKLYDFVKTERDESSGPKTLKSLTSHDPMKQWEVTSRAPP | 900 |
| | | E+TGHF+GEIKLQTSQGK REKLYDFVKTERDESSG K LK+LTSHDPM+QWE + R P | |
| Mouse | 844 | EMTGHFRGEIKLQTSQGKMREKLYDFVKTERDESSGMKCLKNLTSHDPMRQWEPSGRVPA | 903 |

FIG. 11

```
Human  901  CSGSSITEIINPNYMGVGPFGPPMPLHVKQTLSPDQQPTAWSYDQPPKDSPLGPCRGESP  960
            C  SS+ E+INPNY-G+GPFG    PLH K TLSPDQQ TAWSYDQ PKDS LGP RGE P
Mouse  904  CGVSSLNEMINPNYIGMGPFG--QPLHGKSTLSPDQQLTAWSYDQLPKDSSLGPGRGEGP  961

Human  961  PTPPGQPPISPKKFLPSTANRGLPPRTQESRPSDLGKNAGDTLPQEDLPLTKPEMFENPL  1020
            PTPP QPP+SPKKF  ST NRG  PR QE+RP DLGK   + L QEDL LTKPEMFENPL
Mouse  962  PTPPSQPPLSPKKFSSSTTNRGPCPRVQEARPGDLGK--VEALLQEDLLLTKPEMFENPL  1019

Human  1021 YGSLSSFPKPAPRKDQESPKMPRKEPPPCPEPGILSPSIVLTKAQEADRGEGPGKQV---  1077
            YGS+SSFPK   PRK+QESPKM RKEPPPCP+PGI SPSIVL KAQE +  +G   KQ
Mouse  1020 YGSVSSFPKLVPRKEQESPKMLRKEPPPCPDPGISSPSIVLPKAQEVESVKGTSKQAPVP  1079

Human  1078 ---PAPRLRSFTCSSSAEGRAAGGDKSQGKPKTPVSSQAPVPAKRPIKPSRSEINQQTPP  1134
               P PR+RSFTCSSSAEGR   GDKSQGKPK   SSQAPVP KRP+KPSRSE++QQT P
Mouse  1080 VLGPTPRIRSFTCSSSAEGRMTSDKSQGKPKASASSQAPVPVKRPVKPSRSEMSQQTTP  1139

Human  1135 TPTPRPPLPVKSPAVLHLQHSKGRDYRDNTELPHHGKHRPEEGPPGPLGRTAMQ  1188  (SEQ ID NO:
 1)                                                                       3)
            P PRPPLPVKSPAVL LQHSKGRDYRDNTELPHHGKHR    G  LGRTAMQ        (SEQ ID NO:
Mouse  1140 IPAPRPPLPVKSPAVLQLQHSKGRDYRDNTELPHHGKHR---QEEGLLGRTAMQ  1190  (SEQ ID NO:
 2)
```

```
Homo_sapiens_SHIP1          SPHRPSLIPPVTFEVKAES-------LGIPQKMQLKVDVESGKLIIKK-S 42
Pan_troglodytes_SHIP1       SPHRRSLIPPVTFEVKAES-------LGIPQKMQLKVDVESGKLIIKK-S 42
Bos_Taurus_SHIP1            SPHRRSLIPPVTFEVKAES-------LGIPQKLQLKVDVESGKLIIKK-S 42
Mus_musculus_SHIP1          STNRRSLIPPVTFEVKSES-------LGIPQKMHLKVDVESGKLIVKK-S 42
Rattus_norvegicus_SHIP1     STNRRSLIPPVTFEVKSES-------LGIPQKMHLKVDVESGKLIIKK-S 42
Monodelphis_domestica_SHIP1 STHRRSLIPPVTFEVKSES-------LGIPQKMQLKVDVESGKLIIKK-S 42
Gallus_gallus_SHIP          STHRRSLIPPVTFEVKADS-------LGIFSKIHLKVDVEMGKLIIKR-A 42
Xenopus_laevis_SHIP         VKHRRSLIPPIIFEVKADS-------IGISQKTHLKVDVETGKLIIKK-S 42
Rattus_norvegicus_SHIP2     SIRKAKTIPVQAFEVKLDVTLGDLTKIGKSQKFTLSVDVEGGRLVLLRRQ 50
Mus_musculus_SHIP2          SIRKAKTIPVQAFEVKLDVTLGDLTKIGKSQKFTLSVDVEGGRLVLLRRQ 50
Homo_sapiens_SHIP2          STRKAKTIPVQAFEVKLDVTLGDLTKIGKSQKFTLSVDVEGGRLVLLRRQ 50
Danio_rerio_SHIP2           SIRN-KVIPVQTFEVKLDVYLADLTKIGKSQKYSLSVDVEGGKLVVMKKM 49
                             .. . **    ****  :       :*  .*  *.**** *:*:: :

Homo_sapiens_SHIP1          KDGSED-KFYSHKKILQLIKSQKFLNKLVILVETEKEKILRKEYVFADSK 91
Pan_troglodytes_SHIP1       KDGSED-KFYSHKKILQLIKSQKFLNKLVILVETEKEKILRKEYVFADSK 91
Bos_Taurus_SHIP1            KDSSED-KFYTHKKILQLIKSQKFLNKLVILVETEKEKILRKEYVFADSK 91
Mus_musculus_SHIP1          KDGSED-KFYSHKKILQLIKSQKFLNKLVILVETEKEKILRKEYVFADSK 91
Rattus_norvegicus_SHIP1     RDGSED-KFYSHKKILQLIKSQKFLNKLVILVETEKEKILRKEYVFSDSK 91
Monodelphis_domestica_SHIP1 KDGPED-KFYSHKKILQLIKSQKFHNKLVIVVETEKEKTLRKEYVFADSK 91
Gallus_gallus_SHIP          KDGPED-KFYTHKKILQLIKSQKVPNKLVIMLETEKEKTQRKEYVFSDSK 91
Xenopus_laevis_SHIP         KDGPDD-KFYPSKKILQLIKSQKFPHKLVIVLETEKEKTQRKEYVFADSK 91
Rattus_norvegicus_SHIP2     RDSQEDWTTFTHDRIRQLIKSQRVQNKLGVVFEKEKDRTQRKDFIFVSAR
100
Mus_musculus_SHIP2          RDSQEDWTTFTHDRIRQLIKSQRVQNKLGVVFEKEKDRTQRKDFIFVSAR
100
Homo_sapiens_SHIP2          RDSQEDWTTFTHDRIRQLIKSQRVQNKLGVVFEKEKDRTQRKDFIFVSAR
100
Danio_rerio_SHIP2           KDAQEDWNTFTHDKIRQLIKSQRVQNKLGIVFEKEKDKSQRKDFIFASAK 99
                            :*. :*  . :.  .:*  ******:. :**  ::.*:**::  **:::* .::

Homo_sapiens_SHIP1          KREGFCQLLQQMKNKHSEQPE 112 (SEQ ID NO: 4)
Pan_troglodytes_SHIP1       KREGFCQLLQQMKNKHSEQPE 112 (SEQ ID NO: 5)
Bos_Taurus_SHIP1            KREGFCQLLQQMKNKHSEQPE 112 (SEQ ID NO: 6)
Mus_musculus_SHIP1          KREGFCQLLQQMKNKHSEQPE 112 (SEQ ID NO: 7)
Rattus_norvegicus_SHIP1     KREGFCQLLQQMKNKHSEQSE 112 (SEQ ID NO: 8)
Monodelphis_domestica_SHIP1 KREGFCQLLQQMKNKHSEQPE 112 (SEQ ID NO: 9)
Gallus_gallus_SHIP          KREGFCQLLQQMKNKHSEQPE 112 (SEQ ID NO: 10)
Xenopus_laevis_SHIP         KREGFCQLLQQMKNKHSGQSE 112 (SEQ ID NO: 11)
Rattus_norvegicus_SHIP2     KREAFCQLLQLMKNKHSKQDE 121 (SEQ ID NO: 12)
Mus_musculus_SHIP2          KREAFCQLLQLIKNRHSKQDE 121 (SEQ ID NO: 13)
Homo_sapiens_SHIP2          KREAFCQLLQLMKNKHSKQDE 121 (SEQ ID NO: 14)
Danio_rerio_SHIP2           KREAFCQLLQLMKNKHSNQDE 120 (SEQ ID NO: 15)
                            ***.******  :**:** * *
```

```
SHIP1_Mus_musculus              TFEAGVTSQFVSKNGPGT---VDSQGQIEFLACYATLKTKSQTKFYLEFH 47
SHIP1_Rattus_norvegicus         TFEAGVTSQFVSKNGPGA---VDSQGQIEFLACYATLKTKSQTKFYLELH 47
SHIP1_homo_sapiens              TFEAGVTSQFVSKNGPGT---VDSQGQIEFLRCYATLKTKSQTKFYLEFH 47
SHIP1_Pan_troglodytes           TFEAGVTSQFVSKNGPGT---VDSQGQIEFLRCYATLKTKSQTKFYLEFH 47
SHIP1_Bos_Taurus                TFEAGVTSQFVSKNGPGT---TDSQGQIEFLGCYATLKTKSQTKFYLEFH 47
SHIP1_Monodelphis_domestica     TFEVGVTSQFVSKNGPGN---VDSQGQIEFLNCYATLKTKSQTKFYLEFH 47
SHIP_Gallus_gallus              TFEVGVTSQFVSKNDSKY---MNTQGEIEFLHCFATLKTKSQTKFYIEFH 47
SHIP_Xenopus_laevis             TFQVGVTSQFVSKNNPGDSGDLEAQGHIELMNCKATLYTKSHTKFYIEFH 50
SHIP2_Rattus_norvegicus         TFEVGVTSQFISKKGLSK---TSDQAYIEFESIEAIVKTASRTKFFIEFY 47
SHIP2_Mus_musculus              TFEVGVTSQFISKKGLSK---TSDQAYIEFESIEAIVKTASRTKFFIEFY 47
SHIP2_Homo_sapiens              TFEVGVTSQFISKKGLSK---TSDQAYIEFESIEAIVKTASRTKFFIEFY 47
SHIP2_Danio_rerio               TFEVGVTSQFVSKKGLPK---SSEQAYIEFENIEAIVKTASRTKFFIEFY 47
                                **:.******:**:.            ,  *. **:      *  : * *:***::*::

SHIP1_Mus_musculus              SSCLESFVKSQEGENEEG-SEGELVVRFGE-TLPKLKPIISDPEYLLDQH 95
SHIP1_Rattus_norvegicus         SSCLESFVKSQEGENEEG-DEGELVVRFGE-TLPKLKPIISDPEYLLDQH 95
SHIP1_homo_sapiens              SSCLESFVKSQEGENEEG-SEGELVVKFGE-TLPKLKPIISDPEYLLDQH 95
SHIP1_Pan_troglodytes           SSCLESFVKSQEGENEEG-SEGELVVKFGE-TLPKLKPIISDPEYLLDQH 95
SHIP1_Bos_Taurus                SSCLESFVKSQEGENEEG-SEGELVVKFGE-TLPKLKPIISDPEYLLDQH 95
SHIP1_Monodelphis_domestica     SSCLESFVKSQEGENEEG-TEGELVVKFAD-DLPKLTPIISDPEYLLDQH 95
SHIP_Gallus_gallus              SSCLESFVKSQEGENEDG-SEGELVVKFVD-ALPKLTPIISDPEYLLDQH 95
SHIP_Xenopus_laevis             SPCLENMVKSSEAEDQEG-NNGTLVVKFG--VLPKLTPIISDLEYLLDQH 97
SHIP2_Rattus_norvegicus         STCLEEYKKSFENDAQSSDNINFLKVQWSSRQLPTLKPILADIEYLQDQH 97
SHIP2_Mus_musculus              STCLEEYKKSFENDAQSSDNINFLKVQWSSRQLPTLKPILADIEYLQDQH 97
SHIP2_Homo_sapiens              STCLEEYKKSFENDAQSSDNINFLKVQWSSRQLPTLKPILADIEYLQDQH 97
SHIP2_Danio_rerio               STCLEEFKKSYENDTQSSDNVNFLRVGWSSKQLTTLKPILSDIEYLQDQH 97
                                *.***.  ** *  :..    .  * *:       *..*.**:.* ***  ***

SHIP1_Mus_musculus              ILISIKSSDSDESYGEGCIALRLETTEAQHPIYTPLTHHGEMTGHFRGEI
145
SHIP1_Rattus_norvegicus         ILISIKSSDSDESYGEGCIALRLETTESQLPIYTPLTHHGEMTGHFRGEI
145
SHIP1_homo_sapiens              ILISIKSSDSDESYGEGCIALRLEATETQLPIYTPLTHHGELTGHFQGEI
145
SHIP1_Pan_troglodytes           ILISIKSSDSDESYGEGCIALRLEATETQLPIYTPLTHHGELTGHFQGEI
145
SHIP1_Bos_Taurus                ILISIKSSDSDESYGEGCIALRLEATETQLPIYTPLTHHGEMTGHFRGNI
145
SHIP1_Monodelphis_domestica     ILISIKSSDSDESYGEGCIALRSEAIESLVPIYTALTHHGEMMGHFRGEI
145
SHIP_Gallus_gallus              ILISIKSSDSDESYGEGCIALRIEATESLVPIHTVLTHHGEKTGVFQGEI
145
SHIP_Xenopus_laevis             LLICIKSSDTDESYGEGCIALRKEDTEQQFPFCTILTHHGEETGLFCGEI
147
SHIP2_Rattus_norvegicus         LLLTVKSMDGYESYGECVVALKSMIGSTAQQFLTFLSHRGEETGNIRGSM
147
SHIP2_Mus_musculus              LLLTVKSMDGYESYGECVVALKSMIGSTAQQFLTFLSHRGEETGNIRGSM
147
SHIP2_Homo_sapiens              LLLTVKSMDGYESYGECVVALKSMIGSTAQQFLTFLSHRGEETGNIRGSM
147
SHIP2_Danio_rerio               LLLTVKSLDGYESYGECVLALKSMIGSTAQQFHTYLSHRGEETGNIRGSM
147
                                :*: :** *  ***** :**:          : * *:*:**   *  : *.:

SHIP1_Mus_musculus              KLQTSQGKM-- 154 (SEQ ID NO: 16)
SHIP1_Rattus_norvegicus         KLQTSEGKM-- 154 (SEQ ID NO: 17)
SHIP1_homo_sapiens              KLQTSQGKT-- 154 (SEQ ID NO: 18)
SHIP1_Pan_troglodytes           KLQTSQGKT-- 154 (SEQ ID NO: 19)
SHIP1_Bos_Taurus                KLQTSQGKM-- 154 (SEQ ID NO: 20)
SHIP1_Monodelphis_domestica     KLQTSQGKK-- 154 (SEQ ID NO: 21)
SHIP_Gallus_gallus              KLQTSQGKQ-- 154 (SEQ ID NO: 22)
SHIP_Xenopus_laevis             CLPASGGKQ-- 156 (SEQ ID NO: 23)
SHIP2_Rattus_norvegicus         KVRVPTERLGT 158 (SEQ ID NO: 24)
SHIP2_Mus_musculus              KVRVPTERLGT 158 (SEQ ID NO: 25)
SHIP2_Homo_sapiens              KVRVPTERLGT 158 (SEQ ID NO: 26)
SHIP2_Danio_rerio               RVRVPSERMGT 158 (SEQ ID NO: 27)
                                :  ..    :
```

METHODS FOR IDENTIFYING ALLOSTERIC MODULATORS OF SHIP POLYPEPTIDES

RELATED APPLICATION(S)

This application is a continuation of International Application PCT/CA2007/002194, with an international filing date of Dec. 4, 2007 and claims the benefit of International Application No. PCT/CA2007/002194, filed Dec. 4, 2007, and claims the benefit of U.S. provisional application no. 60/868,453, filed on Dec. 4, 2006, the entirety of all these applications are hereby incorporated herein by reference.

FIELD OF INVENTION

The invention provides methods of identifying modulators of a SHIP polypeptide. More specifically, the invention provides methods of identifying allosteric modulators of a SHIP polypeptide.

BACKGROUND OF THE INVENTION

The phosphatidylinositol (PI) 3-kinase (PI3K) pathway plays a central role in regulating many biological processes, including survival and proliferation, through the generation of the potent second messenger, PI-3,4,5-$P_3$ (PIP3). This phospholipid is present at low levels in the plasma membrane of unstimulated cells but is rapidly synthesized from phosphatidylinositol-4,5-bisphosphate (PI-4,5-$P_2$) by PI3K in response to a diverse array of extracellular stimuli. This transiently generated PIP3 initiates a cascade of downstream signaling pathways and attracts pleckstrin homology (PH) domain-containing proteins, such as Akt (also known as protein kinase B (PKB)), that regulate cellular activation, proliferation or survival, depending on the cell type and stimulus. Activation of the PI3K/Akt pathway has been linked with resistance to chemotherapeutic drugs and to radiation, and its down regulation via PI3K inhibitors lowers the resistance of tumour cell lines to various types of therapy.

Cellular levels of PIP3 are normally tightly regulated by both PI3K and the lipid phosphatases SHIP, SHIP2, and PTEN. The importance of lipid phosphatases to cellular homeostasis is underscored by the loss of activity or expression of these enzymes in human inflammatory diseases and in cancer. For example, to ensure that activation of the PI3K pathway is appropriately suppressed/terminated, the ubiquitously expressed tumour suppressor PTEN hydrolyzes PIP3 to PI-4,5-$P_2$ while the hemopoietic restricted SH2-containing inositol-5'-phosphatase 1 (SHIP1), stem cell SHIP (sSHIP) (which is transcribed from a promoter between exons 5 and 6 of the SHIP gene and is expressed in embryonic stem (ES) cells and co-expressed, albeit at low levels, with SHIP1 in HSCs), and the more widely expressed SHIP2, break it down to PI-3,4-$P_2$. Within non-hemopoietic cells, PTEN and SHIP2 appear to be the key enzymes that keep PIP3 levels suppressed while in hemopoietic cells, SHIP1 is the central player. SHIP1 (also known as SHIP), has been implicated as a negative regulator of proliferation/survival, differentiation and end cell activation in hemopoietic cells by translocating to membranes following extracellular stimulation and hydrolysation of PIP3 to PI-3,4-$P_2$.

SUMMARY OF THE INVENTION

The invention provides, in part, assays for identifying allosteric modulators of SHIP.

In one aspect, the invention provides a method of identifying an allosteric modulator of a SHIP polypeptide, the method comprising: providing a SHIP polypeptide, or fragment or variant thereof, comprising an allosteric site selected from a SHIP C2 domain or a SHIP PH domain; contacting the polypeptide with a test compound; determining whether the test compound specifically binds the SHIP polypeptide; and determining whether the test compound specifically binds the allosteric site, wherein the test compound is an allosteric modulator of a SHIP polypeptide if the test compound specifically binds the allosteric site.

In alternative embodiments, the SHIP polypeptide comprises a C2 domain (e.g., one or more of SEQ ID NOs: 16-34) and a PH domain (e.g., one or more of SEQ ID NOs: 4-15, 35, 36).

In alternative embodiments, the SHIP polypeptide sequence comprises SEQ ID NOs: 1, 2, 50 or 51. In alternative embodiments, the SHIP polypeptide is selected from the group consisting of SHIP1, SHIP2, and sSHIP.

In alternative embodiments, the SHIP polypeptide sequence is catalytically inactive. In alternative embodiments, the allosteric modulator is an activator of the SHIP polypeptide. In alternative embodiments, the allosteric modulator is an inhibitor of the SHIP polypeptide. In alternative embodiments, the allosteric modulator is selected from one or more of the group consisting of an antibody, a peptide, a protein, an oligonucleotide, and a small molecule.

In alternative embodiments, the method further comprises determining whether the test compound modulates the activity of the SHIP polypeptide. In alternative embodiments, the activity of the SHIP polypeptide comprises modulation of PIP3 levels, binding of Shc, or hydrolysis of a natural substrate.

In alternative embodiments, the method further comprises providing a control compound and determining whether the test compound modulates the activity of the SHIP polypeptide relative to the control compound. The control compound may be one or more of AQX-016A or AQX-MN100.

In alternative embodiments, the method further comprises determining whether the test compound specifically binds a SHIP polypeptide lacking an allosteric site, wherein the test compound is an allosteric modulator of a SHIP polypeptide if the test compound does not specifically bind the SHIP polypeptide lacking an allosteric site.

In another aspect, the invention provides a method of identifying an allosteric modulator of a SHIP polypeptide, the method comprising: providing a SHIP polypeptide comprising an allosteric site, wherein the allosteric site is selected from a SHIP C2 domain or a SHIP PH domain; contacting the SHIP polypeptide with a test compound; and determining whether the test compound allosterically modulates the activity or levels of the SHIP polypeptide, wherein the test compound is an allosteric modulator of a SHIP polypeptide if the test compound allosterically modulates the activity or levels of the SHIP polypeptide.

In alternative embodiments, the method further comprises providing a control compound and determining whether the test compound allosterically modulates the activity or levels of the SHIP polypeptide relative to the control compound. In alternative embodiments, the C2 domain comprises one or more of SEQ ID NOs: 16-34. In alternative embodiments, the PH domain comprises one or more of SEQ ID NOs: 4-15, 35, 36. In alternative embodiments, the SHIP polypeptide sequence comprises SEQ ID NOs: 1, 2, 50 or 51. In alternative embodiments, the SHIP polypeptide sequence is catalytically inactive.

In alternative embodiments, allosteric modulator is an activator of the SHIP polypeptide. In alternative embodiments, the allosteric modulator is an inhibitor of the SHIP polypeptide. In alternative embodiments, the allosteric modulator is selected from one or more of the group consisting of an antibody, a peptide, a protein, an oligonucleotide, and a small molecule. In alternative embodiments, the SHIP polypeptide is selected from the group consisting of SHIP1, SHIP2, and sSHIP. In alternative embodiments, the activity of the SHIP polypeptide comprises modulation of PIPS levels, binding of Shc, or hydrolysis of a natural substrate.

In alternative embodiments, the method further comprises providing a control compound and determining whether the test compound modulates the activity of the SHIP polypeptide relative to the control compound. In alternative embodiments, the control compound is one or more of AQX-016A or AQX-MN100.

In another aspect, the invention provides a method of identifying an allosteric modulator of a SHIP polypeptide, the method comprising: providing a SHIP polypeptide comprising an allosteric site, wherein the allosteric site is selected from a SHIP C2 domain or a SHIP PH domain; contacting the SHIP polypeptide with a test compound; contacting the SHIP polypeptide with a control compound that binds the allosteric site or allosterically modulates the activity of the SHIP polypeptide; and determining whether the test compound interferes with binding of the control compound to the allosteric site, or interferes with the allosteric modulation of the activity or levels of the SHIP polypeptide by the control compound, wherein the test compound is an allosteric modulator of a SHIP polypeptide if the test compound interferes with the binding of or allosteric modulation by the control compound.

In alternative embodiments, the control compound is AQX-016A or AQX-MN100.

This summary of the invention does not necessarily describe all features of the invention.

BRIEF DESCRIPTION OF THE DRAWINGS

These and other features of the invention will become more apparent from the following description in which reference is made to the appended drawings wherein.

Figure 6:
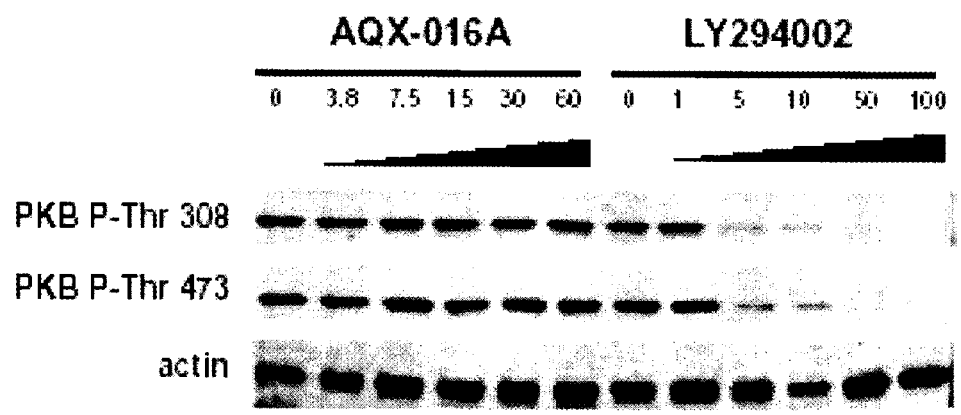

FIG. 6 shows that LY294002 but not AQX-016A inhibits PKB phosphorylation in LnCAP cells. The non-hemopoietic, prostate cancer LnCAP cell line was treated with AQX-016A or LY294002 for 30 min and cell lysates analyzed for phospho-PKB-Thr 308 or phospho-PKB 473 as described in the Examples. AQX-016A (Molecular Weight 328.24) concentration is indicated in µM.

Figure 7:
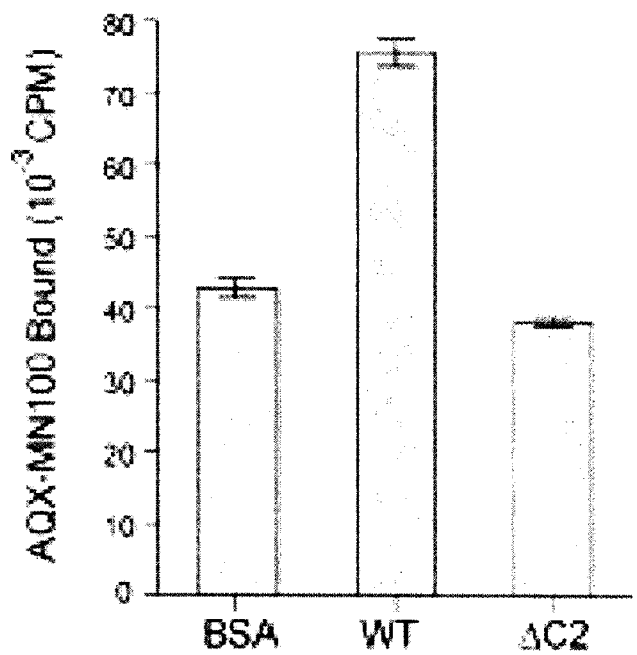

FIG. 7 shows that wild-type but not C2 domain-deleted SHIP1 enzyme binds AQX-MN100. Copper chelate (His-Tag) YSi SPA Scintillation Beads coated with either wild-type (WT) or C2 domain deleted (ΔC2) SHIP1 enzyme in the presence of 0.25% BSA as described in the Examples were aliquoted into 96 well plates. 5 µCi of [3H]-AQX-MN100 (42 Ci/mmol) was then added and the mixture incubated with shaking at 23° C. in the dark. The amount of [3H]-AQX-MN100 interacting with the protein coated beads was quantified on a plate scintillation counter.

Figure 8:
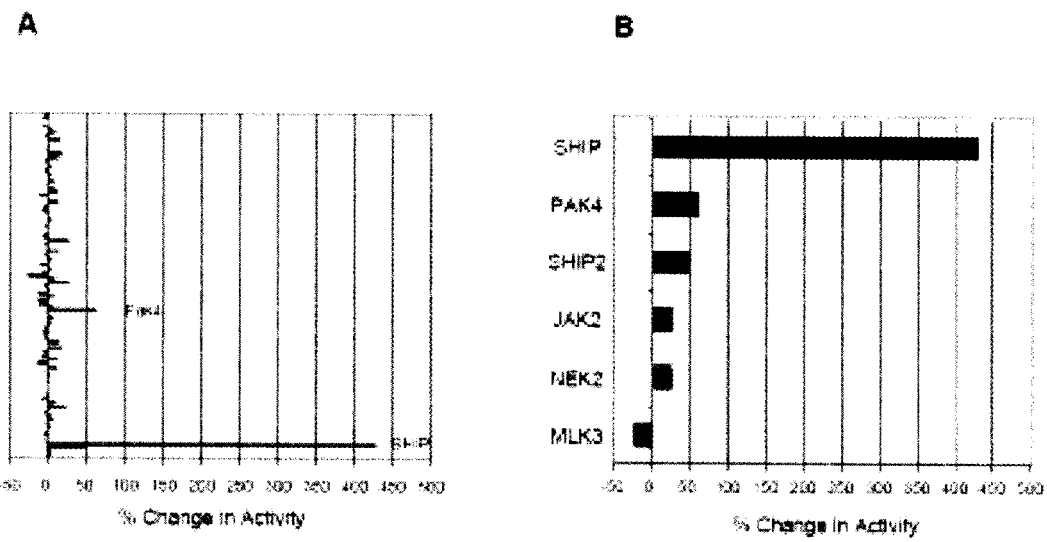

FIGS. 8A-B show that AQX-MN100 selectively enhances SHIP enzyme activity. (A) Compound profiling activity was undertaken using 100 protein kinase and phosphatase targets by SignalChem (Richmond, BC, Canada) against compound AQX-MN100 (2 µM final concentration). Protein kinase assays were performed in the presence of 50 µM ATP at 30° C. for 15 min. Protein phosphatase activities were determined using pNPP as substrate and were also performed at 37° C. for 15 min. The activity of the enzymes in the presence of AQX-MN100 was compared to that in the vehicle control and expressed as a % change in activity relative to that observed in the vehicle control. Changes in activity of <25% were not considered significant. Enzymes affected by AQX-MN100 are plotted in an expanded graph in B.

Figure 9:
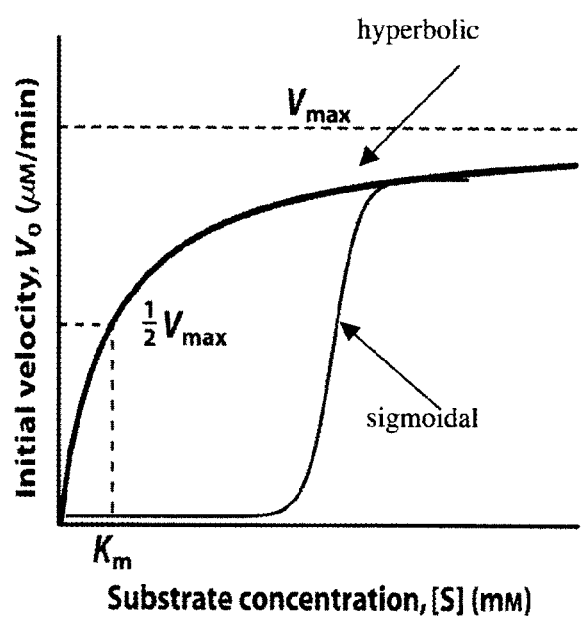

FIG. 9 shows that SHIP1 enzyme exhibits end-product allosteric regulation. Non-allosterically regulated enzymes exhibit Michaelis-Menton hyperbolic enzyme reaction rate kinetics. Enzymes which are allosterically activated by their end-product (positive feedback) exhibit sigmoidal shaped enzyme kinetic curves.

Figure 10:
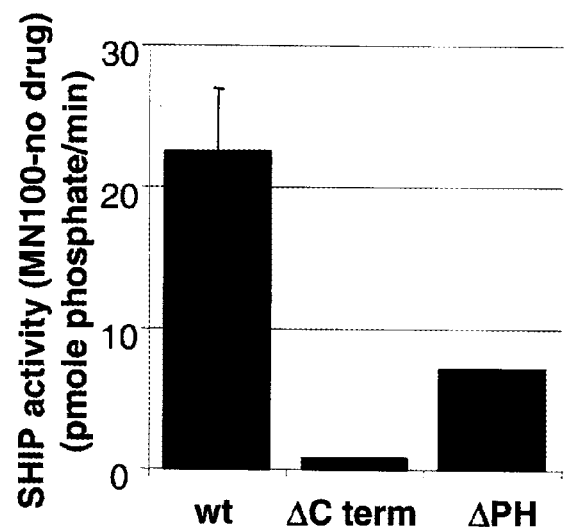

FIG. 10 shows that deletion of the SHIP1 C-terminus abrogates the ability of SHIP1 to be activated by AQX-MN100. SHIP1 phosphatase activity is expressed as the difference between the activity seen in the presence of AQX-MN100 minus the activity in the presence of vehicle (EtOH). Deletion of the PH domain attenuates but does not prevent activation by AQX-MN100.

FIGS. 11A-F shows SHIP protein domains and alignments thereof. (A) Schematic diagram showing SHIP1 deletion constructs. (B) Amino acid sequence alignment of human (Genbank identifier U57650; SEQ ID NO: 1) and mouse (Genbank identifier U39203; SEQ ID NO: 2) SHIP1, showing the PH domain (underlined), the phosphatase domain (in italics), and the C2 domain (in bold). The consensus sequence (SEQ ID NO: 3) is indicated in the centre. The alignment was performed using ClustalW (Score=1873 bits (4852), Expect=0.0, Identities=1040/1194 (87%), Positives=1092/1194 (91%), Gaps=13/1194 (1%)). (C) Amino acid alignment of SHIP1 and SHIP2 PH domains from various species (SEQ ID NOs: 4-15). (D) Amino acid alignment of SHIP1 and SHIP2 C2 domains from various species (SEQ ID NOs: 16-27). Phylograms of SHIP1 and SHIP2 PH domains (E) and C2 domains (F) from various species.

Figure 12:
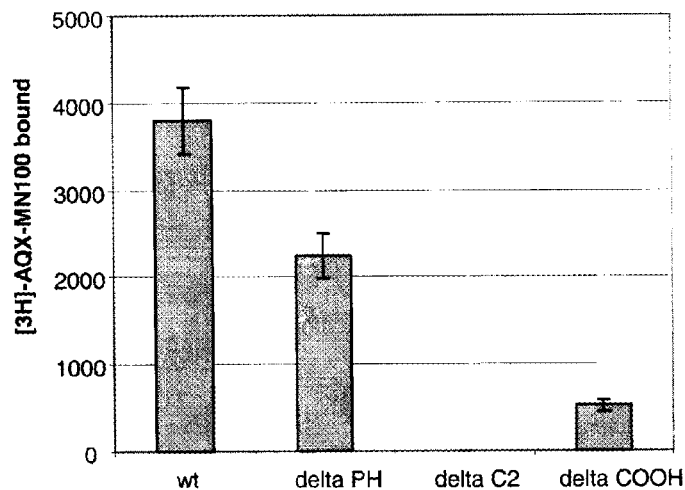

FIG. 12 shows that SHIP1 protein requires the C2 domain to bind to AQX-MN100. Purified, recombinant SHIP1 enzyme and domain deletion mutant constructs as shown in the top panel were bound to SPA (scintillation proximity assay) beads. [3H]-AQX-MN100 was added and the amount of SHIP1 bound AQX-MN100 was quantified by scintillation counting. Data are expressed as the net cpm observed (cpm bound to control (albumin) coated beads subtracted).

Figure 13:
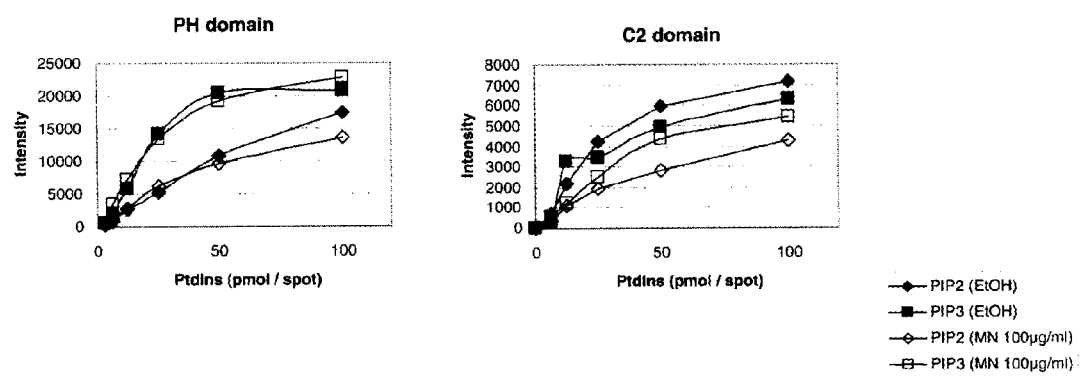

FIG. 13 shows that the binding of the C2 but not the PH domain to phosphatidylinositol lipid (PIP2 and PIP3) is inhibited by AQX-MN100. Purified, recombinant HIS6 tagged SHIP1 PH or C2 domains were incubated with AQX-MN100 or vehicle (EtOH) control for 30 min prior to incubation with membrane strips spotted with a dilution series of PIP2 or PIP3. The amount of PH or C2 domain bound to each spot was visualized with anti-HIS6 antibody followed by Alexa 660 conjugated secondary antibody, quantified on a Li-Cor Odyssey scanner and expressed in arbitrary units. The PH domain binds PIP3>PIP2, whereas the C2 domain binds PIP2>PIP3. Only the C2 binding to PIP2/PIP3 could be inhibited by AQX-MN100.

Figure 14:
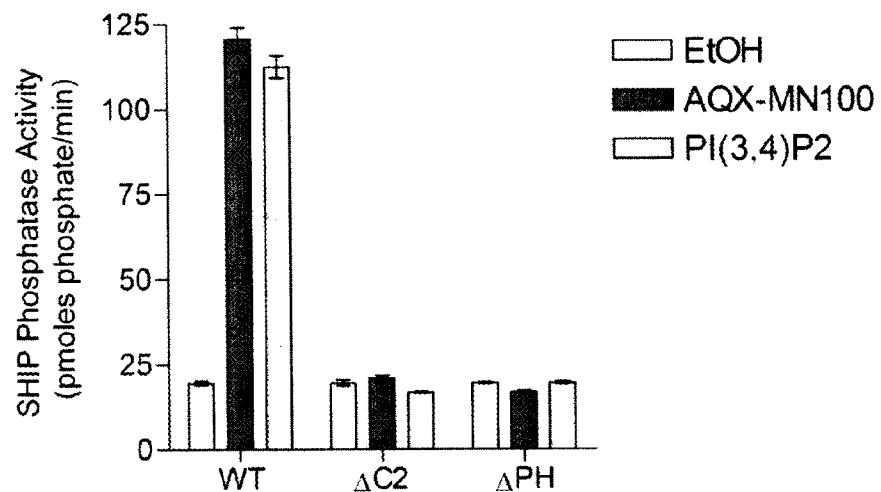
Figure 14:
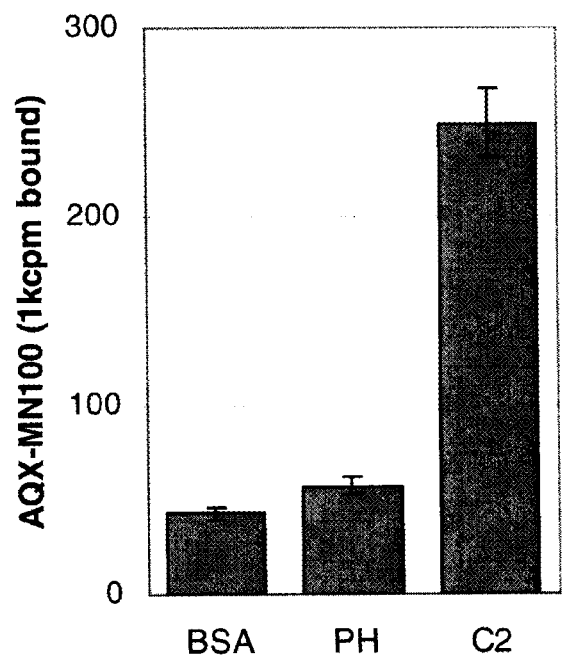

FIGS. 14A-B show that the PH domain is required for allosteric activation, but does not directly bind to the PH domain. (A) Deletion of the PH domain abrogates ability of SHIP to be activated by PI(3,4)$P_2$ and AQX-MN100. (B) The C2 but not the PH domain binds AQX-MN100.

DETAILED DESCRIPTION

The invention provides, in part, methods for identifying modulators of lipid phosphatases and provides a new paradigm for inhibition of PI3K-dependent processes. Small molecule agonists and antagonists of the hemopoietic cell-specific SHIP enzyme, for example, represent potential therapeutics for treatment of immune/hemopoietic disorders in which the PI3K pathway is dysregulated. Because of their unique target and mechanism of action, these compounds may also be powerful synergistic agents in combination with current therapies.

SH2-Containing Inositol-5'-Phosphatase (SHIP) Molecules

SH2-containing inositol-5'-phosphatases (or SH2-containing phosphatidylinositol phosphatase), referred to herein as "SHIP molecules," are phosphatases that selectively remove the phosphate from the 5-position of the inositol ring in phosphoinositol-containing lipids.

The first such phosphatase identified, referred to herein as "SHIP1," is restricted to hemopoietic cells and is a 145 kDa protein that becomes both tyrosine phosphorylated and associated with the adaptor protein, Shc, after extracellular stimulation of hemopoietic cells. SHIP1 contains an N-terminal Src homology 2 (SH2) domain that binds preferentially to the amino acid sequence pY(Y/D)X(L/I/V), a centrally located 5'-phosphatase that selectively hydrolyses PI-3,4,5-$P_3$ and Ins(1,3,4,5)$P_4$ (IP$_4$) in vitro, two NPXY amino acid sequences that, when phosphorylated, bind the phosphotyrosine binding (PTB) domains of Shc, Dok1 and Dok2 and a proline-rich C-terminus that binds a subset of Src homology 3 (SH3)-containing proteins. SHIP1 includes alternatively spliced forms (24, 25) and C-terminal truncations (26). In alternative embodiments, SHIP1 includes, without limitation, alternative splice forms and truncations. In alternative embodiments, SHIP1 includes, without limitation, the SHIP1 sequences disclosed in U.S. Pat. No. 6,238,903 (issued to Krystal, May 29, 2001), PCT publication WO 97/10252 (naming Rohrschneider and Lioubin as inventors and published Mar. 20, 1997), or as described in GenBank Accession Nos. U57650 (human; SEQ ID NO:1), U39203 (mouse; SEQ ID NO: 2), U51742 (mouse), U52044 (mouse), NMJ301017915 (human), AAB49680 (human), NPJD4696 (updated Q9ES52, mouse) or other SHIP1 mouse and human sequences, or other SHIP1 sequences from other species such as chimpanzee, oppossum, cow, rat, chicken, frog, etc.

A 104 kDa protein termed "stem cell SHIP" or "sSHIP" is only expressed in stem cells and HSCs (27), but not in HPCs. sSHIP is generated by transcription from a promoter within the intron between exons 5 and 6 of the SHIP1 gene and is neither tyrosine phosphorylated nor associated with Shc following stimulation, but binds constitutively to Grb2. In alternative embodiments, sSHIP includes, without limitation, the sSHIP sequences as described in GenBank Accession Nos. AF184912 (mouse; SEQ ID NO: 51), or other sSHIP sequences from various species.

SHIP2, which is a more widely expressed 150 kDa protein that also becomes tyrosine phosphorylated and associated with Shc in response to extracellular stimulation, exists, like SHIP and sSHIP, in lower-molecular-mass forms and specifically hydrolyses the 5'-phosphate from PI-3,4,5-$P_3$ and $IP_4$ in vitro. In alternative embodiments, SHIP2 includes, without limitation, the SHIP2 sequences as described in GenBank Accession Nos. AB011439 (rat), AB025794 (rat), AF162781 (mouse), NP_001558.2 (human; SEQ ID NO: 50), DQ272661 (zebrafish), DQ272662 (zebrafish), or other SHIP2 sequences from various species.

In alternative embodiments, SHIP molecules include fragments or domains of SHIP1, SHIP2, sSHIP or other SHIP molecules. For example, SHIP molecules include C2 and/or PH domains of SHIP1 from various species, as well as corresponding domains from other SHIP molecules (e.g. SHIP2). It is to be noted that C2 and/or PH domains of sSHIP are identical to those of SHIP1.

In alternative embodiments, a C2 domain of SHIP1 includes amino acid residues 715 to 856 of human SHIP1, as set forth in GenBank Accession No. U57650 (SEQ ID NO: 1), although the precise boundaries of the N-terminal and C-terminal regions of the C2 domain may vary. For example, a C2 domain of SHIP1 may include amino acid residues 706 to 873 of human SHIP1, or may include amino acid residues 706 to 859 of human SHIP1, or may include amino acid residues 706 to 856 of human SHIP1, or may include amino acid residues 715 to 873 of human SHIP1, or may include amino acid residues 715 to 859 of human SHIP1, or may include amino acid residues 715 to 856 of human SHIP1, as set forth in GenBank Accession No. U57650 (SEQ ID NO: 1).

In alternative embodiments, a C2 domain of SHIP1 includes amino acid residues 725 to 863 of murine SHIP1, as set forth in GenBank Accession No. NP_034696.

In alternative embodiments, a C2 domain of SHIM includes one or more of the following sequences:

```
                                            (SEQ ID NO: 28)
PGTVDSQGQIEFLACYATLKTKSQTKFYLEFHSSCLESFVKSQEGENEEG

SEGELVVRFGETLPKLKPIISDPEYLLDQHILISIKSSDSDESYGEGCIA

LRLETTEAQHPIYTPLTHHGEMTGHFRGEIKLQTSQGKM;

(SEQ ID NO: 29)
PGTVDSQGQIEFLRCYATLKTKSQTKFYLEFHSSCLESFVKSQEGENEE

GSEGELVVKFGETLPKLKPIISDPEYLLDQHILISIKSSDSDESYGEGCI

ALRLEATETQLPIYTPLTHHGELTGHFQGEIKLQTSQGKT;

(SEQ ID NO: 30)
VTSQFVSKNGPGTVDSQGQIEFLACYATLKTKSQTKFYLEFHSSCLESFV

KSQEGENEEGSEGELVVRFGETLPKLKPIISDPEYLLDQHILISIKSSDS

DESYGEGCIALRLETTEAQHPIYTPLTHHGEMTGHFRGEIKLQTSQGKM;

(SEQ ID NO: 31)
TFEAGVTSQFVSKNGPGTVDSQGQIEFLRCYATLKTKSQTKFYLEFHSSC

LESFVKSQEGENEEGSEGELVVKFGETLPKLKPIISDPEYLLDQHILISI

KSSDSDESYGEGCIALRLEATETQLPIYTPLTHHGELTGHFQGEIKLQTS

Q;

(SEQ ID NO: 32)
VTSQFVSKNGPGTVDSQGQIEFLACYATLKTKSQTKFYLEFHSSCLESFV

KSQEGENEEGSEGELVVRFGETLPKLKPIISDPEYLLDQHILISIKSSDS

DESYGEGCIALRLETTEAQHPIYTPLTHHGEMTGHFRGEIKLQTSQ;

(SEQ ID NO: 33)
TFEAGVTSQFVSKNGPGTVDSQGQIEFLRCYATLKTKSQTKFYLEFHSSC

LESFVKSQEGENEEGSEGELVVKFGETLPKLKPIISDPEYLLDQHILISI

KSSDSDESYGEGCIALRLEATETQLPIYTPLTHHGELTGHFQGEIKLQTS

QGKM;
or
                                            (SEQ ID NO: 34)
TFEAGVTSQFVSKNGPGTVDSQGQIEFLRCYATLKTKSQTKFYLEFHSSC

LESFVKSQEGENEEGSEGELVVKFGETLPKLKPIISDPEYLLDQHLLISI

KSSDSDESYGEGCIALRLEATETQLPIYTPLTHHGELTGHFQGEIKLQTS

QGKTREKLYDFVKTERDE.
```

Figure 11:
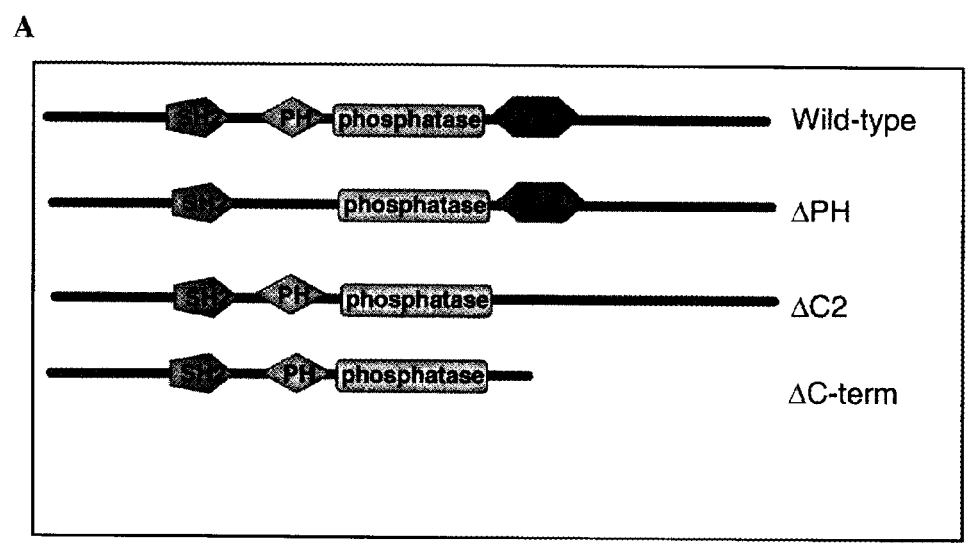
Figure 11:
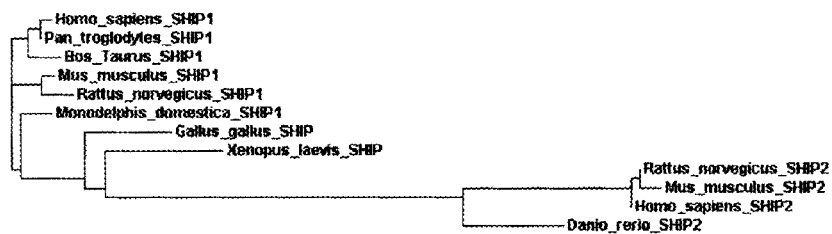
Figure 11:
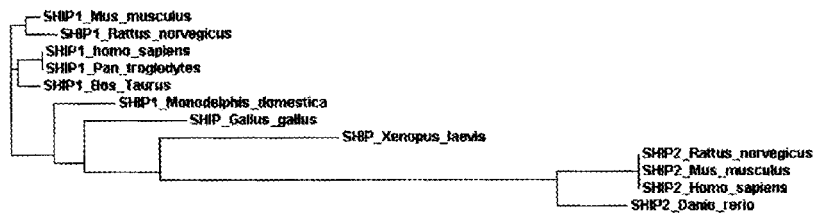

Additional exemplary SHIP1 C2 domains are set forth in FIG. 11D, which shows alignments of SHIP1 C2 domains from various species (SEQ ID NOs: 16-27). The accession numbers used for the sequence alignments were as follows:

| | |
|---|---|
| Bos_Taurus_SHIP1 | NP_001095352.1 |
| Gallus_gallus_SHIP1 | XP_001231652.1 |
| Homo_sapiens_SHIP1 | NP_001017915 |
| Monodelphis_domestica_SHIP1 | XP_001373539.1 |
| Mus_musculus_SHIP1 | NP_034696.1 |
| Pan_troglodytes_SHIP1 | XP_526066.2 |
| Rattus_norvegicus_SHIP1 | NP_062184.1 |
| Xenopus_laevis_SHIP1 | NP_001083668.1 |
| Danio_rerio_SHIP2 | NP_001034893.1 |
| Gallus_gallus_SHIP2 | XP_001231652.1 |
| Homo_sapiens_SHIP2 | NP_001558.2 |
| Mus_musculus_SHIP2 | NP_034697.1 |
| Rattus_norvegicus_SHIP2 | NP_075233.1 |
| Xenopus_laevis_SHIP2 | NP_001083668.1 |

In alternative embodiments, a PH domain of SHIP1 includes amino acid residues 291 to 402 of murine SHIP, as set forth in GenBank Accession No. U39203 (SEQ ID NO: 2), or amino acid residues 288 to 399 of human SHIP, as set forth in GenBank Accession No. U57650 (SEQ ID NO: 1), although the precise boundaries of the N-terminal and C-terminal regions of the PH domain may vary.

In alternative embodiments, a PH domain of SHIP1 includes the following amino acids:

```
                                            (SEQ ID NO: 35)
STNRRSLIPPVTPLVKSESLGIPQKMHLKVDVESGKLIVKKSKDGSEDKF

YSHKKILQLIKSQKFLNKLVILVETEKEKILRKEYVFADSKKREGFCQLL

QQMKNKHSEQPE
or
```

(SEQ ID NO: 36)
SPHRPSLIPPVTFEVKAESLGIPQKMQLKVDVESGKLIIKKSKDGSEDKF

YSHKKILQLIKSQKFLNKLVILVETEKEKILRKEYVFADSKKREGFCQLL

QQMKNKHSEQPE.

Additional exemplary PH domains are set forth in FIG. 11C, which shows alignments of PH domains from various species (SEQ ID NOs: 4-15). The accession numbers used for the sequence alignments were the same as those used for alignment of C2 domains.

In alternative embodiments, a SHIP molecule including a C2 domain or a PH domain, or both, may also include one or more additional sequences. In particular embodiments, the SHIP molecule includes additional SHIP sequence flanking one or more of the amino terminal or carboxy terminal end of a C2 or PH domain described herein. In alternative embodiments, the additional sequence may include a SHIP phosphatase domain, for example, DMITIFIGTWNMGNAPPP-KKITSWFLSKGQGKTRDDSADYIPHDIYVIGTQEDP
LSEKEWLEILKHSLQEITSVTFK-
TVAIHTLWNIRIVVLAKPEHENRISHICTDNV
KTGIANTLGNKGAVGVSFMFNGTSLG-
FVNSHLTSGSEKKLRRNQNYMNILRF LALGDKKL-
SPFNITHRFTHLFWFGDL-
NYRVDLPTWEAETIIQKIKQQQYADLLS
HDQLLTERREQKVFLHFEEEEITFAP-
TYRFERLTRDKYAYTKQKATGMKYNLP SWCDRVL-
WKSYPLVHVVCQSYGSTSDIMTSDHSPV-
FATBEAGVT (SEQ ID NO: 37). In alternative embodiments, the SHIP phosphatase domain may be inactivated for example by mutation or deletion or other inactivation of the catalytic cysteine. In particular embodiments, a SHIP molecule comprises a C2 domain or a PH domain, but does not include an active phosphatase domain. In further embodiments, the SHIP molecule comprises both a C2 domain and a PH domain, but does not include an active phosphatase domain.

In alternative embodiments, the additional sequence may be positioned at the N-terminal or the C-terminal end of the C2 or the PH domain. If both the C2 and the PH domains are present, the additional sequence may be positioned between the C2 and the PH domain. In alternative embodiments, the additional sequences may include naturally occurring regions flanking the C2 or PH domains. In alternative embodiments, a SHIP molecule may include one or more C2 domains or one or more PH domains; the C2 or PH domains may be identical or may be different. The SHIP molecule or the PH and/or the C2 domains can be covalently linked, for example, by polymerisation or conjugation, to form homopolymers or heteropolymers.

In alternative embodiments, the additional sequence may include a linker sequence. Spacers and linkers, typically composed of small neutral molecules, such as amino acids that are uncharged under physiological conditions (e.g., glycine), can be used. Linkages can be achieved in a number of ways. For example, cysteine residues can be added at the peptide termini, and multiple peptides can be covalently bonded by controlled oxidation. Alternatively, heterobifunctional agents, such as disulfide/amide forming agents or thioether/amide forming agents can be used.

It is well known in the art that some modifications and changes can be made in the structure of a polypeptide without substantially altering the biological function of that peptide, to obtain a biologically equivalent polypeptide. Accordingly, in alternative embodiments, SHIP molecules include, without limitation, SHIP C2 and/or PH domains as described herein and combinations thereof, as well as analogues and variants thereof. Such SHIP molecules can be prepared by, for example, replacing, deleting, or inserting an amino acid residue at any position of a C2 or PH domain peptide, as described herein, with other conservative amino acid residues, i.e., residues having similar physical, biological, or chemical properties, and screening for SHIP activity.

As used herein, the term "conserved amino acid substitution" or "conservative amino acid substitution" refers to the substitution of one amino acid for another at a given location in a peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, etc., and such substitutions may be assayed for their effect on the function of the peptide by routine testing.

As used herein, the term "amino acids" means those L-amino acids commonly found in naturally occurring proteins, D-amino acids and such amino acids when they have been modified. Accordingly, amino acids of the invention may include, for example: 2-Aminoadipic acid; 3-Aminoadipic acid; beta-Alanine; beta-Aminopropionic acid; 2-Aminobutyric acid; 4-Aminobutyric acid; piperidinic acid; 6-Aminocaproic acid; 2-Aminoheptanoic acid; 2-Aminoisobutyric acid; 3-Aminoisobutyric acid; 2-Aminopimelic acid; 2,4 Diaminobutyric acid; Desmosine; 2,2'-Diaminopimelic acid; 2,3-Diaminopropionic acid; N-Ethylglycine; N-Ethylasparagine; Hydroxylysine; allo-Hydroxylysine; 3-Hydroxyproline; 4-Hydroxyproline; Isodesmosine; allo-Isoleucine; N-Methylglycine; sarcosine; N-Methylisoleucine; 6-N-methyllysine; N-Methylvaline; Norvaline; Norleucine; and Ornithine.

In some embodiments, conserved amino acid substitutions may be made where an amino acid residue is substituted for another having a similar hydrophilicity value (e.g., within a value of plus or minus 2.0, or plus or minus 1.5, or plus or minus 1.0, or plus or minus 0.5), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conservative amino acid substitutions may be made where an amino acid residue is substituted for another having a similar hydropathic index (e.g., within a value of plus or minus 2.0, or plus or minus 1.5, or plus or minus 1.0, or plus or minus 0.5). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conservative amino acid substitutions may be made using publicly available families of similarity matrices (28-34). The PAM matrix is based upon counts derived from an evolutionary model, while the Blosum matrix uses counts derived from highly conserved blocks within an alignment. A similarity score of above zero in either of the PAM or Blosum matrices may be used to make conservative amino acid substitutions.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (35). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently ($C_1$-$C_6$)alkyl, substituted ($C_1$-$C_6$)alkyl, ($C_1$-$C_6$)alkenyl, substituted ($C_1$-$C_6$)alkenyl, ($C_1$-$C_6$)alkynyl, substituted ($C_1$-$C_6$)alkynyl, ($C_5$-$C_{20}$)aryl, substituted ($C_5$-$C_{20}$)aryl, ($C_6$-$C_{26}$)alkaryl, substituted ($C_6$-$C_{26}$)alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine-3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

In some embodiments, conservative substitutions include, without limitation, the following exemplary substitutions:

| Original Residue | Substitution | Alternative Substitution |
| --- | --- | --- |
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylatin, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR—, where R is ($C_1$-$C_6$)alkyl, ($C_1$-$C_6$)alkenyl, ($C_1$-$C_6$)alkynyl, substituted ($C_1$-$C_6$)alkyl, substituted ($C_1$-$C_6$)alkenyl, or substituted ($C_1$-$C_6$)alkynyl) or isostere of an amide linkage (for example, —$CH_2NH$—, —$CH_2S$—, —$CH_2CH_2$—, —CH=CH— (cis and trans), —C(O)$CH_2$—, —CH(OH)$CH_2$—, or —$CH_2SO$—).

Peptides or peptide analogues can be synthesised by standard chemical techniques, for example, by automated synthesis using solution or solid phase synthesis methodology. Automated peptide synthesisers are commercially available and use techniques well known in the art. Peptides and peptide analogues can also be prepared using recombinant DNA technology using standard methods such as those described in, for example, Sambrook, et al. (36) or Ausubel et al. (37).

In alternative embodiments, a SHIP molecule includes sequences that are substantially identical to the C2 domain or PH domain sequences as described herein, or substantially identical to sequences encoding such C2 domain or PH domain sequences. A "substantially identical" sequence is an amino acid or nucleotide sequence that differs from a reference sequence only by one or more conservative substitutions, as discussed herein, or by one or more non-conservative substitutions, deletions, or insertions located at positions of the sequence that do not destroy the biological function of the amino acid or nucleic acid molecule. Such a sequence can be any integer from 10% to 99%, or more generally at least 10%, 20%, 30%, 40%, 50, 55% or 60%, or at least 65%, 75%, 80%, 85%, 90%, or 95%, or as much as 96%, 97%, 98%, or 99% identical when optimally aligned at the amino acid or nucleotide level to the sequence used for comparison using, for example, ClustalW. For polypeptides, the length of comparison sequences may be at least 2, 5, 10, or 15 amino acids, or at least 20, 25, or 30 amino acids. In alternate embodiments, the length of comparison sequences may be at least 35, 40, or 50 amino acids, or over 60, 80, or 100 amino acids, as appropriate. For nucleic acid molecules, the length of comparison sequences may be at least 5, 10, 15, 20, or 25 nucleotides, or at least 30, 40, or 50 nucleotides. In alternate embodiments, the length of comparison sequences may be at least 60, 70, 80, or 90 nucleotides, or over 100, 200, or 500 nucleotides. Sequence identity can be readily measured using publicly available sequence analysis software (e.g., BLAST software available from the National Library of Medicine, or as described herein). Such software matches similar sequences by assigning degrees of homology to various substitutions, deletions, substitutions, and other modifications.

Alternatively, or additionally, two nucleic acid sequences may be "substantially identical" if they hybridize under high stringency conditions. In some embodiments, high stringency conditions are, for example, conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations.) Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology, and examples of them can be found, for example, in Ausubel et al. (37), which is hereby incorporated by reference.

SHIP Modulators

SHIP modulators, e.g., allosteric modulators, include compounds that modulate SHIP enzymatic function or SHIP levels directly or indirectly by, for example, targeting of a SHIP signal transduction pathway; modulation of SHIP activation; modulation of SHIP mRNA transcription; modulation of SHIP mRNA degradation; or modulation of SHIP protein translation, stability or activity.

"Modulating" or "modulates" means changing, by either increase or decrease. The increase or decrease may be a change of any value between 10% and 90%, or of any value between 30% and 60%, or may be over 100%, when compared with a control or reference sample or compound. In alternative embodiments, the increase or decrease may over two-fold, or over five-fold, or over 10-fold, or over 100-fold, or over 300-fold, or over 500-fold or over 1000-fold, when compared with a control or reference sample or compound.

By an "allosteric modulator" is meant an agent that binds a target molecule at a site (an "allosteric site") that is different from the active or catalytic site of the target molecule and modulates the activity or expression of the target molecule, directly or indirectly. Thus, an allosteric modulator "allosterically modulates" the activity or levels of a target molecule by interaction with the target molecule at a site other than the active or catalytic site of the target molecule. In alternative embodiments, an "allosteric modulator" includes an agent that does not directly bind an allosteric site, but is capable of modulating the enzymatic activity or the levels of the target molecule. In all embodiments, an allosteric modulator does not directly bind to an active or catalytic site of a target molecule. Allosteric sites of a SHIP molecule include C2 domains and/or PH domains. In general, an allosteric modulator induces a conformational change in the target molecule that leads to, for example, disruption of the active site, disruption of binding of the natural substrate of the target molecule, or poor release of the reaction products. In some embodiments, allosteric modulators may have the advantages of specificity and selectivity for their target, and/or concentration-independent limits on activity that can significantly reduce side effects.

An allosteric modulator may be a positive allosteric modulator i.e., an allosteric activator or an allosteric agonist, or may be a negative allosteric modulator i.e., an allosteric inhibitor or an allosteric antagonist. An allosteric antagonist can, in some embodiments, bind simultaneously with a natural substrate of the target molecule and thus can selectively inhibit signals to be propagated through the target molecule. In various embodiments, an antagonist inhibits a biological or enzymatic activity, or the level of expression, of the target molecule by any value between 10% and 90%, or of any value between 30% and 60%, or may be 100%, when compared with a control or reference sample or compound. In alternative embodiments, the level of inhibition may be at least or greater than two-fold, five-fold, 10-fold, 100-fold, 300-fold, 500-fold, or 1000-fold, when compared with a negative control or a reference sample or compound, e.g., a known antagonist.

An allosteric agonist can, in some embodiments, bind simultaneously with a natural substrate of the target molecule and thus can potentiate the function of the target molecule. In various embodiments, an agonist increases or enhances a biological or enzymatic activity, or the level of expression, of a target molecule by any value between 10% and 90%, or of any value between 30% and 60%, or over 100%, when compared with a control or reference sample or compound. In alternative embodiments, the increase, enhancement, or potentiation may over two-fold, or over five-fold, or over 10-fold, or over 100-fold, or over 300-fold, or over 500-fold or over 1000-fold, when compared with a negative control or a reference sample or compound.

In certain embodiments, an allosteric SHIP modulator can bind a SHIP C2 domain or a SHIP PH domain and modulate a SHIP enzymatic or biological activity, or expression levels. In alternative embodiments, an allosteric SHIP modulator includes an agent that does not directly bind a SHIP C2 domain or a SHIP PH domain, but is capable of modulating SHIP enzymatic activity or SHIP levels. In all embodiments, an allosteric SHIP modulator does not bind to a SHIP catalytic site. An allosteric SHIP modulator may be a positive allosteric SHIP modulator i.e., an allosteric SHIP activator or an allosteric SHIP agonist, or may be a negative allosteric SHIP modulator i.e., an allosteric SHIP inhibitor or an allosteric SHIP antagonist. An allosteric SHIP antagonist can, in some embodiments, interfere with SHIP binding to its natural substrate, e.g., PIP3 or $IP_4$, and thus can selectively inhibit SHIP function or levels. An allosteric agonist can, in some embodiments, enhance SHIP binding to its natural substrate, e.g., PIP3 or $IP_4$, and thus can potentiate SHIP function or levels.

In alternative embodiments, SHIP modulators include without limitation small molecules, antibodies or fragments thereof, such as humanized anti-SHIP antibodies, peptides and peptide fragments; ribozymes; oligonucleotides, and the like.

In alternative embodiments, SHIP modulators specifically modulate SHIP1, i.e., modulate SHIP1 with a greater specificity when compared to modulation of SHIP2 or other molecules. In related embodiments, SHIP1-specific modulators do not significantly modulate the activity of SHIP2, or other molecules. In particular embodiments, a SHIP1-specific modulator targets or binds a C2 or PH domain of SHIP 1, such as the sequences set forth herein. In alternative embodiments, a SHIP 1-specific modulator does not directly bind a C2 domain or a PH domain of SHIP1 but nevertheless modulates a SHIP1 function. In alternative embodiments, when the SHIP molecule is SHIP1 or includes a SHIP1 C2 or PH domain, the SHIP modulator is not AQX-016A or AQX-MN100.

Assays for Identification of SHIP Modulators

Allosteric SHIP modulators may be identified using methods described herein or known in the art. For example, an allosteric SHIP modulator may be identified by determining whether it specifically binds to an allosteric site of a SHIP molecule, such as a C2 domain or a PH domain, or interferes with SHIP binding to other proteins, or modulates a SHIP activity, such as modulation of a SHIP enzymatic or biological activity, including any of those described herein, e.g., regulation of cellular PIP3 levels. By "specifically binds," when used in the context of binding of a SHIP polypeptide, is meant that the allosteric SHIP modulator binds to a SHIP polypeptide or fragment or variant thereof, as described herein, but does not substantially recognise and bind other molecules in a sample. In particular embodiments, when an allosteric modulator "specifically binds" a SHIP1 polypeptide, it does not substantially recognise and bind other SHIP polypeptides, e.g., does not substantially bind SHIP2 polypeptides. Such an allosteric modulator has, for example, an affinity for the SHIP polypeptide which is at least 10, 100, 1000 or 10000 times greater than the affinity of the allosteric modulator for another reference molecule, or for a SHIP2 polypeptide, in a sample. By "specifically binds," when used in the context of binding of an allosteric site, is meant that the allosteric SHIP modulator binds to an allosteric site of a SHIP polypeptide (e.g., a C2 domain or a PH domain), but does not substantially recognise and bind the active or catalytic site of the SHIP polypeptide. Such an allosteric modulator has, for example, an affinity for the allosteric site which is at least 10, 100, 1000 or 10000 times greater than the affinity of the allosteric modulator for the active or catalytic site of the SHIP polypeptide.

The allosteric site employed in such screening may be an isolated naturally occurring protein fragment, may be produced recombinantly, or may be a chemically synthesized molecule. In some embodiments, the C2 or the PH domain may each be used in isolation. In alternative embodiments, the C2 domain or the PH domain may be used in combination with each other and/or with additional sequences, such as addition SHIP sequences e.g., a SHIP phosphatase domain, or with heterologous sequences, such as a heterologous phosphatase domain or other sequence. In some embodiments, a SHIP phosphatase domain to be used may be inactivated by for example inactivation of the catalytic site.

Methods of identifying SHIP allosteric modulators may be performed in vitro or in vivo. They may also be practiced using isolated or purified SHIP polypeptides or SHIP polypeptides present within a cell, including recombinantly produced SHIP polypeptides. In addition, these methods may be practiced using binding assays to identify modulators that bind to one or more SHIP allosteric sites, or using assays of SHIP biological or enzymatic activity to identify SHIP modulators. In particular embodiments, the allosteric nature of an identified SHIP modulator is confirmed by determining the ability of the modulator to bind to an allosteric site in SHIP.

Thus, in particular embodiments, the invention provides methods of identifying an allosteric modulator of a SHIP molecule, comprising contacting a SHIP molecule with a candidate modulator and determining an amount of bound candidate modulator, and comparing this amount of bound candidate molecule to a control amount, wherein if the amount of bound candidate molecule is at least two-fold, at least three-fold, or at least five-fold greater than the control amount, the candidate molecule is confirmed to be an allosteric modulator of the SHIP molecule. In particular embodiments, the SHIP molecule is SHIP1, SHIP2, or sSHIP, or a fragment thereof. For example, in particular embodiments, the SHIP molecule comprises or consists of a SHIP PH or C2 site. In further embodiments, the SHIP molecule does not include the catalytic domain or is enzymatically inactive. In alternative embodiments, the SHIP molecule lacks an allosteric site ("a SHIP deletion mutant") e.g., lacks a C2 domain and/or a PH domain, and the candidate molecule is confirmed to be an allosteric modulator of a SHIP molecule if the candidate molecule does not substantially bind the SHIP deletion mutant.

In particular embodiments, a control amount is a predetermined negative control value obtained by measuring the binding of one or more negative control compounds, which are known to not bind to a SHIP molecule, using the same binding assay and conditions used to screen candidate modulators. In other embodiments, a control amount is a negative control value obtained at the time of screening a candidate modulator, by measuring the amount of a bound negative control compound, which is known to not bind to a SHIP molecule.

In other particular embodiments, the invention provides methods of identifying an allosteric modulator of a SHIP molecule, comprising contacting a SHIP molecule with a candidate modulator, measuring a biological or enzymatic activity of the SHIP molecule, and comparing this amount of biological or enzymatic activity to a control amount, wherein if the amount in the presence of the candidate modulator is at least two-fold, at least three-fold, or at least five-fold greater than the control amount, the candidate modulator is confirmed to be an allosteric modulator of the SHIP molecule. In particular embodiments, the SHIP molecule is SHIP1, SHIP2, or sSHIP, or a fragment thereof. In additional embodiments, this method further comprises determining that the identified allosteric modulator binds to an allosteric site of a SHIP molecule.

In particular embodiments, a control amount is a predetermined control value obtained by measuring the biological activity of the SHIP molecule in the absence of any candidate or control compound, or in the presence of a control compound known to not bind SHIP or modulate SHIP activity, using the same assay and conditions used to screen candidate modulators. In other embodiments, a control amount is an amount of biological or enzymatic activity of the SHIP molecule determined in the absence of any candidate modulator or control compound, or in the presence of a control compound known to not bind to the SHIP molecule. This may be determined at the same time the candidate modulator is assayed.

In one related embodiment, the invention includes a method of identifying an allosteric modulator of a SHIP molecule by determining the amount of a biological or enzymatic activity of the SHIP molecule in the presence or absence of a candidate modulator, wherein a modulator is identified when its presence results in a significant difference in the activity, e.g., at least two-fold, three-fold, or five-fold greater activity, or a reduction in activity to less than 90%, less than 80%, less than 70%, less than 60%, less than 50%, less than 40%, less than 30%, less than 20%, or less than 10% activity, when compared to the activity in the absence of the modulator.

Suitable screening assays include cell-free binding assays in which a SHIP molecule, or C2 or PH domain thereof, is incubated with a test compound which may bear a detectable label (e.g., a radioactive or fluorescent label). Following incubation, the SHIP molecule, or C2 or PH domain thereof, free or bound to test compound, can be separated from unbound test compound using any of a variety of techniques. For example, the SHIP molecule, or C2 or PH domain thereof, can be bound to a solid support (e.g., a plate or a column) and washed free of unbound test compound. The amount of test compound bound to SHIP molecule, or C2 or PH domain thereof, is then determined, for example, using a technique appropriate for detecting the label used (e.g., liquid scintillation counting and gamma counting in the case of a radiolabeled test compound or by fluorometric analysis).

Binding assays can also take the form of cell-free competition binding assays. In such assays, a SHIP molecule, or C2 or PH domain thereof, is incubated with a compound known to interact with an allosteric site (e.g., C2 or PH domain) of a SHIP molecule, e.g., AQX-016A or AQX-MN100. The known compound may bear a detectable label (e.g., a radioactive or fluorescent label). A test compound is added to the reaction and assayed for its ability to compete with the known (labeled) compound for binding to SHIP. Free known (labeled) compound can be separated from bound known compound, and the amount of bound known compound determined to assess the ability of the test compound to compete. This assay can be formatted so as to facilitate screening of large numbers of test compounds by linking the SHIP molecule, or C2 or PH domain thereof, to a solid support so that it can be readily washed free of unbound reactants. A plastic support, for example, a plastic plate (e.g., a 96 well dish), is preferred. SHIP molecule, or C2 or PH domain thereof, suitable for use in the cell-free assays described above can be isolated from natural sources or prepared recombinantly or chemically. The SHIP molecule, or C2 or PH domain thereof, can be prepared as a fusion protein using, for example, known recombinant techniques. Exemplary fusion proteins include a GST (glutathione-S-transferase) moiety, a GFP (green fluorescent protein) moiety (useful for cellular localization studies) or a His tag (useful for affinity purification).

As indicated above, the SHIP molecule, or fusion protein, can be present linked to a solid support, including a plastic or glass plate or bead, a chromatographic resin (e.g., Sepharose), a filter or a membrane. Methods for attaching proteins to such supports are well known in the art and include direct chemical attachment and attachment via a binding pair (e.g., biotin and avidin or biotin and streptavidin). Whether free or bound to a solid support, the SHIP molecule, or C2 or PH domain thereof, can be unlabeled or can bear a detectable label (e.g., a fluorescent or radioactive label).

Cells can be engineered to express a SHIP molecule, or C2 or PH domain thereof, by introducing into a selected host an expression construct comprising a sequence encoding a SHIP molecule, or C2 or PH domain thereof, operably linked to a promoter. A variety of vectors and promoters can be used. For example, pET-24a(+) (Novagen) containing a T7 promoter is suitable for use in bacteria, likewise, pGEX-5X-1. Suitable yeast expression vectors include pYES2 (Invitron). Suitable baculovirus expression vectors include p2Bac (Invitrogen). Suitable mammalian expression vectors include pB K/CMV (Stratagene). Introduction of the construct into the host can be effected using any of a variety of standard transfection/transformation protocols (36, 37). Cells thus produced can be cultured using established culture techniques suitable for the involved host. Culture conditions can be optimized to ensure expression of the SHIP molecule, or C2 or PH domain thereof, encoding sequence. The encoding sequence can be selected so as to ensure that the expression product is secreted into the culture medium. The cell-based binding assays described herein can be carried out by adding test compound (optionaly bearing a detectable (e.g., radioactive or fluorescent) label), to medium in which the SHIP molecule expressing cells are cultured, incubating the test compound with the cells under conditions favorable to binding and then removing unbound test compound and determining the amount of test compound associated with the cells. The test compound may be obtained from for example a combinatorial chemical library, a natural products library, or a peptide library.

In one embodiment, inhibitors are identified using Automated Ligand Identification System (referred to herein as "ALIS"). See, e.g., U.S. Pat. Nos. 6,721,665, 6,714,875, 6,694,267, 6,691,046, 6,581,013, 6,207,861, and 6,147,344. ALIS is a high-throughput technique for the identification of small molecules that bind to proteins of interest (e.g., SHIP polypeptides). Small molecules found to bind tightly to a protein can then be tested for their ability to inhibit the biochemical activity of that protein or associated ion channel.

A test compound identified in one or more of the above-described assays as being capable of binding to an allosteric site of a SHIP molecule, can, potentially, allosterically modulate the SHIP molecule. To determine the specific effect of any particular test compound selected on the basis of its ability to bind an allosteric site of a SHIP molecule, assays can be conducted to determine, for example, the effect of various concentrations of the selected test compound on SHIP activity. SHIP binding affinity or modulation of SHIP activity can exhibit for example any value between between 10% and 90%, or of any value between 30% and 60%, or may be over 100%, when compared with a control or reference sample or compound. In alternative embodiments, the binding affinity or modulation may be over two-fold, or over five-fold, or over 10-fold, or over 100-fold, or over 300-fold, or over 500-fold or over 1000-fold, when compared with a known substrate or modulator of a SHIP molecule, or other reference compound. It is to be understood however that the exact level of binding affinity or modulation is not relevant, as long as the results are statistically significant, using standard statistical techniques, or the results are recognized as significant by a person skilled in the art of performing such assays.

Assays for SHIP biological or enzymatic activity include, without limitation, assays for the association of a SHIP molecule with Shc and/or hydrolyzation of a natural SHIP substrate such as PI-3,4,5-P3 and IP4. For example, a natural SHIP substrate may be reacted in the presence of a test compound under conditions which permit the hydrolysis of the substrate, the amount of hydrolysis product determined, and the amount of hydrolysis product obtained in the presence of the test compound compared with the amount obtained in the absence of the test compound to determine the affect of the test compound on SHIP activity. Conditions which permit the hydrolysis of the substrate, may be selected having regard to factors such as the nature and amounts of the substance, substrate, and the amount of SHIP or SHIP related proteins.

For example, substrate and standards for a SHIP phosphatase assay, $^{32}$P-PI3,4,5P$_3$ and $^{32}$P-PI3,4P$_2$, are prepared using standard techniques. The labelled SHIP substrate is mixed with SHIP protein for the appropriate length of time under conditions suitable for SHIP phosphatase activity. After extraction of phospholipids, the organic phase containing SHIP substrate is separated by, for example, thin-layer chromatography (TLC) and the radioactive lipids visualized by autoradiography. The identity of PI3,4,5P$_3$ and PI3,4P$_2$ is confirmed by comparison with $^{32}$P-PI3,4,5P$_3$ and $^{32}$P-PI3, 4P$_2$, prepared separately, and run on the same TLC plate. PI3,4,5P$_3$ and PI3,4P$_2$ are quantified by densitometric analysis.

Additional SHIP assays include cell or animal based assays which monitor changes in nitric oxide production from activated macrophages; IgE induced mast cell degranulation; LPS induced macrophage activation; TNF-α expression or activity. In addition, standard assays for agents which mediate inflammatory activity in living subjects may be employed. Adaptation of these assays is facilitated by the availability of SHIP 1−/− and SHIP I+/− mice and bone marrow derived macrophages. In addition, the availability of anti-SHIP antibodies facilitates use of immunoassay formats.

Exemplary assays are as follows.

In vitro testing in a SHIP enzyme assay. Test compounds are dissolved in a suitable solvent (e.g. EtOH, DMSO and others) and diluted into aqueous buffer (20 mM Tris HCl, pH 7.5 and 10 mM MgCl$_2$). SHIP enzyme assays are performed in 96-well microtitre plates with 10 ng of enzyme/well in a total volume of 25 µL of 20 mM Tris HCl, pH 7.5 and 10 mM MgCl$_2$. SHIP enzyme is incubated with test extracts (provided in solvent) or vehicle for 15 min at 23° C. before the addition of 100 inositol-1,3,4,5-tetrakisphosphate (Echelon Biosciences Inc, Salt Lake City, Utah). After 20 min at 37° C. and the amount of inorganic phosphate released is assessed by the addition of Malachite Green reagent and absorbance measurement at 650 nm.

Macrophage TNF-α production. J774.1a macrophage cells are treated with 10 µg/mL of test compound dissolved in solvent (e.g. cyclodextran) for 40 minutes prior to the addition of 100 ng/mL LPS. Culture supernatants are collected after 2 hrs and 5 hrs for TNF-α determination by ELISA.

Macrophage TNF-α NO assay. J774.1a macrophage cells are treated with 10 µg/ml of test compound dissolved in solvent for 40 minutes prior to the addition of LPS. Culture supernatants are collected after 24 hrs for determination of NO concentration using the Griess reagent. Alternatively, wild-type or SHIP 1−/− macrophage cells are activated with 1 g/mL endotoxin (LPS) in the presence or absence of test compound or DMSO carrier. The cells are incubated at 37° C., 5% CO$_2$ for 24 hours and the culture supernatant is removed for NO determination using the Griess reagent.

Stimulation of mast cells by FcεRI crosslinking. Mast cells are pre-loaded overnight in BMMC medium lacking IL-3 with 0.1 µg/ml anti-DNP IgE (SPE-7, Sigma, Oakville, Ont). For calcium flux measurements, cells are incubated with 2 µM fura 2-acetoxymethyl ester (Molecular Probes, Eugene, Oreg.) in Tyrode's buffer at 23° C. for 45 min. Cells are then washed and incubated in the presence of the test compound 30 min prior to stimulation with the indicated concentration of DNP-human serum albumin (DNP-HSA). Calcium influx is monitored by spectrofluorometry as described previously. For analysis of intracellular signaling, cells are pre-loaded with anti-DNP IgE as above, pre-treated with the test compound for 30 min at 37° C. and stimulated with 20 ng/ml DNP-HSA for 5 min. Total cell lysates are then prepared and analyzed for phospho-PKB, phospho-p38$^{MAPK}$, phospho-MAPK, Grb-2 (Cell Signalling, Mississauga, Ont) and SHIP by immunoblot analysis.

Mouse acute cutaneous anaphylaxis model. 6-8 week old CD1 mice (available, for example, from the University of British Columbia Animal Facility, Vancouver, BC) are sensitized to the hapten DNP by cutaneous application of 25 µL of 0.5% dinitrofluorobenzene (DNFB) (Sigma, Oakville, Ont) in acetone to the shaved abdomen of mice for two consecutive days. 24 hrs later, test substances (dissolved in 10 µL of 1:2 DMSO:MeOH) are painted on the right ear while the left ear receives vehicle control. 30 min after drug application, DNFB is applied to both ears to induce mast cell degranulation. A 6 mm punch is taken from the ear and immediately frozen on dry ice for subsequent determination of neutrophil myeloperoxidase (MPO) activity.

Mouse endotoxemia model. 6-8 week old C57B16 mice (available, for example, from the VCHRI Mammalian Model of Human Disease Core Facility, Vancouver, BC) are orally administered a test compound 30 min prior to an IP injection of 2 mg/kg of LPS (*E. Coli* serotype 0111:B4, Sigma, Oakville, Ont). Blood is drawn 2 hrs later for determination of plasma TNFα by ELISA.

In vitro Multiple Myeloma (MM) assay. The ability of SHIP activators to reduce tumor cell survival is assessed in MM cell lines treated with a test compound. The lines OPM1, OPM2, MM.1S and RPMI 8226 are plated at a density of $1\times10^5$ cells/mL in 200 µL of medium with various concentrations of the test compound, and viable cell numbers are determined on day 3 and day 5 by trypan blue exclusion. The lines RPMI 8226 and U266 are plated at a density of $1\times10^6$ cells/mL in 250 µL of medium with various concentrations of the test compound. At day 4, the medium of each culture is replaced by fresh medium containing the same concentration of test compound. At day 7, the viable cell number of each culture is determined by trypan blue exclusion.

MM cell lines are cultured in 96 well plates seeded with $3\times10^4$ cells suspended in 200 µL of medium along with various concentrations of test compound (and associated cyclodextran vehicle control), with LY294002 serving as a positive control in the experiments. After 24-48 hrs of culture, 1 Ci of [3H]-thymidine (GE Healthcare, Baie D'Urfe, Canada) being added for the final 8 hours. Cells are harvested and DNA associated radioactivity was measured via liquid scintillation counting using a Wallac MICROBETA™ counter (Perkin-Elmer; Boston, Mass.).

Colitis assay. The colitis assay is based on determining whether a test compound protects mice from TNBS (trinitrobenzene sulfonic acid) induced inflammation. Test compound or vehicle control is injected intraperitoneally into mice just prior to a TNBS enema administration and the colons of the mice are examined for signs of inflammation.

In vivo Multiple Myeloma (MM) assay. Mice are inoculated at two sites each with $3\times10^6$ luciferase expressing OPM2 cells suspended in 50 µL of growth medium and 50 µL of MATRIGEL™ basement membrane matrix (Becton Dickenson; Bedford, Mass.). Tumors are injected subcutaneously in the upper and lower flanks of the mice and allowed to establish for 2 weeks. After 2 weeks, a test compound or control vehicle is administered in a subcutaneous oil depot at a dose of 50 mg/kg every 3 days. Tumors are measured using bioluminescence imaging on the Xenogen IVIS™ 200. Mice received intra-peritoneal injections of 200 µL of D-luciferin at 3.75 mg/mL in sterile PBS. Mice are then anesthetized with isofluorane and imaged 15 minutes post-injection of luciferin. Quantification of tumor size is performed using the LIVING IMAGE™ software.

Therapeutic Indications

As demonstrated herein, SHIP modulators, may be used to modulate the activity of a SHIP polypeptide. Such SHIP modulators may be used to treat a SHIP-related disorder, for example and without limitation, a cancer, an immune disorder, a disorder of the hemopoietic system, a myelosuppressive disorder, or an inflammatory disorder. In general, SHIP modulators may be used to treat any disorder that may benefit from the activation or inhibition of a SHIP molecule.

Cancers include solid tumours and non-solid tumours. Solid tumours include carcinomas, which are the predominant cancers and are cancers of epithelial cells or cells covering the external or internal surfaces of organs, glands, or other body structures (e.g., skin, uterus, lung, breast, prostate, stomach, bowel), and which tend to mestastasize; sarcomas, which are derived from connective or supportive tissue (e.g., bone, cartilage, tendons, ligaments, fat, muscle); Carcinomas may be adenocarcinomas (which generally develop in organs or glands capable of secretion, such as breast, lung, colon, prostate or bladder) or may be squamous cell carcinomas (which originate in the squamous epithelium and generally develop in most areas of the body). Sarcomas may be osteosarcomas or osteogenic sarcomas (bone), chondrosarcomas (cartilage), leiomyosarcomas (smooth muscle), rhabdomyosarcomas (skeletal muscle), mesothelial sarcomas or mesotheliomas (membranous lining of body cavities), fibrosarcomas (fibrous tissue), angiosarcomas or hemangioendotheliomas (blood vessels), liposarcomas (adipose tissue), gliomas or astrocytomas (neurogenic connective tissue found in the brain), myxosarcomas (primitive embryonic connective tissue), or mesenchymous or mixed mesodermal tumors (mixed connective tissue types). In addition, solid tumours include mixed type cancers, such as adenosquamous carcinomas, mixed mesodermal tumors, carcinosarcomas, or teratocarcinomas.

Hematologic tumours are derived from bone marrow and lymphatic tissue. Hematologic tumours may be myelomas, which originate in the plasma cells of bone marrow; leukemias which may be "liquid cancers" and are cancers of the bone marrow and may be myelogenous or granulocytic leukemia (myeloid and granulocytic white blood cells), lymphatic, lymphocytic, or lymphoblastic leukemias (lymphoid and lymphocytic blood cells) or polycythemia vera or erythremia (various blood cell products, but with red cells predominating); or lymphomas, which may be solid tumors and which develop in the glands or nodes of the lymphatic system, and which may be Hodgkin or Non-Hodgkin lymphomas. In some embodiments, hematologic tumours, such as leukemias or lymphomas (e.g., acute lymphoblastic leukemia, acute myeloblastic leukemia, chronic myelogenous leukemia, Hodgkin's disease, multiple myeloma, non-Hodgkin's lymphoma), are specifically excluded.

Inflammatory disorders include, without limitation, rheumatoid arthritis, multiple sclerosis, Guillan-Barre syndrome, Crohn's disease, ulcerative colitis, inflammatory bowel syndrome, psoriasis, graft versus host disease, host versus graft, lupus erythematosis, Alzheimer's disease and insulin-dependent diabetes mellitus. Diseases related to inappropriate activation of macrophage-related cells of the reticuloendothelial lineage include osteoporosis.

Disorders of the hemopoietic system include, without limitation, leukemias such as chronic myelogenous leukemia and acute lymphocytic leukemia.

Myelosuppressive disorders include, without limitation, any disorder that results, in general, in a reduction in the production of blood cells. Myelosuppression therefore results in anemia, neutropenia, and thrombocytopenia. Myelosuppression may result from a number of different factors, including stress, illness (such as cancer), drugs (such as chemotherapeutics), radiation therapy, infection (e.g., by HIV virus, other viruses or bacteria), environmental insults (such as accidental or deliberate exposure to chemicals, toxins, radiation, biological or chemical weapons), aging or other natural processes, etc.

Immune disorders include, immune supression, which refers in general, to a systemic reduction in immune function as evidenced by, for example, compromised in vitro proliferative response of B and T lymphocytes to mitogens, reduced natural killer (NK) cell cytotoxicity in vitro, reduced delayed type hypersensitivity (DTH) skin test responses to recall antigens. Immune suppression may result from a number of different factors, including stress, illness (such as cancer), drugs (such as chemotherapeutics), radiation therapy, infection (e.g., by HIV virus, other viruses or bacteria), transplantation (e.g., of bone marrow, or stem cells, or solid organs), environmental insults (such as accidental or deliberate exposure to chemicals, toxins, radiation, biological or chemical weapons), aging or other natural processes, etc.

Test Compounds

SHIP modulators according to the invention include, without limitation, compounds selective for SHIP, for example, a SHIP C2 domain or a SHIP PH domain, analogs and variants thereof, including, for example, the molecules described herein. SHIP modulators may be identified using a variety of techniques, including screening of test compounds, combinatorial libraries or using predictive software.

A "test compound" is any naturally-occurring or artificially-derived chemical compound. Test compounds may include, without limitation, peptides, polypeptides, synthesised organic molecules, naturally occurring organic molecules, and nucleic acid molecules. A test compound can "compete" with a known compound such as a SHIP allosteric modulator (e.g., AQX-016A or AQX-MN100) or by, for example, interfering with binding to a C2 domain or a PH domain, or by interfering with any SHIP biological response induced by the known compound. Generally, a test compound can exhibit any value between 10% and 200%, or over 500%, modulation when compared to AQX-016A or AQX-MN100, or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator will in general decrease modulation relative to a known compound, while a compound that is a positive modulator will in general increase modulation relative to a known compound.

In general, test compounds are identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. Furthermore, if desired, any library or compound is readily modified using standard chemical, physical, or biochemical methods.

SHIP modulators may be identified based upon the ability of a test compound to bind to a SHIP C2 or PH domain, or modulate SHIP activity, using routine methods available in the art. Identified SHIP modulators may be subsequently evaluated for their ability to treat or prevent a SHIP-related disorder. In one embodiment, when a crude extract is found to treat or prevent a SHIP-related disorder, further fractionation of the positive lead extract is necessary to isolate chemical constituents responsible for the observed effect. Thus, the goal of the extraction, fractionation, and purification process is the careful characterization and identification of a chemical entity within the crude extract having the desired activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, diagnostic, or other value may be subsequently analyzed using an animal model, or any other animal model for a SHIP-related disorder.

In alternative embodiments, SHIP modulators according to the invention may be administered in combination with an agent suitable for treatment of a SHIP-related disorder, as described herein or known in the art.

Pharmaceutical Compositions and Administration

SHIP modulators may be provided alone or in combination with other compounds (for example, anti-inflammatory agents), in the presence of a liposome, an adjuvant, or any pharmaceutically acceptable carrier, in a form suitable for administration to mammals, for example, humans, cattle, sheep, etc. If desired, treatment with a compound according to the invention may be combined with more traditional and existing therapies for inflammatory disorders.

SHIP modulators may be provided chronically or intermittently. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature. In alternative embodiments, SHIP modulators are administered to a subject in need of such modulators, e.g., a subject having a SHIP-related disorder such as an inflammatory disease. In alternative embodiments, SHIP modulators may be administered to a subject before, after, or during an anti-inflammatory therapy.

In alternative embodiments, SHIP modulators may be effectively delivered by a variety of methods known to those skilled in the art. Such methods include but are not limited to liposomal encapsulation/delivery, vector-based gene transfer, fusion to peptide or immunoglobulin sequences for enhanced cell targeting and other techniques.

In alternative embodiments, SHIP modulators may also be formulated in pharmaceutical compositions well known to those in the field. Conventional pharmaceutical practice may be employed to provide suitable formulations or compositions to administer the compounds to subjects suffering from, at risk of, or presymptomatic for immune suppression or myelosuppression. Suitable pharmaceutical compositions may be formulated by means known in the art and their mode of administration and dose determined by the skilled practitioner. Any appropriate route of administration may be employed, for example, parenteral, intravenous, subcutaneous, intramuscular, intracranial, intraorbital, ophthalmic, intraventricular, intracapsular, intraspinal, intrathecal, intracisternal, intraperitoneal, intranasal, aerosol, lavage, topical, oral administration, or any mode suitable for the selected treatment. Therapeutic formulations may be in the form of liquid solutions or suspensions. For enteral administration, the compound may be administered in a tablet, capsule or dissolved in liquid form. The table or capsule may be enteric coated, or in a formulation for sustained release. For intranasal formulations, in the form of powders, nasal drops, or aerosols. For parenteral administration, a compound may be dissolved in sterile water or saline or a pharmaceutically acceptable vehicle used for administration of non-water soluble compounds such as those used for vitamin K.

Methods well known in the art for making formulations are found in, for example, Gennaro, A. (38). Formulations for parenteral administration may, for example, contain excipients, sterile water, or saline, polyalkylene, glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the compounds are administered to an individual in an amount sufficient to stop or slow hemopoietic cell death, or to enhance the proliferation of hemopoietic cells.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as treatment of immune suppression or myelosuppression. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as prevention or protection against hemopoietic cell death or maintenance of hemopoietic cells. Typically, a prophylactic dose is used in subjects prior to or at an earlier stage of disease, so that a prophylactically effective amount may be less than a therapeutically effective amount. A preferred range for therapeutically or prophylactically effective amounts of a compound may be any integer from 0.1 nM-0.1M, 0.1 nM-0.05M, 0.05 nM-15 µM or 0.01 nM-10 µM.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

As used herein, a subject may be a human, non-human primate, rat, mouse, cow, horse, pig, sheep, goat, dog, cat, etc. The subject may be a clinical patient, a clinical trial volunteer, an experimental animal, etc. The subject may be suspected of having or at risk for a SHIP-related disorder, be diagnosed with a SHIP-related disorder, or be a control subject that is confirmed to not have a SHIP-related disorder. Diagnostic methods for and the clinical delineation of SHIP-related disorders are known to those of ordinary skill in the art.

The present invention will be further illustrated in the following examples.

EXAMPLE 1

Materials and Methods

Construction of the SHIP ΔC2 Mutant and Isolated C2 and PH Domains

```
SHIP1 ΔC2:
Upstream Fragment
                                      (SEQ ID NO: 38)
Sense
5'-TTC ATG TTC ATT GGA ACC TCC-3'

(SEQ ID NO: 39)
Anti-Sense
5'-TTT GCG GCC GCA CCA TTC TTG GAG ACG AAT
TG-3'

Downstream Fragment
                                      (SEQ ID NO: 40)
Sense
5'-TTG CGG CCG CTA GGG AGA AGC TCT ATG ACT
TT-3'

(SEQ ID NO: 41)
Anti-Sense
5'-TTT CTA GAT TAC ATG GCA GTC CTG CCA AGC
AG-3'

C2 Domain:
                                      (SEQ ID NO: 42)
Sense
5'-AAA TTT CAT ATG CCT GGC ACT GTA GAT AGC
CAA-3'

(SEQ ID NO: 43)
Anti-Sense
5'-TAT GAA TTC TTA CAT CTT GCC CTG GGA GGT
CTG-3'

SHIP1 (delta) PH:
Upstream Fragment
                                      (SEQ ID NO: 44)
sense:
5'-GTA GAA AGT GTC ATG TCA CCA-3'

(SEQ ID NO: 45)
anti-sense:
5'-tt AGC GGC CGC TTC TGA GCC CTC GTG CAG
CAA-3'

Downstream Fragment
                                      (SEQ ID NO: 46)
sense:
5'-tt GCG GCC GCT CCT GAC ATG ATC ACC ATC
TTC-3'

(SEQ ID NO: 47)
anti-sense:
5'-TGC ATA CTT GTC CCG GGT CAG-3'
```

-continued

PH Domain:

(SEQ ID NO: 48)
sense:
5'-aaa ttt CAT ATG TCT ACC AAC AGG CGT TCC CTT-3'

(SEQ ID NO: 49)
anti-sense:
5'-tat GAA TTC TTA CTC TGG CTG CTC CGA ATG CTT -3'

The mouse SHIP1 ΔC2 domain deletion mutant was generated by a standard PCR-based methodology using the primer pairs listed above, which in addition to being complementary to sequences immediately upstream and downstream of the C2 domain (amino acid residues 725 to 863), introduces a NotI restriction site. The PCR-products were digested with ClaI and NotI, and NotI and XbaI for the upstream and downstream fragments, respectively. Products were then resolved and imaged on a 1% agarose gel containing ethidium bromide and the appropriate sized fragments excised and purified using a column gel extraction kit (Qiagen, Mississauga, ON). In parallel, pME18S plasmid containing the cDNA for N-terminal His6-tagged SHIP1 was digested with ClaI and NotI, resolved and purified as before. Upstream fragment, downstream fragment and digested pME18S-SHIP plasmid were ligated to yield a plasmid coding for SHIP1 with the C2 domain deleted. An N-terminal His6 C2 domain was also generated by PCR using the primer pair indicated above and the resulting product inserted into the pET28C bacterial expression vector using EcoRI and NdeI restriction sites.

The SHIP1 PH domain deletion mutant and an isolated PH domain construct were generated using techniques similar to those used for the C2 domain. More specifically, the PH domain (amino acids 984-1319) was deleted from the murine SHIP (mSHIP) cDNA as follows: using pME18S-mSHIP1 as a template, a 527 by PCR fragment ("Upstream Fragment") was generated using the indicated primers to generate a fragment corresponding to sequence immediately upstream of the SHIP PH domain within which resides a unique AccI restriction cut site. A Nod restriction cut site was also introduced to the 3' end of this fragment. The PCR product was digested with Acd and Nod, and gel purified. Using pME18S-mSHIP1 as a template, a 776 by PCR fragment ("Downstream Fragment") was generated using the indicated primers corresponding to sequence immediately downstream of the SHIP PH domain within which resides a unique ClaI restriction cut site. A Nod restriction cut site was introduced to the 5' end of this fragment. The PCR product was digested with NotI and ClaI and gel purified. pME18S-mSHIP1 plasmid was digested with AccI and ClaI generating a 1.4 kb internal fragment and a 6.8 kb fragment containing the amino and carboxyl terminals of SHIP. The 6.8 kb pME18s-mSHIP1 fragments, 5'PCR and 3' PCR fragments were ligated together to generate the ΔPH mutant SHIP construct.

The PH domain construct was generated as follows. Using pME18S-mSHIP1 as a template, a 338 bp PCR fragment was generated using Pfu polymerase corresponding to the boundaries of SHIP's predicted PH domains (mouse amino acids 984-1319) using primers as indicated. These primers introduce a NdeI restriction site to the 5' end and a stop codon and EcoRI cut site introduced to the 3' end of this fragment. The NdeI/EcoRI digested PCR product was gel purified and ligated to appropriated digested vector.

Production of recombinant SHIP1 enzyme and SHIP1 C2 and PH domains: Recombinant, N-terminal His6 tagged SHIP1 enzyme was expressed in mammalian 293T cells by transient transfection with pME18S-His-SHIP plasmid and purified to >95% homogeneity by Nichelating bead chromatography (Qiagen, Mississauga, Ontario) as assessed by Coomassie Blue visualization of sodium dodecyl sulfate-polyacrylamide gel electrophoresis (SDS-PAGE) separated material. Recombinant SHIP1 C2 domain (amino acid residues 725 to 863) or SHIP1 PH domain (amino acid residues 984-1319) were expressed in E. coli transformed with a pET28C expression vector constructed as described herein. Cultures were induced overnight with 1 mM IPTG, and protein purified from the cell lysates by Ni-chelating bead chromatography was >95% pure by SDS-PAGE analysis.

In vitro SHIP enzyme assay. The SHIP enzyme assay was performed in 96-well microtitre plates with 10 ng of enzyme/well in a total volume of 25 μL of 20 mM Tris HCl, pH 7.5 and 10 mM $MgCl_2$. SHIP1 enzyme was incubated with test extracts (provided in DMSO) or vehicle for 15 mM at 23° C. before the addition of 100 μM inositol-1,3,4,5-tetrakisphosphate (Echelon Biosciences Inc, Salt Lake City, Utah). The reaction was allowed to proceed for 20 min at 37° C. and the amount of inorganic phosphate released assessed by the addition of Malachite Green reagent followed by an absorbance measurement at 650 nm (15). SHIP2 enzyme was purchased from Echelon Biosciences (Salt Lake City, Utah) and an equivalent amount of inositol phosphatase activity was used in the in vitro enzyme assay. Enzyme data are expressed as the mean of triplicates+/−SEM. Experiments were performed at least 3 times.

Inositol phospholipid analysis. J16 cells, a macrophage cell line immortalized from C57B16 mice, were grown in 10% FCS in IMDM supplemented with 10 μM 2-mercaptoethanol, 150 μM monothioglycolate (MTG) and 1 mM glutamine. $5 \times 10^6$ cells were plated the night before in 10 cm tissue culture dishes. The next day, cells were washed three times with phosphate-free medium before being starved in phosphate free RPMI (MP Biomedicals, Irvine, Calif.) supplemented with 10% dialyzed FCS (Invitrogen, Burlington, Ont) and 1% RPMI for 2 hrs. Cells were then labeled with 1.0 mCi of $^{32}P$-labeled orthophosphate (MP Biomedicals, Irvine, Calif.)/ml for 2 hrs at 37° C. Cells were pretreated for 30 mM with AQX-016A, LY294004 or vehicle prior to stimulation with LPS (50 ng/ml) for 15 min. Extraction of inositol phospholipids and HPLC analysis of deacylated lipids were performed as described previously (16). The amount of radioactivity contained in the elution peak for each lipid (two to five fractions) was summed to give the total counts for each lipid, and data were normalized to the first 60 fractions to adjust for fluctuations in total lipid labeling and recovery between samples. Data are expressed as the mean+/− the SEM of three independent replicates for each stimulation condition and the experiment was repeated twice.

Production of SHIP+/+ and SHIP−/− BMMCs and BMnϕs. To obtain BMMCs, bone marrow cells were aspirated from 4 to 8 week old C57B16×129Sv mixed background mice and SHIP1+/+ and SHIP1−/− BMMCs prepared as described previously (17). After 8 weeks in IMDM+15% FCS (StemCell Technologies, Vancouver, Canada)+150 μM MTG+30 ng/ml IL-3 (BMMC medium) more than 99% of the cells were c-kit and FcεR1 positive as determined by flow cytometry with FITC-labeled anti-c-kit (BD Pharmingen, Mississauga, Canada) and FITC-labeled IgE (anti-Epo), respectively. BMmϕs from SHIP1+/+ and SHIP1−/− mice were obtained and maintained in IMDM supplemented with 10% FCS, 150 μM MTG, 2% C127 cell conditioned medium as a source of macrophage colony stimulating factor (MCSF) (BMmϕ medium).

LPS stimulation of BMmφs. For the analysis of LPS-stimulated TNFα production, 2 ×10$^5$ cells were plated the night before in 24 well plates in BMmφp medium. The next day, the medium was changed and AQX-016A or carrier was added to cells at the indicated concentrations for 30 min prior to the addition of 10 ng/mL LPS. Supernatants were collected after 1 hr for TNFα determination by ELISA (BD Biosciences, Mississauga, ON, Canada). Data are expressed as the mean +/− SEM of triplicates and experiments were repeated 3 times. For analysis of intracellular signaling, 2×10$^6$ cells were plated the night before in 6 cm tissue culture plates. The next day, the cells were cultured in BMmφp medium without M-CSF for 1 hr at 37° C. and then pretreated with AQX-016A or carrier for 30 min prior to the addition of 10 ng/mL LPS for 15 min. Cells were washed with 4° C. PBS and resuspended in lysis buffer (50 mM Hepes, 2 mM EDTA, 1mM NaVO4, 100 mM NaF, 50 mM NaPPi and 1%NP4O) supplemented with COMPLETE™ Protease Inhibitor Cocktail (Roche, Montreal, Canada). Lysates were rocked at 4° C. for 30 min and clarified by centrifuging 20 min at 12000×g. Lysates were then made 1× in Laemmli's buffer, boiled 2 min and loaded onto 7.5% SDS polyacrylamide cells. Immunoblot analysis for phospho PKB (Cell Signalling, Mississauga, Ont), SHIP1 and actin (Santa Cruz, Santa Cruz, Calif.) were carried out as described previously (18). Results are representative of 3 independent experiments.

Stimulation of BMMCs by FcεR1 crosslinking. SHIP1+/+ and SHIP1−/− BMMCs were pre-loaded overnight in BMMC medium lacking IL-3 with 0.1 μg/ml anti-DNP IgE (SPE-7, Sigma, Oakville, Ont). For calcium flux measurements, the cells were incubated with 2 μM fura 2-acetoxymethyl ester (Molecular Probes, Eugene, Oreg.) in Tyrode's buffer at 23° C. for 45 min. The cells were then washed and incubated in the presence of vehicle control, LY294002 or AQX-016A 30 min prior to stimulation with the indicated concentration of DNP-human serum albumin (DNP-HSA). Calcium influx was then monitored by spectrofluorometry as described previously (19). Experiments were repeated at least 3 times. For analysis of intracellular signaling, cells were pre-loaded with anti-DNP IgE as above, pre-treated with AQX-016A or buffer control for 30 min at 37° C. and stimulated with 20 ng/ml DNP-HSA for 5 min. Total cell lysates were then prepared and analyzed for phospho-PKB, phospho-p38MAPK, phospho-MAPK, Grb-2 (Cell Signalling, Mississauga, Ont) and SHIP1 (18) by immunoblot analysis as described previously (20). Results are representative of 3 independent experiments.

Mouse septicemia model. 6-8 week old C57B16 mice (VCHRI Mammalian Model of Human Disease Core Facility, Vancouver, BC) were orally administered the indicated dose of AQX-016A, AQX-MN100 or dexamethasone or carrier 30 min prior to an IP injection of 2 mg/kg of LPS (E. Coli serotype 0111:B4, Sigma, Oakville, Ont). Blood was drawn 2 hrs later for determination of plasma TNFα by ELISA. Results are representative of 3 independent experiments.

Mouse acute cutaneous anaphylaxis model. 6-8 week old CD1 mice (University of British Columbia Animal Facility, Vancouver, BC) were sensitized to the hapten DNP by cutaneous application of 25 μL of 0.5% dinitroflourobenzene (DNFB) (Sigma, Oakville, Ont) in acetone to the shaved abdomen of mice for two consecutive days. In the AQX-016A experiments shown in FIG. 2F, 20 μCi of tritiated thymidine [3H]-Tdr (GE Healthcare, Piscataway, N.J.) was injected EP one week after the first DNFB application. [3H]-Tdr labels rapidly dividing cells of the mouse, including neutrophils (21). 24 hrs later, test substances (dissolved in 10 μL of 1:2 DMSO:MeOH) were painted on the right ear while the left ear received vehicle control. 30 min after drug application, DNFB was applied to both ears to induce mast cell degranulation. The resulting inflammatory cell infiltration was quantitated by taking a 6mm diameter punch from the ear 1 hr later for dissolution in SOLVABLE™ (Perkin Elmer-Packard, Woodbridge, Ont) and liquid scintillation counting as described (21). The ability of test substances to inhibit mast cell degranulation was then determined by calculating the ratio of [3H]-Tdr in the test (right) ear vs the control (left) ear as described (21). One group of mice had DNFB applied only to the left ear leaving the right ear non-inflamed, in order to control for basal [3H]-Tdr incorporation into ear parenchymal cells.

In the later AQX-MN100 experiments, shown in FIG. 3E, the mice were sensitized as above with DNFB. However, instead of labeling the mice with [3H]-Tdr, a 6 mm punch was taken from the ear and immediately frozen on dry ice for subsequent determination of neutrophil myeloperoxidase (MPO) activity as described (22). Briefly, tissue samples were homogenized for 1 min with a Polytron PT 3000 homogenizer in a solution of 0.5% hexadecyltrimethylammonium bromide dissolved in phosphate buffer solution (pH 6.0). The homogenized tissues were centrifuged at 13,000×g for 10 min in a refrigerated centrifuge. Supernatants were added to a buffer supplemented with 1% hydrogen peroxide, and O-dianisidine dihydrochloride solution in a microtitre well plate. Optical density readings at 450 nm were taken over 10 min at 30 s intervals. MPO activity was calculated as described (22) and expressed as Units per mg of protein per mL of lysate. Results are representative of 3 independent experiments.

Protein Lipid Overlay Assays Protein Lipid Overlay assays were performed essentially as described (23) with minor modifications. Lyophilized phosphatidylinositol-3,4-bisphosphate diC16 (PIP2, Echelon Biosciences, Salt Lake City, Utah) was reconstituted in a 2:1.8 solution of methanol and water. PVDF membranes (Millipore, Missisauga, Ont) were initially wetted in methanol for 1 minute, and washed 3×5 min with water, and gently agitated in TBST buffer (20 mM Tris pH 7.5, 0.15 M NaCl (TBS) with 0.05% Tween 20) at 23° C. overnight. The treated membranes were air-dried and dilutions of reconstituted lipids were spotted in 1 μl aliquots to give the indicated amount of PIP2 per membrane spot. The membranes were dried completely and blocked with blocking buffer (3% BSA in TBS with 0.05% NaN3) for 1 h at 23° C. on a gentle shaker. Purified, recombinant C2 domain was diluted into blocking buffer (5 μM final) and treated with 200 μM AQX-MN100 or EtOH control for 30 min at 23° C. prior to overnight incubation with the PIP2 spotted membranes. The membranes were washed 10 times over 50 min in TBST buffer at 23° C. and were incubated with anti-His6 mouse IgG (Qiagen, Missisauga, Ont) for 1 hour at 23° C. with gentle rocking. The membranes were washed 10 times over 50 min in TBST buffer at 23° C. and were incubated with Alexa Fluor 660 anti-mouse goat anti-mouse IgG (Invitrogen, Burlington, Ont) for 1 h at 23° C. The membranes were washed 3 times in TBST over 15 min at 23° C. and the bound proteins were detected and quantified on a Li-Cor Odyssey scanner (Lincoln, Nebr.). Results are representative of 3 independent experiments.

Scintillation Proximity Assays AQX-MN100 was radiolabeled with tritium by GE Healthcare (Piscataway, N.J.) to a specific activity of 42 Ci/mmole. Copper chelate (His-Tag) YSi YSi SPA Scintillation Beads (GE Healthcare, Piscataway, NJ) were diluted in 0.25% BSA/TBS to 1.5 mg/mL and recombinant, His6-tagged protein added at the indicated concentrations: wild-type (1 pM), ΔC2 SHIP enzyme (1 pM) or C2 domain (10 nM). Protein was allowed to bind 1 h at 23° C., and 250 µg of beads were aliquoted per well of a 96-well plate. 5 µCi of [3H]-AQX-MN100 was added per well, the plate gently agitated for 30 min and the amount of bead associated radioactivity quantified by counting in a Wallac BETAPLATE™ plate scintillation counter. Results are representative of 3 independent experiments.

In vitro kinase/phosphatase screen Compound profiling activity was undertaken using 100 protein kinase and phosphatase targets by SignalChem (Richmond, BC, Canada) against compound AQX-MN100 (50 µg/ml final concentration) in the presence of 50 µM ATP. Protein kinase assays were performed at 30° C. for 15 min in a final volume of 25 µL. The assay was initiated by the addition of [32P]-ATP and the reaction mixture incubated at 30° C. for 15 minutes. After the 15 minute incubation period, the assay was terminated by spotting 20 µl of the reaction mixture onto phosphocellulose P81 plate. The phosphocellulose P81 plate was washed 3 times for approximately 15 minutes each in a 1% phosphoric acid solution. The radioactivity on the P81 plate was counted in the presence of scintillation fluid in a scintillation counter. Protein phosphatase activities were determined using pNPP as substrate. Assays were performed at 37° C. for 15 min in a final volume. The assay was started by incubating the reaction mixture at 37° C. for 15 minutes. After the 15 minutes incubation period, the assay was terminated by the addition of 25 µl of 2N NaOH stopping solution. The absorbance of the reaction solution was measured in a spectrophotometer at 410 nm. The activity of the enzymes in the presence of AQX-MN100 was compared to that in the vehicle control and expressed as a % change in activity relative to that observed in the vehicle control. Changes in activity of <25% were not considered significant.

Results

Figure 1A:
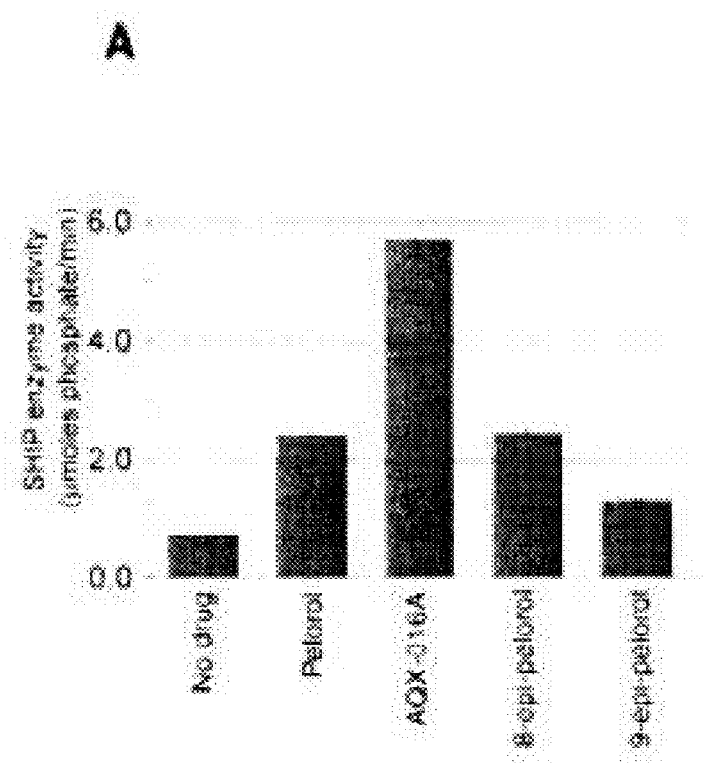
FIGS. 1A-D show that AQX-016A increases SHIN enzyme activity in vitro and in vivo. (A) 40 μg/mL of purified Pelorol, AQX-016A, 8-epi-pelorol and 9-epi-pelorol were tested for their ability to enhance SHIP1's enzyme activity. (B) The effect of AQX-016A on SHIP1 (.) and SHIP2 (.) enzyme activity was compared in in vitro enzyme assays. In panels (C) and (D), J16 cells were treated for 30 min with 5 mg/mL AQX-016A, 25 μM LY294002 or carrier prior to stimulation with 50 μg/mL of LPS for 15 min at 37° C. Cellular lipids were extracted and analyzed for PIP3 (panel C) and PI-3,4-P2 (panel D) levels as described in the Examples. Data are expressed as mean+/−SEM and are representative of three independent experiments.
Figure 1B:
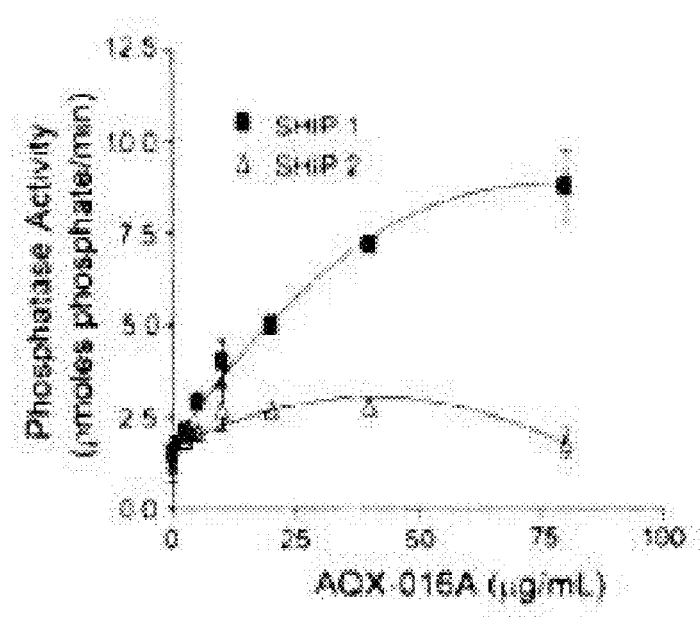
Figure 1C:
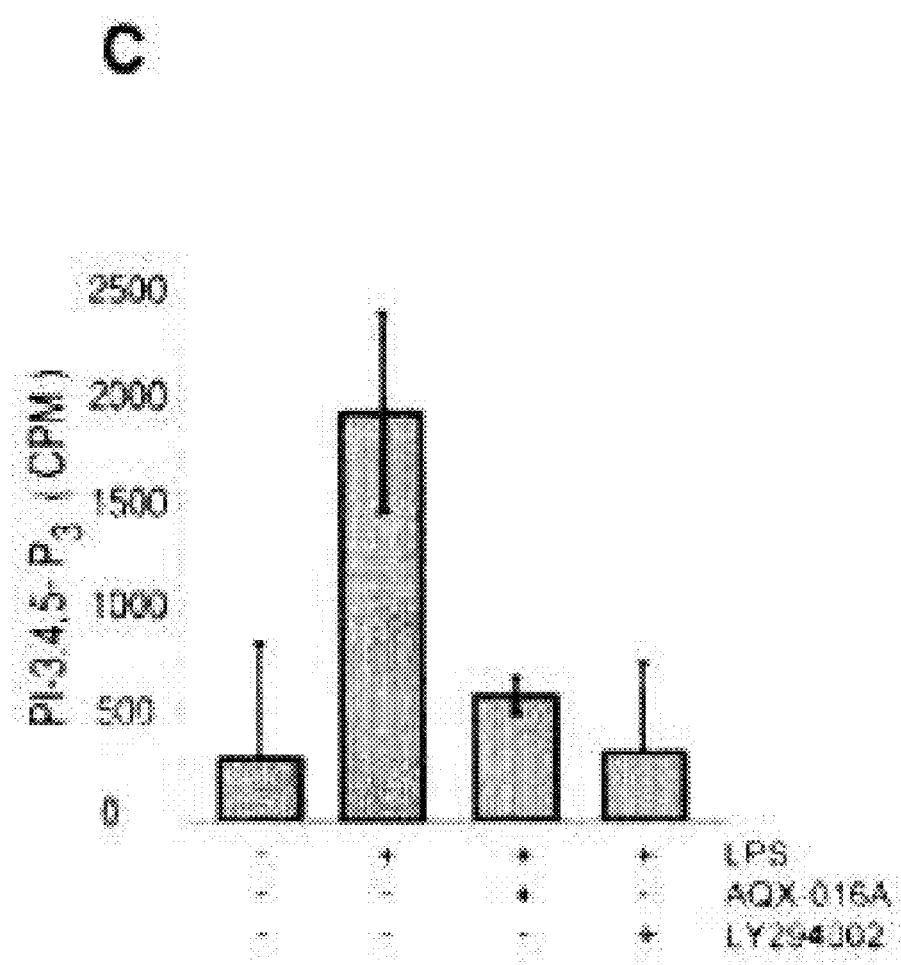
Figure 1D:
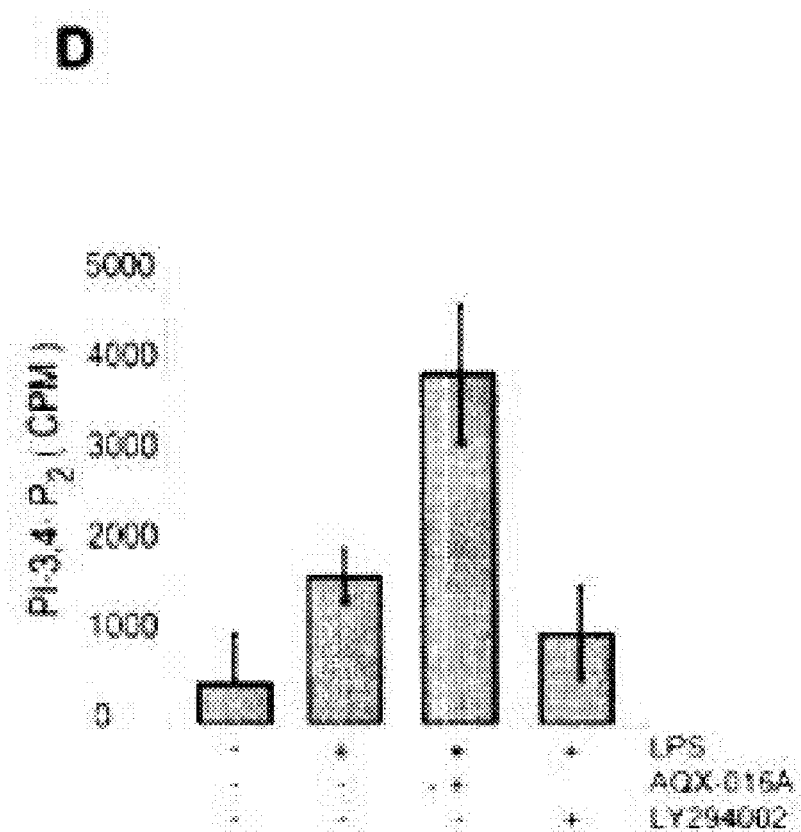

A small molecule compound, AQX-016A (FIG. 3A) was tested for SHIP activation, and produced a 3-fold higher activation of SHIP1 than Pelorol (FIG. 1A). To evaluate the specificity of AQX-016A for SHIP1, we assessed AQX-016A's ability to activate its most closely related inositol phosphatase, SHIP2. As shown in FIG. 1B, AQX-016A preferentially activates SHIP1 over SHIP2. We then determined whether AQX-016A was able to activate SHIP1's enzyme activity in intact cells by analyzing the inositol phospholipid content of macrophages stimulated with lipopolysaccharide (LPS) in the presence or absence of AQX016A. As shown in FIG. 1C, LPS stimulated a 3-5 fold increase in PIP3 levels, in keeping with the ability of LPS to activate the PI3K pathway (2). AQX-016A abolished this increase (FIG. 1C) and resulted in a corresponding increase in the SHIM hydrolysis product PI-3,4-P2 (FIG. 1D) whereas the PI3K inhibitor LY294002 diminished PIP3 levels without a corresponding increase in PI-3,4P2 levels. The specific increase in the SHIP1 product, PI-3,4-P2, observed in AQX-016A treated cells, is consistent with SHIP1-mediated 5'-dephosphorylation of PIP3.

Figure 2:
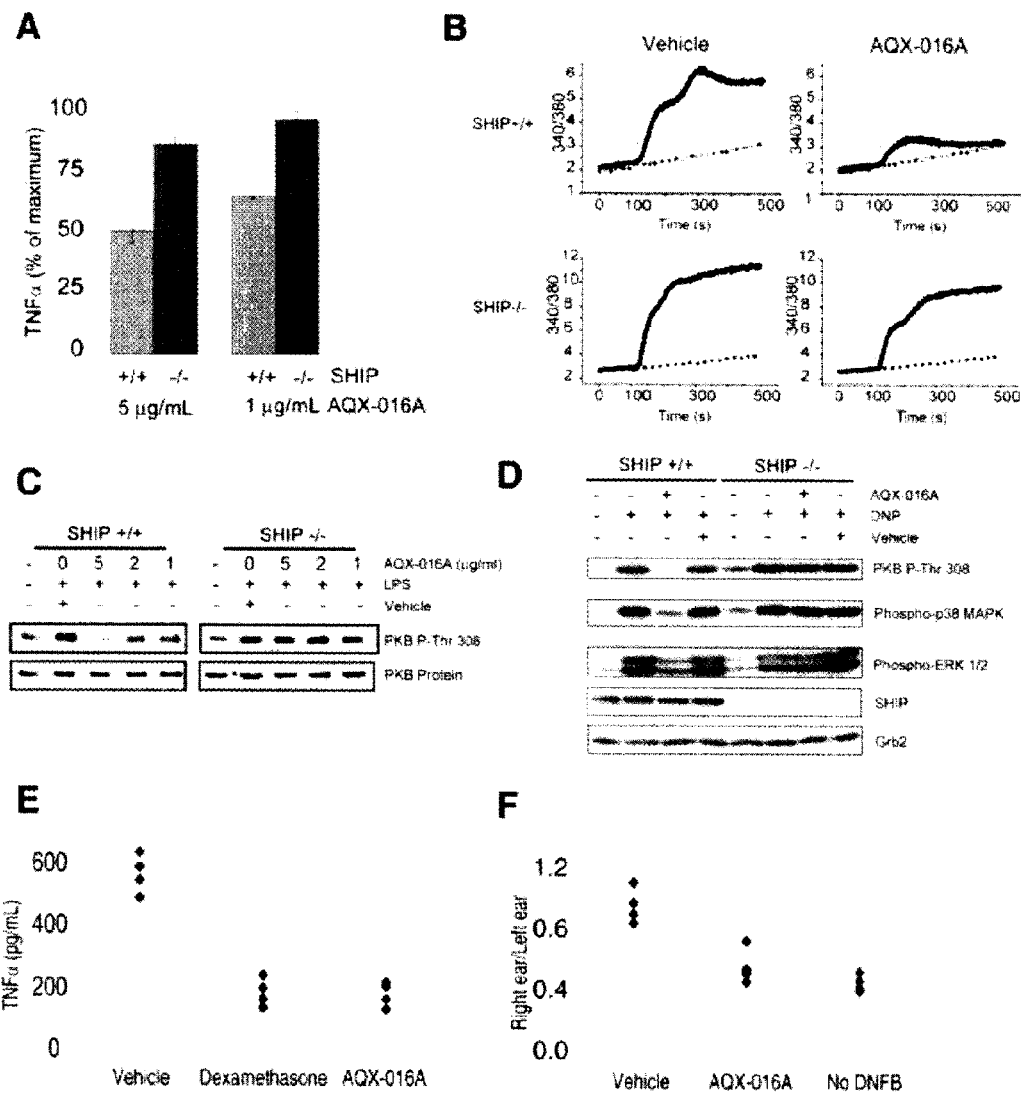
FIGS. 2A-F show that AQX-016A inhibits immune cell activation. (A) SHIP1$^{+/+}$ (▦) and SHIP1$^{-/-}$ (■) BMmφs were pretreated with AQX-016A or carrier 30 min prior to stimulation with 10 ng/mL of LPS at 37° C. for 2 h and TNFα, production determination by ELISA. Absolute TNFα levels for SHIP1+/+ and SHIP1−/− cells were 623+/−30 and 812+/−23 pg/ml, respectively. Data are expressed as mean+/−SEM and are representative of three independent experiments. (B) SHIP1+/+ and SHIP1−/− BMMCs were pre-loaded with IgE and Fura-2 as described in the Examples and treated for 30 min with 0.5 μg/ml AQX-016A or carrier. Cells were then stimulated (as indicated by the arrow) with 0 (....) or 10 (.) ng/mL DNP-HSA and intracellular calcium levels monitored over time by spectrofluorometry. (C) SHIP+/+ and −/−BM-mφs were pretreated for 30 min with AQX-016A or carrier prior to stimulation with 10 ng/mL of LPS for 15 min at 37° C. Total cell lysates were analyzed for the indicated phosphoproteins or proteins by immunoblot analysis (D) Anti-DNP-IgE loaded SHIP1+/+ and −/−BMMCs were treated for 30 min with 10 μg/ml AQX-016A or carrier prior to stimulation with 20 ng/ml DNP-HSA for 5 min at 37° C. and cell lysates analyzed as in C. (E) Mice were administered 20 mg/kg AQX-016A or 0.4 mg/kg dexamethasone orally 30 min prior to an IP injection of 2 mg/kg LPS. Blood was collected 2 h later for TNFα determination by ELISA. (F) 10 μg/ml of AQX-016A or vehicle was applied to the right ears of DNP-sensitized, [3H]-Tdr labeled mice 30 min prior to application of DNFB to both ears. The no DNFB group had DNFB applied only to the left ear. For E and F, each symbol indicates one mouse and data are representative of three independent experiments.
Figure 5:
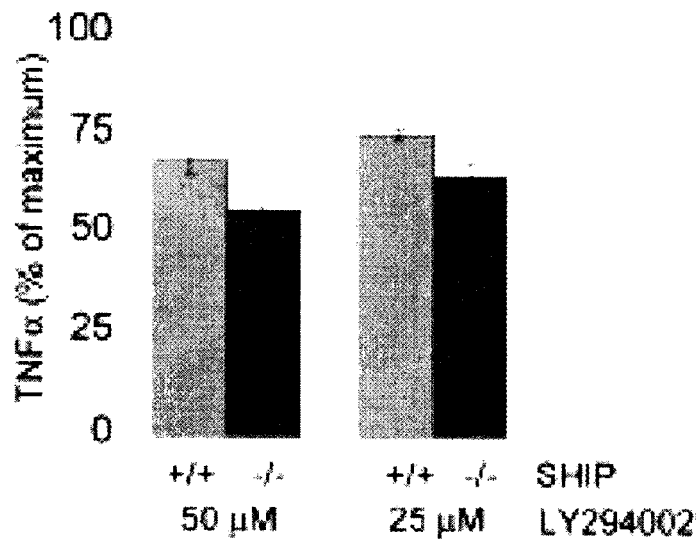
FIGS. 5A-B show the effects of LY294002 (A) LY294002 inhibits TNFα expression in both SHIP1$^{+/+}$ and SHIP1$^{-/-}$ macrophages. SHIP1$^{+/+}$ (▦) and SHIP1$^{-/-}$ (■) bone marrow derived macrophages were pretreated with LY294002 or carrier for 30 min prior to stimulation with 10 ng/mL of LPS at 37° C. and TNFα levels determined by ELISA. Absolute TNFα levels for SHIP1$^{+/+}$ and SHIP1$^{-/-}$ cells were 693+/−37 and 921+/−21 pg/mL, respectively (B) LY294002 inhibits calcium flux in both SHIP1$^{+/+}$ and SHIP1$^{-/-}$ mast cells. SHIP1$^{+/+}$ and SHIP1$^{-/-}$ bone marrow derived mast cells, pretreated overnight with 0.1 ug/ml IgE (SPE-7), were incubated for 30 min with the indicated concentration of LY294002. Cells were then stimulated or not (▬▬▬▬) with 5 ng/mL DNP-HSA (arrow) and intracellular calcium levels monitored over time by spectrofluorometry.
Figure 5:
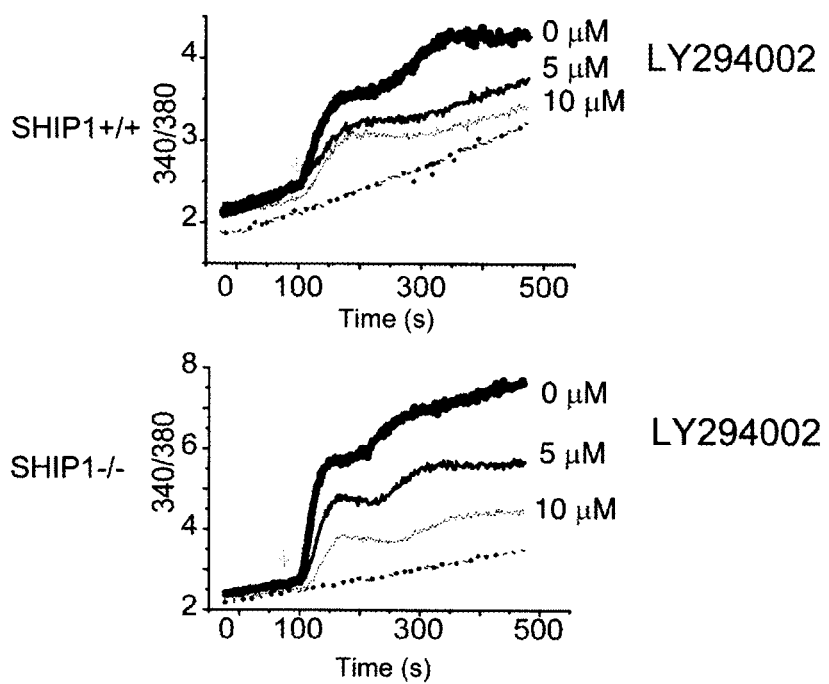

We further validated the target specificity and biological efficacy of AQX-016A by comparing its effects on SHIP1-regulated processes in primary SHIP1+/+ vs SHIP1−/− macrophages and mast cells. Both LPS-induced macrophage (2) and IgE-induced mast cell activation (3-5) are negatively regulated by SHIP1. LPS stimulation of macrophages is associated with a PIP3 dependent release of pro-inflammatory mediators such as TNFα (2). We examined the action of AQX-016A on SHIP1+/+ vs SHIP1−/− bone marrow derived macrophages (BMmfs) and confirmed AQX-016A preferentially inhibited LPS-stimulated TNFα production in SHIP1+/+ than in SHIP1−/− BMmfs (FIG. 2A). Activation of mast cells via IgE+antigen crosslinking of their IgE receptors results in elevation of intracellular calcium levels (3, 6). As shown in FIG. 2B, AQX-016A inhibited IgE+antigen-induced calcium entry to a substantially greater degree in SHIP1+/+ than in SHIP1−/− bone marrow derived mast cells (BMMCs). For comparison, the PI3K inhibitor LY294002 inhibited both SHIP+/+ and SHIP−/− macrophages and mast cells to the same extent (FIGS. 5A-B). These data indicate that AQX-016A inhibits both macrophage and mast cell activation in a SHIP1-dependent manner.

We then compared the ability of AQX-016A to inhibit PI3K-dependent activation of downstream signaling proteins (3,5,7,8) in SHIP1+/+ vs SHIP1−/− cells. As shown in FIG. 2C, AQX-016A preferentially inhibited, in a dose dependent manner, LPS-stimulated PKB phosphorylation in SHIP1+/+ but not in SHIP1−/− BMmfs. Similarly, AQX-016A inhibited the phosphorylation of PKB, p38MAPK and ERK in SHIP1+/+ but not in SHIP1−/− BMMCs (FIG. 2D). We also examined the ability of AQX-016A to inhibit PKB activation in non-hemopoietic, prostate epithelial LNCaP cells, which do not express SHIP1. As shown in FIG. 6, LY294002 efficiently inhibited PKB phosphorylation whereas AQX-016A had no effect. Thus, AQX016A inhibits PIP3-regulated intracellular signal transduction events in SHIP1-expressing hemopoietic cells, but not in SHIP1-deficient hemopoietic or non-hemopoietic cells.

We then tested whether AQX-016A would be protective in mouse inflammatory disease models. In the septicemia model, injection of LPS results in inflammatory cell activation that can be quantified by measuring plasma levels of TNFα (9). We found that oral administration of AQX-016A 30 min prior to LPS challenge reduced the level of TNFα to the same extent as the control, anti-inflammatory steroidal drug dexamethasone (FIG. 2E). In the mouse ear edema/cutaneous anaphylaxis model (10), mice are pre-sensitized to allergen (DNFB) and cutaneous anaphylaxis is subsequently induced by applying the same allergen to their ears. The degree of inflammation is quantified by measuring the recruitment of inflammatory cells to the test ear. As shown in FIG. 2F, topically applied AQX-016A dramatically inhibited allergen-induced inflammation compared to the vehicle control-treated ear. Thus AQX-016A is protective in both septicemia and acute cutaneous anaphylaxis models, and is both orally and topically bioavailable.

Figure 3A:
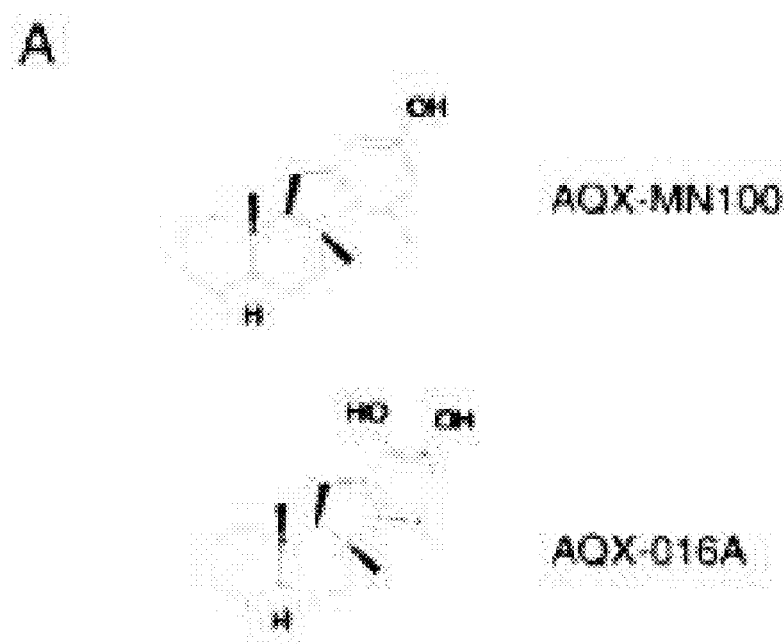
FIGS. 3A-E show that AQX-MN100 has the same biological activities as AQX-016A (A) Structures of AQX-MN100 and AQX-016A (B) AQX-MN100 activates SHIP enzyme activity in vitro. Assays were performed as in FIG. 1A. (C) AQX-MN100 inhibits TNFα production from LPS stimulated SHIP1+/+ but not −/− BMmφs. Cells and treatments were as described in FIG. 2A. (D) AQX-MN100 inhibits LPS-induced plasma TNFα levels in mice. Mice were treated as in FIG. 2E. (E) AQX-inhibits DNFB-induced MPO in sensitized mice. Mice were sensitized as in FIG. 2F, and vehicle or AQX-MN100 applied to pairs of ears prior to DNFB challenge. Some mice were not challenged with DNFB (no DNFB). Ears were harvested and MPO levels determined. P-value <0.02 for the AQX-MN100 vs the vehicle treated groups. Data are representative of three independent experiments.
Figure 3B:
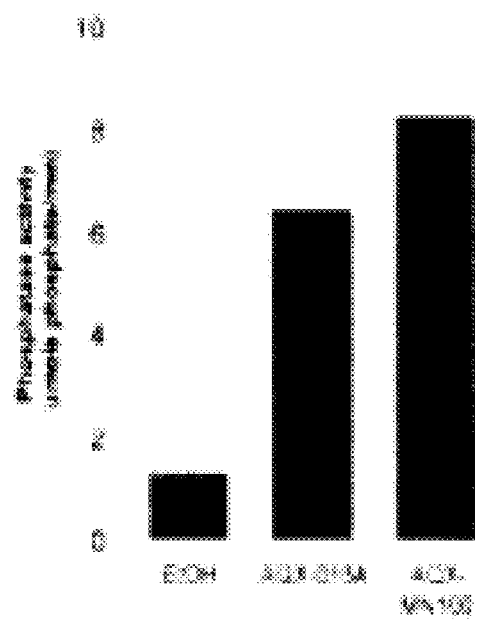
Figure 3:
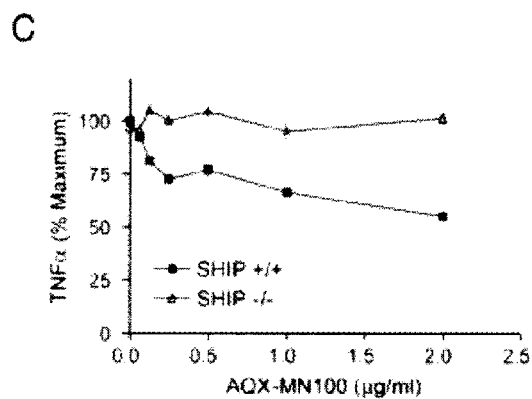
Figure 3D:
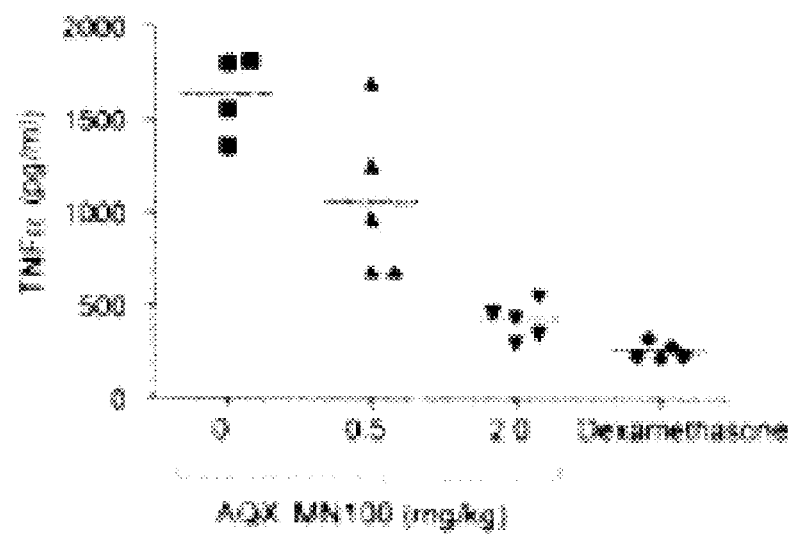

Our observation that AQX-016A is substantially more active on SHIP1+/+ than SHIP1−/− cells suggests it acts by specifically targeting SHIP. However, the presence of a catechol moiety within AQX-016A is potentially problematic since catechols can exhibit activities independent of their specific protein pocket binding interaction. For example, catechols can bind metals or be oxidized to an ortho-quinone which can lead to covalent modification of proteins through redox reactions (11). To rule out these possibilities we synthesized a non-catechol version of AQX-016A designated AQX-MN100 (FIG. 3A). Analogous to AQX-016A, AQX-MN100 enhanced SHIP1 enzyme activity in vitro (FIG. 3B) and selectively inhibited TNFα production from SHIP1+/+ but not SHIP1−/− macrophages (FIG. 3C). Oral administration of AQX-MN100 also efficiently inhibited the LPS-induced elevation of plasma TNFα levels in the mouse septicemia model (FIG. 3D). As well, topical administration of AQX-MN100 reduced the levels of the inflammatory cell (neutrophil) specific myeloperoxidase enzyme detected in the ears of allergen-challenged mice in the cutaneous anaphylaxis model (FIG. 3E). Thus the SHIP1 activating and subsequent anti-inflammatory activities of the Pelorol family of compounds do not appear to be due to non-specific activity of the catechol moiety.

Figure 4:
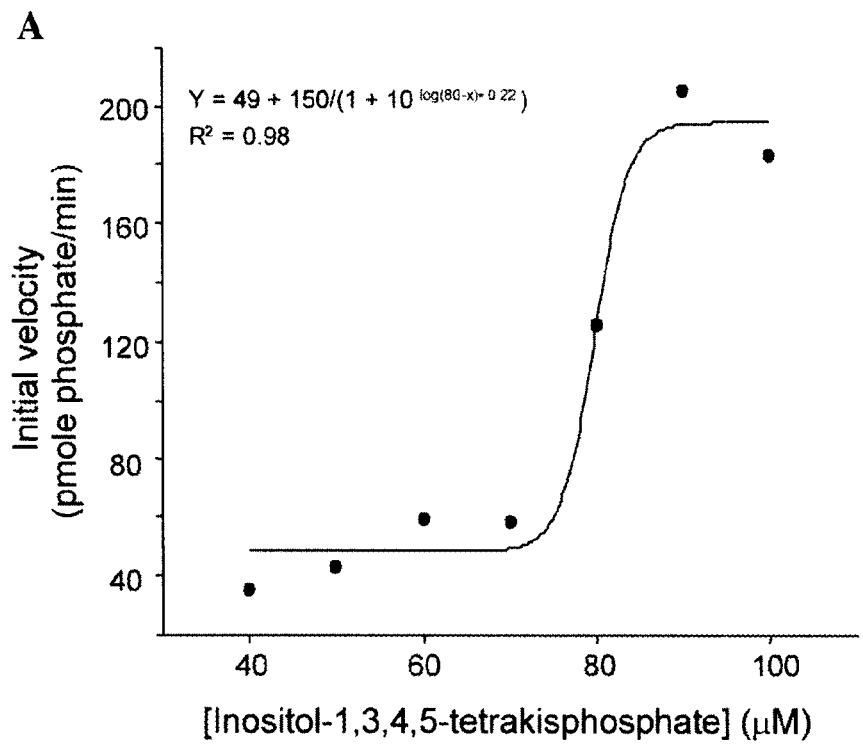
FIGS. 4A-D show that the C2 domain is required for end-product allosteric activation of SHIP1 and binding of AQX-MN100 (A) SHIP1 enzyme initial velocities were determined at the indicated concentration of inositol 1,2,4,5-tetrakisphosphate (IP4) substrate. (B) The ability of product PI-3,4-P2 (20 μM) or AQX-MN100 (80 μg/mL=250 μM) to activate wild-type (WT) and C2 domain deleted (ΔC2) SHIP1 enzyme was determined at 30 μM IP4. (C) Recombinant C2 domain was pre-incubated for 30 min at 23° C. with 200 μM AQX-MN100 or EtOH control and allowed to bind to PI-3,4-P2 immobilized on membrane strips in a protein overlay assay as described in the Examples. (D) Recombinant C2 domain (10 nM) was coated onto Copper chelate (His-Tag) YSi SPA Scintillation Beads in the presence of 0.25% BSA. Beads were then incubated with 5 μCi of [3H]-AQX-MN100 and the bead associated radioactivity measured as described in the Examples. Data are expressed as mean+/−SEM and are representative of at least three independent experiments.
Figure 4:
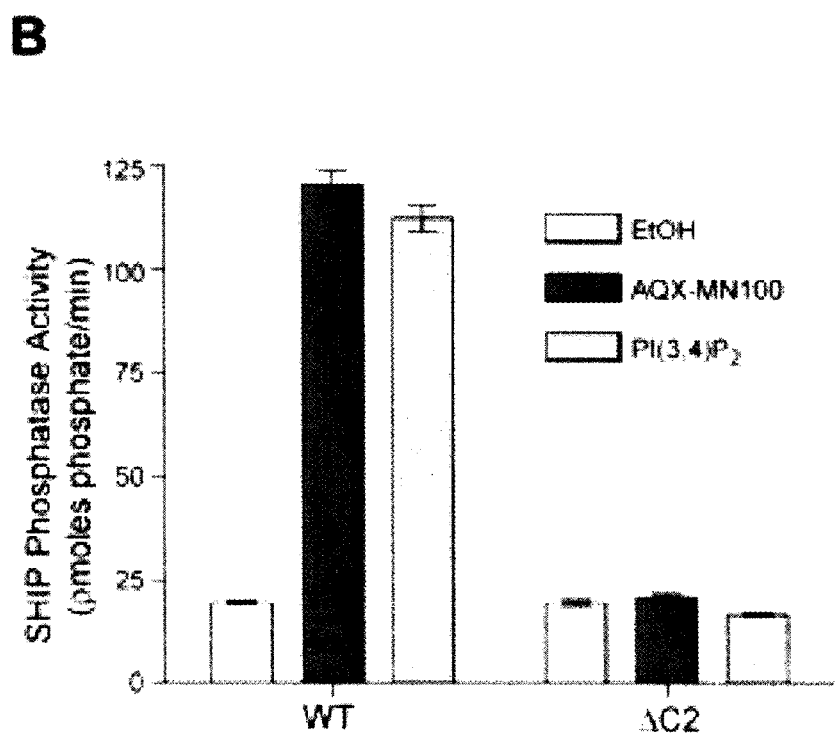
Figure 4:
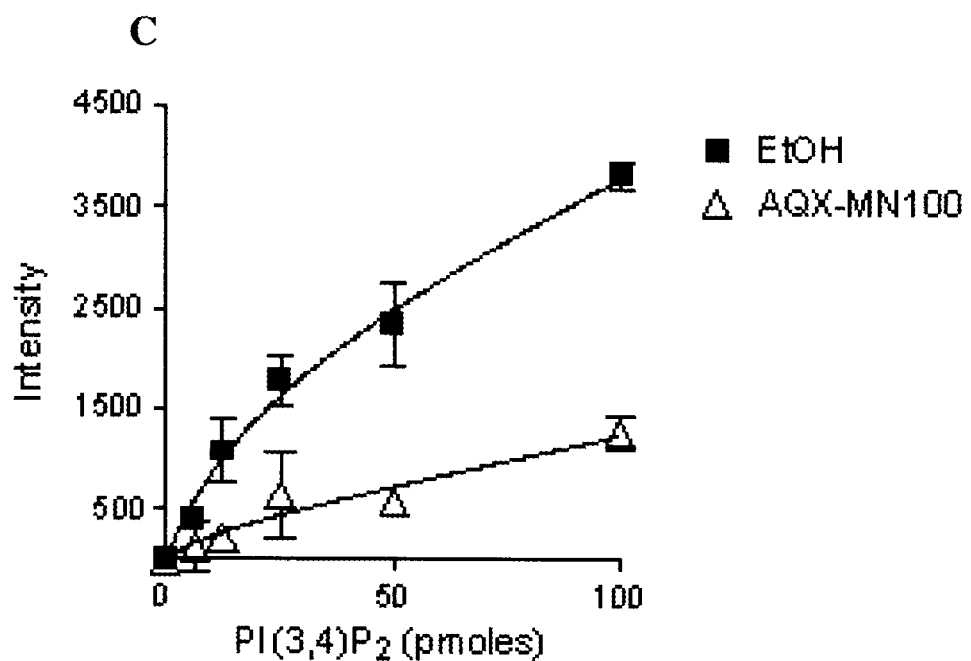
Figure 4:
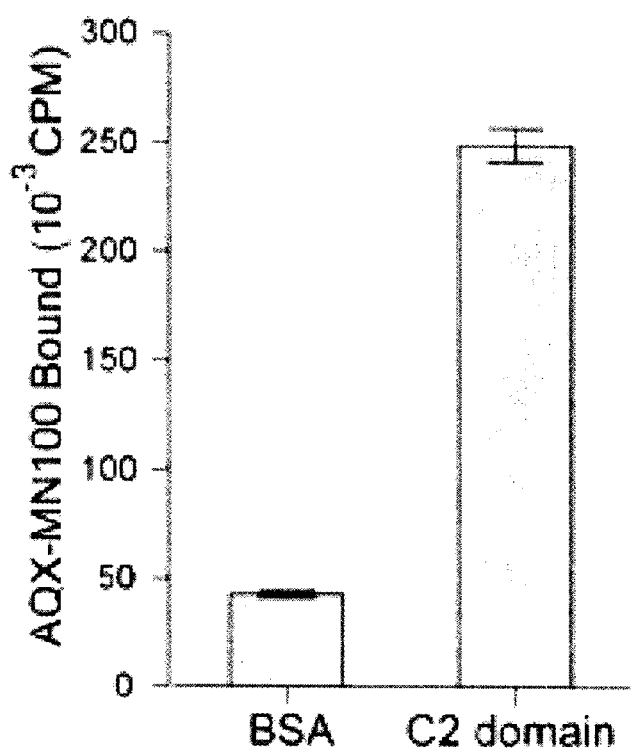

We then investigated the molecular mechanism by which AQX-MN100 activates SHIP1. We discovered through enzyme initial reaction velocity to analyses (12,13) that SHIP1 displays sigmoidal kinetics, indicating allosteric activation by its product PI-3,4-P2 (FIG. 4A). Indeed, the addition of PI-3,4-P2 to the enzyme reaction activated SHIP to the same extent as AQX-MN100 (FIG. 4B). SHIP1 contains a C2 domain (29) in its C-terminus. Internal deletion of the C2 domain impaired the ability of SHIP1 to be activated by either PI-3,4-P2 or AQX-MN100 (FIG. 4B). We also found that although AQX-MN100 is structurally very different from PI-3,4-P2, it could compete with PI-3,4-P2 for binding to SHIP's C2 domain (FIG. 4C), and, using [3H]-AQX-MN100, we confirmed that AQX-MN100 could directly bind to SHIP1's C2 domain (FIG. 4D). In complementary studies, we further observed that [3H]-AQX-MN100 binds to wild-type SHIP1 but not to SHIP1 lacking its C2 domain (FIG. 7). Together, these studies suggest that AQX-MN100 activates SHIP1 through binding to SHIP's C2 domain and this binding allosterically activates SHIP1. Additionally, AQX-MN100 selectively enhanced SHIP1 enzyme activity by almost 500% while having very little activity on a panel of 100 kinases and phosphatases (FIGS. 8A-B).

EXAMPLE 2

SHIP1 enzyme exhibits end-product allosteric regulation (FIG. 9). Non-allosterically regulated enzymes exhibit Michaelis-Menton hyperbolic enzyme reaction rate kinetics. Enzymes which are allosterically activated by their end-product (positive feedback) exhibit sigmoidal shaped enzyme kinetic curves as shown in FIG. 9A. The initial reaction velocity for SHIP1 phosphatase was determined (FIG. 4A). The initial reaction velocity for SHIP1 phosphatase was determined at the indicated inositol-1,3,4,5-tetrakisphosphate (IP4) concentration. (Each data point represents the initial slope of the line plotting enzyme activities over 20 min at each indicated substrate concentration.) Non-linear regression analyses determined the best fit to be a sigmoidal curve, indicating SHIP1 undergoes end-product allosteric activation.

The C2 domain of SHIP1 is required for allosteric activation by AQX-MN100 (FIG. 10). Full length, wild-type SHIP1 enzyme (wt) or SHIP1 enzyme in which the PH or C2 domains were deleted were tested for their ability to be activated by AQX-MN100. Deletion of the C2 domain abrogates the ability of SHIP1 to be activated by AQX-MN100. Interestingly, deletion of the PH domain attenuates but does not prevent the ability of SHIP1 to be activated by AQX-MN100. These data suggest that the C2 domain is required, but that the PH domain may contribute to allosteric activation.

SHIP1 protein requires the C2 domain to bind to AQX-MN100 (FIG. 13). Purified, recombinant SHIP1 enzyme and the C2 deletion mutant constructs as shown in FIG. 11A were bound to SPA (scintillation proximity assay) beads. [3H]-AQX-MN100 was added and the amount of SHIP1 bound AQX-MN100 was quantified by scintillation counting. These data show that the presence of the C2 domain is required for SHIP1 to bind to AQX-MN100. Deletion of the PH domain also attenuates the ability of SHIP1 to bind AQX-MN100.

However, AQX-MN100 inhibits the binding of the C2 but not the PH domain to phosphatidylinositol lipid (PIP2 and PIP3) (FIG. 12). Purified, recombinant HIS6 tagged SHIP1 PH or C2 domains were incubated with AQX-MN100 or vehicle (EtOH) control for 30 min prior to incubation with membrane strips spotted with a dilution series of PIP2 or PIP3. The amount of PH or C2 domain bound to each spot was visualized with anti-HIS6 antibody followed by Alexa 660 conjugated secondary antibody, quantified on a Li-Cor Odyssey scanner and expressed in arbitrary units. The PH domain binds PIP3>PIP2, whereas the C2 domain binds PIP2>PIP3. Only the C2 binding to PIP2/PIP3 could be inhibited by AQX-MN100. These data suggest that the binding of the small molecule SHIP1 activator, AQX-MN100 to the C2 domain involves contact residues in the C2 domain which participate in the binding of the natural activator PIP2.

The protein lipid overlay assay data suggesting AQX-MN100 does not interfere with PH domain binding of PIP2/PIP3 are consistent with scintillation proximity assay data showing recombinant C2 but not PH domain being able to bind [$^3$H]-AQX-MN100 (FIG. 15B). Recombinant PH or C2 domain were coated onto Copper chelate (His-Tag) YSi SPA Scintillation Beads in the presence of 0.25% BSA. Beads were then incubated with 5 µCi of [3H]-AQX-MN100 and the bead associated radioactivity measured by scintillation counting. The C2 reproducibly observed to bound [$^3$H]-AQX-MN100 whereas the PH domain did not do so consistently (FIG. 15B).

EXAMPLE 3

Despite the PH domain not being observed to reproducibly bind AQX-MN100, it is still involved in the process of allosteric regulation of SHIP1 activity.

Purified, recombinant wild-type (WT) SHIP, C2 (ΔC2) or PH (ΔC2) domain deletion SHIP mutants were tested in the in vitro SHIP enzyme assay for their ability to be activated by PI(3,4)P$_2$ and AQX-MN100. Although all three proteins possessed basal SHIP phosphatase activity in the presence of the EtOH vehicle control, only the activity of the wild-type enzyme was enhanced by the allosteric activators PI(3,4)P$_2$ and AQX-MN100. Thus, deletion of either the C2 or PH domain abrogates ability to be activated by PI(3,4)P$_2$ and AQX-MN100 (FIG. 15A).

References

1. Yang, L. et al. Synthesis of Pelorol and Analogues: Activators of the Inositol 5Phosphatase SHIP. Org Lett 7, 1073-1076 (2005).
2. Sly, L. M., Rauh, M. J., Kalesnikoff, J., Song, C. H. & Krystal, G. LPS-induced upregulation of SHIP is essential for endotoxin tolerance. Immunity 21, 227-39 (2004).
3. Huber, M. et al. The src homology 2-containing inositol phosphatase (SHIP) is the gatekeeper of mast cell degranulation. Proc Natl Acad Sci USA 95, 11330-5 (1998).
4. Huber, M., Kalesnikoff, J., Reth, M. & Krystal, G. The role of SHIP in mast cell degranulation and IgE-induced mast cell survival. Immunol Lett 82, 17-21 (2002).
5. Kalesnikoff, J. et al. SHIP negatively regulates IgE+antigen-induced IL-6 production in mast cells by inhibiting NF-kappa B activity. J Immunol 168, 4737-46 (2002).
6. Kemp, S. F. & Lockey, R. F. Anaphylaxis: a review of causes and mechanisms. J Allergy Clin Immunol 110, 341-8 (2002).
7. Kitaura, J. et al. Akt-dependent cytokine production in mast cells. J Exp Med 192, 729-40 (2000).
8. Djouder, N. et al. Rac and phosphatidylinositol 3-kinase regulate the protein kinase B in Fc epsilon R1 signaling in RBL 2H3 mast cells. J Immunol 166, 1627-34 (2001).
9. Galanos, C. & Freudenberg, M. A. Mechanisms of endotoxin shock and endotoxin hypersensitivity. Immunobiology 187, 346-56 (1993).
10. Young, J. M. et al. The mouse ear inflammatory response to topical arachidonic acid. J Invest Dermatol 82, 367-71 (1984).

11. Bindoli, A., Rigobello, M. P. & Deeble, D. J. Biochemical and toxicological properties of the oxidation products of catecholamines. Free Radic Biol Med 13, 391-405 (1992).
12. Campbell, R. B., Liu, F. & Ross, A. H. Allosteric activation of PTEN phosphatase by phosphatidylinositol 4,5-bisphosphate. J Biol Chem 278, 33617-20 (2003).
13. Schaletzky, J. et al. Phosphatidylinositol-5-phosphate activation and conserved substrate specificity of the myotubularin phosphatidylinositol 3-phosphatases. Curr Biol 13, 504-9 (2003).
14. Damen, J. E. et al. The 145-kDa protein induced to associate with Shc by multiple cytokines is an inositol tetraphosphate and phosphatidylinositol 3,4,5-triphosphate 5phosphatase. Proc Natl Acad Sci USA 93, 1689-93 (1996).
15. Ng, D. H. W., Harder, K. W., Clark-Lewis, I., Jirik, F. & Johnson, P. Non-radioactive method to measure CD45 protein tyrosine phosphatase activity isolated directly from cells. Journal of Immunological Methods 179, 177-185 (1995).
16. Krahn, A. K., Ma, K., Hou, S., Duronio, V. & Marshall, A. J. Two distinct waves of membrane-proximal B cell antigen receptor signaling differentially regulated by Src homology 2-containing inositol polyphosphate 5-phosphatase. J Immunol 172, 331-9 (2004).
17. Huber, M. et al. The src homology 2-containing inositol phosphatase (SHIP) is the gatekeeper of mast cell degranulation. Proc Natl Acad Sci USA 95, 11330-5 (1998).
18. Sly, L. M., Rauh, M. J., Kalesnikoff, J., Song, C. H. & Krystal, G. LPS-induced upregulation of SHIP is essential for endotoxin tolerance. Immunity 21, 227-39 (2004).
19. Huber, M., Kalesnikoff, J., Reth, M. & Krystal, G. The role of SHIP in mast cell degranulation and IgE-induced mast cell survival. Immunol Lett 82, 17-21 (2002).
20. Kalesnikoff, J. et al. SHIP negatively regulates IgE+antigen-induced IL-6 production in mast cells by inhibiting NF-kappa B activity. J Immunol 168, 4737-46 (2002).
21. Young, J. M. et al. The mouse ear inflammatory response to topical arachidonic acid. J Invest Dermatol 82, 367-71 (1984).
22. Hyun, E. et al. Anti-inflammatory effects of nitric oxide-releasing hydrocortisone NCX 1022, in a murine model of contact dermatitis. Br J Pharmacol 143, 618-25 (2004).
23. Dowler, S., Kular, G. & Alessi, D. R. Protein lipid overlay assay. Sci STKE 2002, PL6 (2002).
24. Lucas, D. M. and Rohrschneider, L. R. Blood 93, 1922-1933 (1999).
25. Wolf, I., Lucas, D. M., Algate, P. A. and Rohrschneider, L. R. Genomics 69, 104-112 (2000).
26. Damen, J. E., Liu, L., Ware, M. D., Ermolaeva, M., Majerus, P. W. and Krystal, G. Blood 92, 1199-1205 (1998).
27. Tu, Z., Ninos, J. M., Ma, Z., Wang, J.-W., Lemos, M. P., Desporits, C., Ghansah T., Howson, J. M. and Kerr, W. G. Blood 98, 2028-2038 (2001).
28. Altschul, S. F. Amino acid substitution matrices from an information theoretic perspective. J Mol. Bio., 219: 555-665 (1991).
29. Dayhoff, M. O., Schwartz, R. M., Orcutt, B. C. A model of evolutionary change in proteins. Atlas of Protein Sequence and Structure. 5(3) M. O. Dayhoff (ed.), 345-352, National Biomedical Research Foundation, Washington (1978).
30. States, D. J., Gish, W., Altschul, S. F. Improved Sensitivity of Nucleic Acid Database Search Using Application-Specific Scoring Matrices. Methods: A companion to Methods in Enzymology 3(1): 66-77 (1991).
31. Henikoff, S. and Henikoff J. G. Amino acid substitution matrices from protein blocks. Proc. Natl. Acad. Sci. USA. 89(biochemistry): 10915-10919 (1992).
32. Johnson M. S. and Overington J. P. A Structural Basis of Sequence Comparisons: An evaluation of scoring methodologies. J Mol. Bio. 233: 716-738 (1993).
33. Henikoff, S. and Henikoff J. G. Performance Evaluation of Amino Acid Substitution Matrices. Proteins: Structure, Function, and Genetics. 17: 49-61 (1993).
34. Karlin, S. and Altschul, S. F. Methods for assessing the statistical significance of molecular sequence features by using general scoring schemes. Proc. Natl. Acad. Sci. USA. 87: 2264-2268 (1990).
35. Eisenberg et al. J. Mol. Bio. 179: 125-142, 184.
36. Sambrook et al. Molecular Cloning: A Laboratory Manual. $2^{nd}$ ed., Cold Spring Harbor Laboratory, Cold Spring Harbor Laboratory Press, Cold spring Harbor, N.Y. (1989).
37. Ausubel et al. Current Protocols in Molecular Biology, John Wiley & Sons (1994).
38. Gennaro, A. Remington: the Science & Practice of Pharmacy. $20^{th}$ ed., Williams & Wilkins (2000).

All citations are hereby incorporated by reference.

The present invention has been described with regard to one or more embodiments. However, it will be apparent to persons skilled in the art that a number of variations and modifications can be made without departing from the scope of the invention as defined in the claims. The terms "a," "an" and "the" as used herein are defined to mean "one or more" and include the plural unless the context is inappropriate.

What is claimed is:

1. A method of identifying an allosteric modulator of a SH2-containing inositol-5'-phosphatase (SHIP) polypeptide, the method comprising:
 a) providing a SHIP polypeptide, or fragment or variant thereof, wherein the SHIP polypeptide or the fragment or variant thereof comprises an allosteric site that comprises a SHIP C2 domain and a SHIP pleckstrin homology (PH) domain;
 b) contacting the SHIP polypeptide, or the fragment or variant thereof, with a test compound; and
 c) determining whether the test compound specifically binds the allosteric site, wherein the test compound is determined to be an allosteric modulator of the SHIP polypeptide if the test compound specifically binds the allosteric site.

2. The method of claim 1 wherein the C2 domain comprises one or more of SEQ ID NOs: 16-34.

3. The method of claim 1 wherein the PH domain comprises one or more of SEQ ID NOs: 4-15, 35, and 36.

4. The method of claim 1 wherein the SHIP polypeptide comprises SEQ ID NO:1, 2, 50 or 51.

5. The method of claim 1 wherein the SHIP polypeptide, or the fragment or variant thereof, is catalytically inactive.

6. The method of claim 1 wherein the allosteric modulator is an activator of the SHIP polypeptide.

7. The method of claim 1 wherein the allosteric modulator is an inhibitor of the SHIP polypeptide.

8. The method of claim 1 wherein the test compound is one or more of an antibody, a peptide, a protein, an oligonucleotide, and a small molecule.

9. The method of claim 1 wherein the SHIP polypeptide is one or more of SHIP1, SHIP2, and stem cell SHIP.

10. The method of claim 1 further comprising determining whether the test compound modulates an activity of the SHIP polypeptide or the fragment or variant thereof.

11. The method of claim 10 wherein the activity of the SHIP polypeptide, or the fragment or variant thereof, comprises modulation of a level of a SHIP substrate, modulation of a level of a SHIP product, or binding to a SHIP-associated protein.

12. The method of claim 1, further comprising determining whether the test compound binds a second SHIP polypeptide, or second fragment or variant thereof, lacking an allosteric site.

13. A method of identifying an allosteric modulator of a SH2-containing inositol -5'-phosphatase (SHIP) polypeptide, the method comprising:
 a) providing a SHIP polypeptide, or fragment or variant thereof, wherein the SHIP polypeptide or the fragment or variant thereof comprises an allosteric site that comprises a SHIP C2 domain and a SHIP pleckstrin homology (PH) domain;
 b) contacting the SHIP polypeptide, or the fragment or variant thereof, with a test compound; and
 c) determining whether the test compound allosterically modulates an activity or levels of the SHIP polypeptide, or the fragment or variant thereof,
 wherein the test compound is determined to be an allosteric modulator of the SHIP polypeptide if the test compound allosterically modulates the activity or levels of the SHIP polypeptide, or the fragment or variant thereof.

14. The method of claim 13 further comprising determining whether the test compound specifically binds the allosteric site of the SHIP polypeptide, or the fragment or variant thereof.

15. The method of claim 13 further comprising, prior to (c), providing a control compound and determining whether the test compound allosterically modulates the activity or levels of the SHIP polypeptide, or the fragment or variant thereof, relative to the control compound.

16. The method of claim 13 wherein the C2 domain comprises one or more of SEQ ID NOs:16-34.

17. The method of claim 13 wherein the PH domain comprises one or more of SEQ ID NOs:4-15, 35, and 36.

18. The method of claim 13 wherein the SHIP polypeptide comprises SEQ ID NO:1, 2, 50 or 51.

19. The method of claim 13 further comprising:
 a) providing a second SHIP polypeptide, or second fragment or variant thereof, lacking an allosteric site, wherein the allosteric site is a SHIP C2 domain or a SHIP pleckstrin homology (PH) domain;
 b) contacting the second SHIP polypeptide, or the second fragment or variant thereof, lacking the allosteric site with the test compound; and
 c) determining whether the test compound allosterically modulates an activity or levels of the second SHIP polypeptide, or the second fragment or variant thereof, lacking the allosteric site;
 wherein the test compound is determined to be an allosteric modulator of the SHIP polypeptide if the test compound does not allosterically modulate the activity or levels of the second SHIP polypeptide, or the second fragment or variant thereof, lacking the allosteric site.

20. The method of claim 13 wherein the allosteric modulator is an activator of the SHIP polypeptide.

21. The method of claim 13 wherein the allosteric modulator is an inhibitor of the SHIP polypeptide.

22. The method of claim 13 wherein the test compound is one or more of an antibody, a peptide, a protein, an oligonucleotide, and a small molecule.

23. The method of claim 13 wherein the SHIP polypeptide is one or more of SHIP1, SHIP2, and stem cell SHIP.

24. A method of identifying an allosteric modulator of a SH2-containing inositol-5'-phosphatase (SHIP) polypeptide, the method comprising:
 a) providing a SHIP polypeptide, or fragment or variant thereof, wherein the SHIP polypeptide or the fragment or variant thereof comprises an allosteric site that comprises a SHIP C2 domain and a SHIP pleckstrin homology (PH) domain;
 b) contacting the SHIP polypeptide, or the fragment or variant thereof, with a test compound;
 c) contacting the SHIP polypeptide, or the fragment or variant thereof, with a control compound that binds the allosteric site or allosterically modulates an activity or levels of the SHIP polypeptide, or the fragment or variant thereof; and
 d) determining whether the test compound interferes with binding of the control compound to the allosteric site, or interferes with allosteric modulation of the activity or levels of the SHIP polypeptide, or the fragment or variant thereof, by the control compound,
 wherein the test compound is determined to be an allosteric modulator of the SHIP polypeptide if the test compound interferes with the binding of the control compound or the allosteric modulation by the control compound.

25. The method of claim 24 wherein the control compound is AQX-016A or AQX-MN100.

26. A method of identifying an allosteric modulator of a SH2-containing inositol-5'-phosphatase (SHIP) polypeptide, the method comprising:
 a) providing a first SHIP polypeptide, or first fragment or variant thereof, wherein the first SHIP polypeptide or the first fragment or variant thereof comprises an allosteric site that comprises a SHIP C2 domain and a SHIP pleckstrin homology (PH) domain, and providing a second SHIP polypeptide, or second fragment or variant thereof, lacking an allosteric site;
 b) contacting the first SHIP polypeptide, or the first fragment or variant thereof, and contacting the second SHIP polypeptide, or the second fragment or variant thereof, with a test compound;
 c) determining whether the test compound allosterically modulates an activity or levels of the first SHIP polypeptide, or the first fragment or variant thereof; and
 d) determining whether the test compound allosterically modulates an activity or levels of the second SHIP polypeptide, or the second fragment or variant thereof,
 wherein the test compound is determined to be an allosteric modulator if the test compound allosterically modulates an activity or levels of the first SHIP polypeptide, or the first fragment or variant thereof, and does not allosterically modulates an activity or levels of the second SHIP polypeptide, or the second fragment or variant thereof.

27. The method of claim 26 wherein the C2 domain comprises one or more of SEQ ID NOs:16-34.

28. The method of claim 26 wherein the PH domain comprises one or more of SEQ ID NOs:4-15, 35, and 36.

29. The method of claim 26 wherein the first SHIP polypeptide comprises SEQ ID NO:1, 2, 50 or 51.

30. The method of claim 26 wherein the first SHIP polypeptide, or the first fragment or variant thereof, is catalytically inactive.

31. The method of claim 26 wherein the allosteric modulator is an activator of the first SHIP polypeptide.

32. The method of claim 26 wherein the allosteric modulator is an inhibitor of the first SHIP polypeptide.

33. The method of claim 26 wherein the test compound is one or more of an antibody, a peptide, a protein, an oligonucleotide, and a small molecule.

34. The method of claim 26 wherein the first SHIP polypeptide is one or more of SHIP1, SHIP2, and stem cell SHIP.

35. The method of claim 26 further comprising determining whether the test compound modulates an activity of the first SHIP polypeptide, or the first fragment or variant thereof.

36. The method of claim 26 wherein the second SHIP polypeptide or the second fragment or variant thereof lacks the C2 domain.

37. The method of claim 26 wherein the second SHIP polypeptide or the second fragment or variant thereof lacks the PH domain.

* * * * *

SEQUENCE LISTING

```
<160> NUMBER OF SEQ ID NOS: 51

<210> SEQ ID NO 1
<211> LENGTH: 1188
<212> TYPE: PRT
<213> ORGANISM: Homo sapiens

<400> SEQUENCE: 1

Met Val Pro Cys Trp Asn His Gly Asn Ile Thr Arg Ser Lys Ala Glu
1               5                   10                  15

Glu Leu Leu Ser Arg Thr Gly Lys Asp Gly Ser Phe Leu Val Arg Ala
            20                  25                  30

Ser Glu Ser Ile Ser Arg Ala Tyr Ala Leu Cys Val Leu Tyr Arg Asn
        35                  40                  45
```

```
Cys Val Tyr Thr Tyr Arg Ile Leu Pro Asn Glu Asp Asp Lys Phe Thr
     50                  55                  60

Val Gln Ala Ser Glu Gly Val Ser Met Arg Phe Thr Lys Leu Asp
 65                  70                  75                  80

Gln Leu Ile Glu Phe Tyr Lys Lys Glu Asn Met Gly Leu Val Thr His
                     85                  90                  95

Leu Gln Tyr Pro Val Pro Leu Glu Glu Asp Thr Gly Asp Asp Pro
                100                 105                 110

Glu Glu Asp Thr Glu Ser Val Val Ser Pro Pro Glu Leu Pro Pro Arg
                115                 120                 125

Asn Ile Pro Leu Thr Ala Ser Ser Cys Glu Ala Lys Glu Val Pro Phe
    130                 135                 140

Ser Asn Glu Asn Pro Arg Ala Thr Glu Thr Ser Arg Pro Ser Leu Ser
145                 150                 155                 160

Glu Thr Leu Phe Gln Arg Leu Gln Ser Met Asp Thr Ser Gly Leu Pro
                165                 170                 175

Glu Glu His Leu Lys Ala Ile Gln Asp Tyr Leu Ser Thr Gln Leu Ala
                180                 185                 190

Gln Asp Ser Glu Phe Val Lys Thr Gly Ser Ser Ser Leu Pro His Leu
    195                 200                 205

Lys Lys Leu Thr Thr Leu Leu Cys Lys Glu Leu Tyr Gly Glu Val Ile
    210                 215                 220

Arg Thr Leu Pro Ser Leu Glu Ser Leu Gln Arg Leu Phe Asp Gln Gln
225                 230                 235                 240

Leu Ser Pro Gly Leu Arg Pro Arg Pro Gln Val Pro Gly Glu Ala Asn
                245                 250                 255

Pro Ile Asn Met Val Ser Lys Leu Ser Gln Leu Thr Ser Leu Leu Ser
            260                 265                 270

Ser Ile Glu Asp Lys Val Lys Ala Leu Leu His Glu Gly Pro Glu Ser
    275                 280                 285

Pro His Arg Pro Ser Leu Ile Pro Pro Val Thr Phe Glu Val Lys Ala
    290                 295                 300

Glu Ser Leu Gly Ile Pro Gln Lys Met Gln Leu Lys Val Asp Val Glu
305                 310                 315                 320

Ser Gly Lys Leu Ile Ile Lys Lys Ser Lys Asp Gly Ser Glu Asp Lys
                325                 330                 335

Phe Tyr Ser His Lys Lys Ile Leu Gln Leu Ile Lys Ser Gln Lys Phe
            340                 345                 350

Leu Asn Lys Leu Val Ile Leu Val Glu Thr Glu Lys Glu Lys Ile Leu
    355                 360                 365

Arg Lys Glu Tyr Val Phe Ala Asp Ser Lys Lys Arg Glu Gly Phe Cys
370                 375                 380

Gln Leu Leu Gln Gln Met Lys Asn Lys His Ser Glu Gln Pro Glu Pro
385                 390                 395                 400

Asp Met Ile Thr Ile Phe Ile Gly Thr Trp Asn Met Gly Asn Ala Pro
                405                 410                 415

Pro Pro Lys Lys Ile Thr Ser Trp Phe Leu Ser Lys Gly Gln Gly Lys
                420                 425                 430

Thr Arg Asp Asp Ser Ala Asp Tyr Ile Pro His Asp Ile Tyr Val Ile
                435                 440                 445

Gly Thr Gln Glu Asp Pro Leu Ser Glu Lys Glu Trp Leu Glu Ile Leu
    450                 455                 460
```

-continued

```
Lys His Ser Leu Gln Glu Ile Thr Ser Val Thr Phe Lys Thr Val Ala
465                 470                 475                 480

Ile His Thr Leu Trp Asn Ile Arg Ile Val Val Leu Ala Lys Pro Glu
                485                 490                 495

His Glu Asn Arg Ile Ser His Ile Cys Thr Asp Asn Val Lys Thr Gly
            500                 505                 510

Ile Ala Asn Thr Leu Gly Asn Lys Gly Ala Val Gly Val Ser Phe Met
        515                 520                 525

Phe Asn Gly Thr Ser Leu Gly Phe Val Asn Ser His Leu Thr Ser Gly
    530                 535                 540

Ser Glu Lys Lys Leu Arg Arg Asn Gln Asn Tyr Met Asn Ile Leu Arg
545                 550                 555                 560

Phe Leu Ala Leu Gly Asp Lys Lys Leu Ser Pro Phe Asn Ile Thr His
                565                 570                 575

Arg Phe Thr His Leu Phe Trp Phe Gly Asp Leu Asn Tyr Arg Val Asp
            580                 585                 590

Leu Pro Thr Trp Glu Ala Glu Thr Ile Ile Gln Lys Ile Lys Gln Gln
        595                 600                 605

Gln Tyr Ala Asp Leu Leu Ser His Asp Gln Leu Leu Thr Glu Arg Arg
    610                 615                 620

Glu Gln Lys Val Phe Leu His Phe Glu Glu Glu Ile Thr Phe Ala
625                 630                 635                 640

Pro Thr Tyr Arg Phe Glu Arg Leu Thr Arg Asp Lys Tyr Ala Tyr Thr
                645                 650                 655

Lys Gln Lys Ala Thr Gly Met Lys Tyr Asn Leu Pro Ser Trp Cys Asp
            660                 665                 670

Arg Val Leu Trp Lys Ser Tyr Pro Leu Val His Val Val Cys Gln Ser
        675                 680                 685

Tyr Gly Ser Thr Ser Asp Ile Met Thr Ser Asp His Ser Pro Val Phe
    690                 695                 700

Ala Thr Phe Glu Ala Gly Val Thr Ser Gln Phe Val Ser Lys Asn Gly
705                 710                 715                 720

Pro Gly Thr Val Asp Ser Gln Gly Gln Ile Glu Phe Leu Arg Cys Tyr
                725                 730                 735

Ala Thr Leu Lys Thr Lys Ser Gln Thr Lys Phe Tyr Leu Glu Phe His
            740                 745                 750

Ser Ser Cys Leu Glu Ser Phe Val Lys Ser Gln Glu Gly Glu Asn Glu
        755                 760                 765

Glu Gly Ser Glu Gly Glu Leu Val Val Lys Phe Gly Glu Thr Leu Pro
    770                 775                 780

Lys Leu Lys Pro Ile Ile Ser Asp Pro Glu Tyr Leu Leu Asp Gln His
785                 790                 795                 800

Ile Leu Ile Ser Ile Lys Ser Ser Asp Ser Asp Glu Ser Tyr Gly Glu
                805                 810                 815

Gly Cys Ile Ala Leu Arg Leu Glu Ala Thr Glu Thr Gln Leu Pro Ile
            820                 825                 830

Tyr Thr Pro Leu Thr His His Gly Glu Leu Thr Gly His Phe Gln Gly
        835                 840                 845

Glu Ile Lys Leu Gln Thr Ser Gln Gly Lys Thr Arg Glu Lys Leu Tyr
    850                 855                 860

Asp Phe Val Lys Thr Glu Arg Asp Glu Ser Ser Gly Pro Lys Thr Leu
865                 870                 875                 880

Lys Ser Leu Thr Ser His Asp Pro Met Lys Gln Trp Glu Val Thr Ser
```

```
                885                 890                 895
Arg Ala Pro Pro Cys Ser Gly Ser Ser Ile Thr Glu Ile Ile Asn Pro
                    900                 905                 910

Asn Tyr Met Gly Val Gly Pro Phe Gly Pro Met Pro Leu His Val
            915                 920                 925

Lys Gln Thr Leu Ser Pro Asp Gln Gln Pro Thr Ala Trp Ser Tyr Asp
        930                 935                 940

Gln Pro Pro Lys Asp Ser Pro Leu Gly Pro Cys Arg Gly Glu Ser Pro
945                 950                 955                 960

Pro Thr Pro Pro Gly Gln Pro Pro Ile Ser Pro Lys Lys Phe Leu Pro
                965                 970                 975

Ser Thr Ala Asn Arg Gly Leu Pro Pro Arg Thr Gln Glu Ser Arg Pro
            980                 985                 990

Ser Asp Leu Gly Lys Asn Ala Gly Asp Thr Leu Pro Gln Glu Asp Leu
        995                 1000                1005

Pro Leu Thr Lys Pro Glu Met Phe Glu Asn Pro Leu Tyr Gly Ser
    1010                1015                1020

Leu Ser Ser Phe Pro Lys Pro Ala Pro Arg Lys Asp Gln Glu Ser
    1025                1030                1035

Pro Lys Met Pro Arg Lys Glu Pro Pro Cys Pro Glu Pro Gly
    1040                1045                1050

Ile Leu Ser Pro Ser Ile Val Leu Thr Lys Ala Gln Glu Ala Asp
    1055                1060                1065

Arg Gly Glu Gly Pro Gly Lys Gln Val Pro Ala Pro Arg Leu Arg
    1070                1075                1080

Ser Phe Thr Cys Ser Ser Ser Ala Glu Gly Arg Ala Ala Gly Gly
    1085                1090                1095

Asp Lys Ser Gln Gly Lys Pro Lys Thr Pro Val Ser Ser Gln Ala
    1100                1105                1110

Pro Val Pro Ala Lys Arg Pro Ile Lys Pro Ser Arg Ser Glu Ile
    1115                1120                1125

Asn Gln Gln Thr Pro Pro Pro Thr Pro Arg Pro Pro Leu Pro
    1130                1135                1140

Val Lys Ser Pro Ala Val Leu His Leu Gln His Ser Lys Gly Arg
    1145                1150                1155

Asp Tyr Arg Asp Asn Thr Glu Leu Pro His His Gly Lys His Arg
    1160                1165                1170

Pro Glu Glu Gly Pro Pro Gly Pro Leu Gly Arg Thr Ala Met Gln
    1175                1180                1185

<210> SEQ ID NO 2
<211> LENGTH: 1187
<212> TYPE: PRT
<213> ORGANISM: Mus musculus

<400> SEQUENCE: 2

Met Val Pro Gly Trp Asn His Gly Asn Ile Thr Arg Ser Lys Ala Glu
1               5                   10                  15

Glu Leu Leu Ser Arg Ala Gly Lys Asp Gly Ser Phe Leu Val Arg Ala
            20                  25                  30

Ser Glu Ser Ile Pro Arg Ala Cys Ala Leu Cys Val Leu Phe Arg Asn
        35                  40                  45

Cys Val Tyr Thr Tyr Arg Ile Leu Pro Asn Glu Asp Asp Lys Phe Thr
    50                  55                  60
```

```
Val Gln Ala Ser Glu Gly Val Pro Met Arg Phe Thr Lys Leu Asp
 65              70                  75                  80

Gln Leu Ile Asp Phe Tyr Lys Lys Glu Asn Met Gly Leu Val Thr His
             85                  90                  95

Leu Gln Tyr Pro Val Pro Leu Glu Glu Asp Ala Ile Asp Glu Ala
            100                 105                 110

Glu Glu Asp Thr Glu Ser Val Met Ser Pro Glu Leu Pro Pro Arg
            115                 120                 125

Asn Ile Pro Met Ser Ala Gly Pro Ser Glu Ala Lys Asp Leu Pro Leu
    130                 135                 140

Ala Thr Glu Asn Pro Arg Ala Pro Glu Val Thr Arg Leu Ser Leu Ser
145                 150                 155                 160

Glu Thr Leu Phe Gln Arg Leu Gln Ser Met Asp Thr Ser Gly Leu Pro
            165                 170                 175

Glu Glu His Leu Lys Ala Ile Gln Asp Tyr Leu Ser Thr Gln Leu Leu
            180                 185                 190

Leu Asp Ser Asp Phe Leu Lys Thr Gly Ser Ser Asn Leu Pro His Leu
        195                 200                 205

Lys Lys Leu Met Ser Leu Leu Cys Lys Glu Leu His Gly Glu Val Ile
    210                 215                 220

Arg Thr Leu Pro Ser Leu Glu Ser Leu Gln Arg Leu Phe Asp Gln Gln
225                 230                 235                 240

Leu Ser Pro Gly Leu Arg Pro Arg Pro Gln Val Pro Gly Glu Ala Ser
                245                 250                 255

Pro Ile Thr Met Val Ala Lys Leu Ser Gln Leu Thr Ser Leu Leu Ser
            260                 265                 270

Ser Ile Glu Asp Lys Val Lys Ser Leu Leu His Glu Gly Ser Glu Ser
        275                 280                 285

Thr Asn Arg Arg Ser Leu Ile Pro Pro Val Thr Phe Glu Val Lys Ser
    290                 295                 300

Glu Ser Leu Gly Ile Pro Gln Lys Met His Leu Lys Val Asp Val Glu
305                 310                 315                 320

Ser Gly Lys Leu Ile Val Lys Lys Ser Lys Asp Gly Ser Glu Asp Lys
                325                 330                 335

Phe Tyr Ser His Lys Lys Ile Leu Gln Leu Ile Lys Ser Gln Lys Phe
            340                 345                 350

Leu Asn Lys Leu Val Ile Leu Val Glu Thr Glu Lys Glu Lys Ile Leu
        355                 360                 365

Arg Lys Glu Tyr Val Phe Ala Asp Ser Lys Lys Arg Glu Gly Phe Cys
370                 375                 380

Gln Leu Leu Gln Gln Met Lys Asn Lys His Ser Glu Gln Pro Glu Pro
385                 390                 395                 400

Asp Met Ile Thr Ile Phe Ile Gly Thr Trp Asn Met Gly Asn Ala Pro
            405                 410                 415

Pro Pro Lys Lys Ile Thr Ser Trp Phe Leu Ser Lys Gly Gln Gly Lys
                420                 425                 430

Thr Arg Asp Asp Ser Ala Asp Tyr Ile Pro His Asp Ile Tyr Val Ile
            435                 440                 445

Gly Thr Gln Glu Asp Pro Leu Gly Glu Lys Glu Trp Leu Glu Leu Leu
            450                 455                 460

Arg His Ser Leu Gln Glu Val Thr Ser Met Thr Phe Lys Thr Val Ala
465                 470                 475                 480

Ile His Thr Leu Trp Asn Ile Arg Ile Val Val Leu Ala Lys Pro Glu
```

```
              485                 490                 495
His Glu Asn Arg Ile Ser His Ile Cys Thr Asp Asn Val Lys Thr Gly
                500                 505                 510
Ile Ala Asn Thr Leu Gly Asn Lys Gly Ala Val Gly Val Ser Phe Met
                515                 520                 525
Phe Asn Gly Thr Ser Leu Gly Phe Val Asn Ser His Leu Thr Ser Gly
                530                 535                 540
Ser Glu Lys Lys Leu Arg Arg Asn Gln Asn Tyr Met Asn Ile Leu Arg
545                 550                 555                 560
Phe Leu Ala Leu Gly Asp Lys Lys Leu Ser Pro Phe Asn Ile Thr His
                565                 570                 575
Arg Phe Thr His Leu Phe Trp Leu Gly Asp Leu Asn Tyr Arg Val Glu
                580                 585                 590
Leu Pro Thr Trp Glu Ala Glu Ala Ile Ile Gln Lys Ile Lys Gln Gln
                595                 600                 605
Gln Tyr Ser Asp Leu Leu Ala His Asp Gln Leu Leu Leu Glu Arg Lys
                610                 615                 620
Asp Gln Lys Val Phe Leu His Phe Glu Glu Glu Ile Thr Phe Ala
625                 630                 635                 640
Pro Thr Tyr Arg Phe Glu Arg Leu Thr Arg Asp Lys Tyr Ala Tyr Thr
                645                 650                 655
Lys Gln Lys Ala Thr Gly Met Lys Tyr Asn Leu Pro Ser Trp Cys Asp
                660                 665                 670
Arg Val Leu Trp Lys Ser Tyr Pro Leu Val His Val Cys Gln Ser
                675                 680                 685
Tyr Gly Ser Thr Ser Asp Ile Met Thr Ser Asp His Ser Pro Val Phe
                690                 695                 700
Ala Thr Phe Glu Ala Gly Val Thr Ser Gln Phe Val Ser Lys Asn Gly
705                 710                 715                 720
Pro Gly Thr Val Asp Ser Gln Gly Gln Ile Glu Phe Leu Ala Cys Tyr
                725                 730                 735
Ala Thr Leu Lys Thr Lys Ser Gln Thr Lys Phe Tyr Leu Glu Phe His
                740                 745                 750
Ser Ser Cys Leu Glu Ser Phe Val Lys Ser Gln Glu Gly Glu Asn Glu
                755                 760                 765
Glu Gly Ser Glu Gly Glu Leu Val Val Arg Phe Gly Glu Thr Leu Pro
770                 775                 780
Lys Leu Lys Pro Ile Ile Ser Asp Pro Glu Tyr Leu Leu Asp Gln His
785                 790                 795                 800
Ile Leu Ile Ser Ile Lys Ser Ser Asp Ser Asp Glu Ser Tyr Gly Glu
                805                 810                 815
Gly Cys Ile Ala Leu Arg Leu Glu Thr Thr Glu Ala Gln His Pro Ile
                820                 825                 830
Tyr Thr Pro Leu Thr His His Gly Glu Met Thr Gly His Phe Arg Gly
                835                 840                 845
Glu Ile Lys Leu Gln Thr Ser Gln Gly Lys Met Arg Glu Lys Leu Tyr
850                 855                 860
Asp Phe Val Lys Thr Glu Arg Asp Glu Ser Ser Gly Met Lys Cys Leu
865                 870                 875                 880
Lys Asn Leu Thr Ser His Asp Pro Met Arg Gln Trp Glu Pro Ser Gly
                885                 890                 895
Arg Val Pro Ala Cys Gly Val Ser Leu Asn Glu Met Ile Asn Pro
                900                 905                 910
```

```
Asn Tyr Ile Gly Met Gly Pro Phe Gly Gln Pro Leu His Gly Lys Ser
        915                 920                 925

Thr Leu Ser Pro Asp Gln Gln Leu Thr Ala Trp Ser Tyr Asp Gln Leu
    930                 935                 940

Pro Lys Asp Ser Ser Leu Gly Pro Gly Arg Gly Glu Gly Pro Pro Thr
945                 950                 955                 960

Pro Pro Ser Gln Pro Pro Leu Ser Pro Lys Lys Phe Ser Ser Thr
                965                 970                 975

Thr Asn Arg Gly Pro Cys Pro Arg Val Gln Glu Ala Arg Pro Gly Asp
            980                 985                 990

Leu Gly Lys Val Glu Ala Leu Leu Gln Glu Asp Leu Leu Leu Thr Lys
        995                 1000                1005

Pro Glu Met Phe Glu Asn Pro Leu Tyr Gly Ser Val Ser Ser Phe
    1010                1015                1020

Pro Lys Leu Val Pro Arg Lys Glu Gln Glu Ser Pro Lys Met Leu
    1025                1030                1035

Arg Lys Glu Pro Pro Pro Cys Pro Asp Pro Gly Ile Ser Ser Pro
    1040                1045                1050

Ser Ile Val Leu Pro Lys Ala Gln Glu Val Glu Ser Val Lys Gly
    1055                1060                1065

Thr Ser Lys Gln Ala Pro Val Pro Val Leu Gly Pro Thr Pro Arg
    1070                1075                1080

Ile Arg Ser Phe Thr Cys Ser Ser Ser Ala Glu Gly Arg Met Thr
    1085                1090                1095

Ser Gly Asp Lys Ser Gln Gly Lys Pro Lys Ala Ser Ala Ser Ser
    1100                1105                1110

Gln Ala Pro Val Pro Val Lys Arg Pro Val Lys Pro Ser Arg Ser
    1115                1120                1125

Glu Met Ser Gln Gln Thr Thr Pro Ile Pro Ala Pro Arg Pro Pro
    1130                1135                1140

Leu Pro Val Lys Ser Pro Ala Val Leu Gln Leu Gln His Ser Lys
    1145                1150                1155

Gly Arg Asp Tyr Arg Asp Asn Thr Glu Leu Pro His His Gly Lys
    1160                1165                1170

His Arg Gln Glu Glu Gly Leu Leu Gly Arg Thr Ala Met Gln
    1175                1180                1185

<210> SEQ ID NO 3
<211> LENGTH: 1040
<212> TYPE: PRT
<213> ORGANISM: Artificial
<220> FEATURE:
<223> OTHER INFORMATION: consensus sequence of human and mouse SHIP1

<400> SEQUENCE: 3

Met Val Pro Trp Asn His Gly Asn Ile Thr Arg Ser Lys Ala Glu Glu
1               5                   10                  15

Leu Leu Ser Arg Gly Lys Asp Gly Ser Phe Leu Val Arg Ala Ser Glu
            20                  25                  30

Ser Ile Arg Ala Ala Leu Cys Val Leu Arg Asn Cys Val Tyr Thr Tyr
        35                  40                  45

Arg Ile Leu Pro Asn Glu Asp Asp Lys Phe Thr Val Gln Ala Ser Glu
    50                  55                  60

Gly Val Met Arg Phe Phe Thr Lys Leu Asp Gln Leu Ile Phe Tyr Lys
65                  70                  75                  80
```

```
Lys Glu Asn Met Gly Leu Val Thr His Leu Gln Tyr Pro Val Pro Leu
                 85                  90                  95

Glu Glu Glu Asp Asp Glu Asp Thr Glu Ser Val Ser Pro Pro Glu
            100                 105                 110

Leu Pro Pro Arg Asn Ile Pro Ala Glu Ala Lys Pro Glu Asn Pro Arg
            115                 120                 125

Ala Glu Arg Ser Leu Ser Glu Thr Leu Phe Gln Arg Leu Gln Ser Met
130                 135                 140

Asp Thr Ser Gly Leu Pro Glu Glu His Leu Lys Ala Ile Gln Asp Tyr
145                 150                 155                 160

Leu Ser Thr Gln Leu Asp Ser Phe Lys Thr Gly Ser Ser Leu Pro His
                165                 170                 175

Leu Lys Lys Leu Leu Leu Cys Lys Glu Leu Gly Glu Val Ile Arg Thr
            180                 185                 190

Leu Pro Ser Leu Glu Ser Leu Gln Arg Leu Phe Asp Gln Gln Leu Ser
            195                 200                 205

Pro Gly Leu Arg Pro Arg Pro Gln Val Pro Gly Glu Ala Pro Ile Met
210                 215                 220

Val Lys Leu Ser Gln Leu Thr Ser Leu Leu Ser Ser Ile Glu Asp Lys
225                 230                 235                 240

Val Lys Leu Leu His Glu Gly Glu Ser Arg Ser Leu Ile Pro Pro Val
                245                 250                 255

Thr Phe Glu Val Lys Glu Ser Leu Gly Ile Pro Gln Lys Met Leu Lys
            260                 265                 270

Val Asp Val Glu Ser Gly Lys Leu Ile Lys Lys Ser Lys Asp Gly Ser
            275                 280                 285

Glu Asp Lys Phe Tyr Ser His Lys Lys Ile Leu Gln Leu Ile Lys Ser
290                 295                 300

Gln Lys Phe Leu Asn Lys Leu Val Ile Leu Val Glu Thr Glu Lys Glu
305                 310                 315                 320

Lys Ile Leu Arg Lys Glu Tyr Val Phe Ala Asp Ser Lys Lys Arg Glu
                325                 330                 335

Gly Phe Cys Gln Leu Leu Gln Gln Met Lys Asn Lys His Ser Glu Gln
            340                 345                 350

Pro Glu Pro Asp Met Ile Thr Ile Phe Ile Gly Thr Trp Asn Met Gly
            355                 360                 365

Asn Ala Pro Pro Pro Lys Lys Ile Thr Ser Trp Phe Leu Ser Lys Gly
370                 375                 380

Gln Gly Lys Thr Arg Asp Asp Ser Ala Asp Tyr Ile Pro His Asp Ile
385                 390                 395                 400

Tyr Val Ile Gly Thr Gln Glu Asp Pro Leu Glu Lys Glu Trp Leu Glu
                405                 410                 415

Leu His Ser Leu Gln Glu Thr Ser Thr Phe Lys Thr Val Ala Ile His
            420                 425                 430

Thr Leu Trp Asn Ile Arg Ile Val Val Leu Ala Lys Pro Glu His Glu
            435                 440                 445

Asn Arg Ile Ser His Ile Cys Thr Asp Asn Val Lys Thr Gly Ile Ala
450                 455                 460

Asn Thr Leu Gly Asn Lys Gly Ala Val Gly Val Ser Phe Met Phe Asn
465                 470                 475                 480

Gly Thr Ser Leu Gly Phe Val Asn Ser His Leu Thr Ser Gly Ser Glu
                485                 490                 495
```

-continued

Lys Lys Leu Arg Arg Asn Gln Asn Tyr Met Asn Ile Leu Arg Phe Leu
            500                 505                 510

Ala Leu Gly Asp Lys Lys Leu Ser Pro Phe Asn Ile Thr His Arg Phe
        515                 520                 525

Thr His Leu Phe Trp Gly Asp Leu Asn Tyr Arg Val Leu Pro Thr Trp
    530                 535                 540

Glu Ala Glu Ile Ile Gln Lys Ile Lys Gln Gln Gln Tyr Asp Leu Leu
545                 550                 555                 560

His Asp Gln Leu Leu Glu Arg Gln Lys Val Phe Leu His Phe Glu Glu
                565                 570                 575

Glu Glu Ile Thr Phe Ala Pro Thr Tyr Arg Phe Glu Arg Leu Thr Arg
            580                 585                 590

Asp Lys Tyr Ala Tyr Thr Lys Gln Lys Ala Thr Gly Met Lys Tyr Asn
        595                 600                 605

Leu Pro Ser Trp Cys Asp Arg Val Leu Trp Lys Ser Tyr Pro Leu Val
    610                 615                 620

His Val Val Cys Gln Ser Tyr Gly Ser Thr Ser Asp Ile Met Thr Ser
625                 630                 635                 640

Asp His Ser Pro Val Phe Ala Thr Phe Glu Ala Gly Val Thr Ser Gln
                645                 650                 655

Phe Val Ser Lys Asn Gly Pro Gly Thr Val Asp Ser Gln Gly Gln Ile
            660                 665                 670

Glu Phe Leu Cys Tyr Ala Thr Leu Lys Thr Lys Ser Gln Thr Lys Phe
        675                 680                 685

Tyr Leu Glu Phe His Ser Ser Cys Leu Glu Ser Phe Val Lys Ser Gln
    690                 695                 700

Glu Gly Glu Asn Glu Glu Gly Ser Glu Gly Glu Leu Val Val Phe Gly
705                 710                 715                 720

Glu Thr Leu Pro Lys Leu Lys Pro Ile Ile Ser Asp Pro Glu Tyr Leu
                725                 730                 735

Leu Asp Gln His Ile Leu Ile Ser Ile Lys Ser Ser Asp Ser Asp Glu
            740                 745                 750

Ser Tyr Gly Glu Gly Cys Ile Ala Leu Arg Leu Glu Thr Glu Gln Pro
        755                 760                 765

Ile Tyr Thr Pro Leu Thr His His Gly Glu Thr Gly His Phe Gly Glu
    770                 775                 780

Ile Lys Leu Gln Thr Ser Gln Gly Lys Arg Glu Lys Leu Tyr Asp Phe
785                 790                 795                 800

Val Lys Thr Glu Arg Asp Glu Ser Ser Gly Lys Leu Lys Leu Thr Ser
                805                 810                 815

His Asp Pro Met Gln Trp Glu Arg Pro Cys Ser Ser Glu Ile Asn Pro
            820                 825                 830

Asn Tyr Gly Gly Pro Phe Gly Pro Leu His Lys Thr Leu Ser Pro Asp
        835                 840                 845

Gln Gln Thr Ala Trp Ser Tyr Asp Gln Pro Lys Asp Ser Leu Gly Pro
    850                 855                 860

Arg Gly Glu Pro Pro Thr Pro Gln Pro Ser Pro Lys Lys Phe
865                 870                 875                 880

Ser Thr Asn Arg Gly Pro Arg Gln Glu Arg Pro Asp Leu Gly Lys Leu
                885                 890                 895

Gln Glu Asp Leu Leu Thr Lys Pro Glu Met Phe Glu Asn Pro Leu Tyr
            900                 905                 910

Gly Ser Ser Ser Phe Pro Lys Pro Arg Lys Gln Glu Ser Pro Lys Met

```
                915                 920                 925
Arg Lys Glu Pro Pro Cys Pro Pro Gly Ile Ser Pro Ser Ile Val
    930                 935                 940

Leu Lys Ala Gln Glu Gly Lys Gln Pro Pro Arg Arg Ser Phe Thr Cys
945                 950                 955                 960

Ser Ser Ser Ala Glu Gly Arg Gly Asp Lys Ser Gln Gly Lys Pro Lys
                965                 970                 975

Ser Ser Gln Ala Pro Val Pro Lys Arg Pro Lys Pro Ser Arg Ser Glu
            980                 985                 990

Gln Gln Thr Pro Pro Arg Pro Pro Leu Pro Val Lys Ser Pro Ala
                995                 1000                1005

Val Leu Leu Gln His Ser Lys Gly Arg Asp Tyr Arg Asp Asn Thr
    1010                1015                1020

Glu Leu Pro His His Gly Lys His Arg Gly Leu Gly Arg Thr Ala
    1025                1030                1035

Met Gln
    1040

<210> SEQ ID NO 4
<211> LENGTH: 112
<212> TYPE: PRT
<213> ORGANISM: Homo sapiens

<400> SEQUENCE: 4

Ser Pro His Arg Pro Ser Leu Ile Pro Pro Val Thr Phe Glu Val Lys
1               5                   10                  15

Ala Glu Ser Leu Gly Ile Pro Gln Lys Met Gln Leu Lys Val Asp Val
            20                  25                  30

Glu Ser Gly Lys Leu Ile Ile Lys Ser Lys Asp Gly Ser Glu Asp
        35                  40                  45

Lys Phe Tyr Ser His Lys Lys Ile Leu Gln Leu Ile Lys Ser Gln Lys
    50                  55                  60

Phe Leu Asn Lys Leu Val Ile Leu Val Glu Thr Glu Lys Glu Lys Ile
65                  70                  75                  80

Leu Arg Lys Glu Tyr Val Phe Ala Asp Ser Lys Lys Arg Glu Gly Phe
                85                  90                  95

Cys Gln Leu Leu Gln Gln Met Lys Asn Lys His Ser Glu Gln Pro Glu
            100                 105                 110

<210> SEQ ID NO 5
<211> LENGTH: 112
<212> TYPE: PRT
<213> ORGANISM: Pan troglodytes

<400> SEQUENCE: 5

Ser Pro His Arg Arg Ser Leu Ile Pro Pro Val Thr Phe Glu Val Lys
1               5                   10                  15

Ala Glu Ser Leu Gly Ile Pro Gln Lys Met Gln Leu Lys Val Asp Val
            20                  25                  30

Glu Ser Gly Lys Leu Ile Ile Lys Ser Lys Asp Gly Ser Glu Asp
        35                  40                  45

Lys Phe Tyr Ser His Lys Lys Ile Leu Gln Leu Ile Lys Ser Gln Lys
    50                  55                  60

Phe Leu Asn Lys Leu Val Ile Leu Val Glu Thr Glu Lys Glu Lys Ile
65                  70                  75                  80

Leu Arg Lys Glu Tyr Val Phe Ala Asp Ser Lys Lys Arg Glu Gly Phe
```

```
                    85                  90                  95
Cys Gln Leu Leu Gln Gln Met Lys Asn Lys His Ser Glu Gln Pro Glu
            100                 105                 110

<210> SEQ ID NO 6
<211> LENGTH: 112
<212> TYPE: PRT
<213> ORGANISM: Bos taurus

<400> SEQUENCE: 6

Ser Pro His Arg Arg Ser Leu Ile Pro Pro Val Thr Phe Glu Val Lys
1               5                   10                  15

Ala Glu Ser Leu Gly Ile Pro Gln Lys Leu Gln Leu Lys Val Asp Val
            20                  25                  30

Glu Ser Gly Lys Leu Ile Ile Lys Lys Ser Lys Asp Ser Ser Glu Asp
        35                  40                  45

Lys Phe Tyr Thr His Lys Lys Ile Leu Gln Leu Ile Lys Ser Gln Lys
    50                  55                  60

Phe Leu Asn Lys Leu Val Ile Leu Val Glu Thr Glu Lys Glu Lys Thr
65                  70                  75                  80

Leu Arg Lys Glu Tyr Val Phe Ala Asp Ser Lys Arg Glu Gly Phe
                85                  90                  95

Cys Gln Leu Leu Gln Gln Met Lys Asn Lys His Ser Glu Gln Pro Glu
            100                 105                 110

<210> SEQ ID NO 7
<211> LENGTH: 112
<212> TYPE: PRT
<213> ORGANISM: Mus musculus

<400> SEQUENCE: 7

Ser Thr Asn Arg Arg Ser Leu Ile Pro Pro Val Thr Phe Glu Val Lys
1               5                   10                  15

Ser Glu Ser Leu Gly Ile Pro Gln Lys Met His Leu Lys Val Asp Val
            20                  25                  30

Glu Ser Gly Lys Leu Ile Val Lys Lys Ser Lys Asp Gly Ser Glu Asp
        35                  40                  45

Lys Phe Tyr Ser His Lys Lys Ile Leu Gln Leu Ile Lys Ser Gln Lys
    50                  55                  60

Phe Leu Asn Lys Leu Val Ile Leu Val Glu Thr Glu Lys Glu Lys Ile
65                  70                  75                  80

Leu Arg Lys Glu Tyr Val Phe Ala Asp Ser Lys Arg Glu Gly Phe
                85                  90                  95

Cys Gln Leu Leu Gln Gln Met Lys Asn Lys His Ser Glu Gln Pro Glu
            100                 105                 110

<210> SEQ ID NO 8
<211> LENGTH: 112
<212> TYPE: PRT
<213> ORGANISM: Rattus norvegicus

<400> SEQUENCE: 8

Ser Thr Asn Arg Arg Ser Leu Ile Pro Pro Val Thr Phe Glu Val Lys
1               5                   10                  15

Ser Glu Ser Leu Gly Ile Pro Gln Lys Met His Leu Lys Val Asp Val
            20                  25                  30

Glu Ser Gly Lys Leu Ile Ile Lys Lys Ser Arg Asp Gly Ser Glu Asp
        35                  40                  45
```

```
Lys Phe Tyr Ser His Lys Lys Ile Leu Gln Leu Ile Lys Ser Gln Lys
         50                  55                  60
Phe Leu Asn Lys Leu Val Ile Leu Val Glu Thr Glu Lys Glu Lys Ile
 65                  70                  75                  80
Leu Arg Lys Glu Tyr Val Phe Ser Asp Ser Lys Arg Glu Gly Phe
                 85                  90                  95
Cys Gln Leu Leu Gln Gln Met Lys Asn Lys His Ser Glu Gln Ser Glu
                100                 105                 110
```

<210> SEQ ID NO 9
<211> LENGTH: 112
<212> TYPE: PRT
<213> ORGANISM: Monodelphis domestica

<400> SEQUENCE: 9

```
Ser Thr His Arg Arg Ser Leu Ile Pro Pro Val Thr Phe Glu Val Lys
 1               5                  10                  15
Ser Glu Ser Leu Gly Ile Pro Gln Lys Met Gln Leu Lys Val Asp Val
                 20                  25                  30
Glu Ser Gly Lys Leu Ile Ile Lys Ser Lys Asp Gly Pro Glu Asp
             35                  40                  45
Lys Phe Tyr Ser His Lys Lys Ile Leu Gln Leu Ile Lys Ser Gln Lys
         50                  55                  60
Phe His Asn Lys Leu Val Ile Val Val Glu Thr Glu Lys Glu Lys Thr
 65                  70                  75                  80
Leu Arg Lys Glu Tyr Val Phe Ala Asp Ser Lys Arg Glu Gly Phe
                 85                  90                  95
Cys Gln Leu Leu Gln Gln Met Lys Asn Lys His Ser Glu Gln Pro Glu
                100                 105                 110
```

<210> SEQ ID NO 10
<211> LENGTH: 112
<212> TYPE: PRT
<213> ORGANISM: Gallus gallus

<400> SEQUENCE: 10

```
Ser Thr His Arg Arg Ser Leu Ile Pro Pro Val Thr Phe Glu Val Lys
 1               5                  10                  15
Ala Asp Ser Leu Gly Ile Phe Ser Lys Ile His Leu Lys Val Asp Val
                 20                  25                  30
Glu Met Gly Lys Leu Ile Ile Lys Arg Ala Lys Asp Gly Pro Glu Asp
             35                  40                  45
Lys Phe Tyr Thr His Lys Lys Ile Leu Gln Leu Ile Lys Ser Gln Lys
         50                  55                  60
Val Pro Asn Lys Leu Val Ile Met Leu Glu Thr Glu Lys Glu Lys Thr
 65                  70                  75                  80
Gln Arg Lys Glu Tyr Val Phe Ser Asp Ser Lys Arg Glu Gly Phe
                 85                  90                  95
Cys Gln Leu Leu Gln Gln Met Lys Asn Lys His Ser Glu Gln Pro Glu
                100                 105                 110
```

<210> SEQ ID NO 11
<211> LENGTH: 112
<212> TYPE: PRT
<213> ORGANISM: Xenopus laevis

<400> SEQUENCE: 11

Val Lys His Arg Arg Ser Leu Ile Pro Pro Ile Phe Glu Val Lys
1               5                   10                  15

Ala Asp Ser Ile Gly Ile Ser Gln Lys Thr His Leu Lys Val Asp Val
            20                  25                  30

Glu Thr Gly Lys Leu Ile Ile Lys Lys Ser Lys Asp Gly Pro Asp Asp
        35                  40                  45

Lys Phe Tyr Pro Ser Lys Lys Ile Leu Gln Leu Ile Lys Ser Gln Lys
    50                  55                  60

Phe Pro His Lys Leu Val Ile Val Leu Glu Thr Glu Lys Glu Lys Thr
65                  70                  75                  80

Gln Arg Lys Glu Tyr Val Phe Ala Asp Ser Lys Arg Glu Gly Phe
                85                  90                  95

Cys Gln Leu Leu Gln Gln Met Lys Asn Lys His Ser Gly Gln Ser Glu
            100                 105                 110

<210> SEQ ID NO 12
<211> LENGTH: 121
<212> TYPE: PRT
<213> ORGANISM: Rattus norvegicus

<400> SEQUENCE: 12

Ser Ile Arg Lys Ala Lys Thr Ile Pro Val Gln Ala Phe Glu Val Lys
1               5                   10                  15

Leu Asp Val Thr Leu Gly Asp Leu Thr Lys Ile Gly Lys Ser Gln Lys
            20                  25                  30

Phe Thr Leu Ser Val Asp Val Glu Gly Gly Arg Leu Val Leu Leu Arg
        35                  40                  45

Arg Gln Arg Asp Ser Gln Glu Asp Trp Thr Thr Phe Thr His Asp Arg
    50                  55                  60

Ile Arg Gln Leu Ile Lys Ser Gln Arg Val Gln Asn Lys Leu Gly Val
65                  70                  75                  80

Val Phe Glu Lys Glu Lys Asp Arg Thr Gln Arg Lys Asp Phe Ile Phe
                85                  90                  95

Val Ser Ala Arg Lys Arg Glu Ala Phe Cys Gln Leu Leu Gln Leu Met
            100                 105                 110

Lys Asn Lys His Ser Lys Gln Asp Glu
    115                 120

<210> SEQ ID NO 13
<211> LENGTH: 121
<212> TYPE: PRT
<213> ORGANISM: Mus musculus

<400> SEQUENCE: 13

Ser Ile Arg Lys Ala Lys Thr Ile Pro Val Gln Ala Phe Glu Val Lys
1               5                   10                  15

Leu Asp Val Thr Leu Gly Asp Leu Thr Lys Ile Gly Lys Ser Gln Lys
            20                  25                  30

Phe Thr Leu Ser Val Asp Val Glu Gly Gly Arg Leu Val Leu Leu Arg
        35                  40                  45

Arg Gln Arg Asp Ser Gln Glu Asp Trp Thr Thr Phe Thr His Asp Arg
    50                  55                  60

Ile Arg Gln Leu Ile Lys Ser Gln Arg Val Gln Asn Lys Leu Gly Val
65                  70                  75                  80

Val Phe Glu Lys Glu Lys Asp Arg Thr Gln Arg Lys Asp Phe Ile Phe
                85                  90                  95

Val Ser Ala Arg Lys Arg Glu Ala Phe Cys Gln Leu Leu Gln Leu Ile
            100                 105                 110

Lys Asn Arg His Ser Lys Gln Asp Glu
        115                 120

<210> SEQ ID NO 14
<211> LENGTH: 121
<212> TYPE: PRT
<213> ORGANISM: Homo sapiens

<400> SEQUENCE: 14

Ser Thr Arg Lys Ala Lys Thr Ile Pro Val Gln Ala Phe Glu Val Lys
1               5                   10                  15

Leu Asp Val Thr Leu Gly Asp Leu Thr Lys Ile Gly Lys Ser Gln Lys
            20                  25                  30

Phe Thr Leu Ser Val Asp Val Glu Gly Gly Arg Leu Val Leu Leu Arg
        35                  40                  45

Arg Gln Arg Asp Ser Gln Glu Asp Trp Thr Thr Phe Thr His Asp Arg
    50                  55                  60

Ile Arg Gln Leu Ile Lys Ser Gln Arg Val Gln Asn Lys Leu Gly Val
65                  70                  75                  80

Val Phe Glu Lys Glu Lys Asp Arg Thr Gln Arg Lys Asp Phe Ile Phe
                85                  90                  95

Val Ser Ala Arg Lys Arg Glu Ala Phe Cys Gln Leu Leu Gln Leu Met
            100                 105                 110

Lys Asn Lys His Ser Lys Gln Asp Glu
        115                 120

<210> SEQ ID NO 15
<211> LENGTH: 120
<212> TYPE: PRT
<213> ORGANISM: Danio rerio

<400> SEQUENCE: 15

Ser Ile Arg Asn Lys Val Ile Pro Val Gln Thr Phe Glu Val Lys Leu
1               5                   10                  15

Asp Val Tyr Leu Ala Asp Leu Thr Lys Ile Gly Lys Ser Gln Lys Tyr
            20                  25                  30

Ser Leu Ser Val Asp Val Glu Gly Gly Lys Leu Val Val Met Lys Lys
        35                  40                  45

Met Lys Asp Ala Gln Glu Asp Trp Asn Thr Phe Thr His Asp Lys Ile
    50                  55                  60

Arg Gln Leu Ile Lys Ser Gln Arg Val Gln Asn Lys Leu Gly Ile Val
65                  70                  75                  80

Phe Glu Lys Glu Lys Asp Lys Ser Gln Arg Lys Asp Phe Ile Phe Ala
                85                  90                  95

Ser Ala Lys Lys Arg Glu Ala Phe Cys Gln Leu Leu Gln Leu Met Lys
            100                 105                 110

Asn Lys His Ser Asn Gln Asp Glu
        115                 120

<210> SEQ ID NO 16
<211> LENGTH: 154
<212> TYPE: PRT
<213> ORGANISM: Mus musculus

<400> SEQUENCE: 16

Thr Phe Glu Ala Gly Val Thr Ser Gln Phe Val Ser Lys Asn Gly Pro

```
                 1               5                  10                 15
              Gly Thr Val Asp Ser Gln Gly Gln Ile Glu Phe Leu Ala Cys Tyr Ala
                            20                  25                 30

Thr Leu Lys Thr Lys Ser Gln Thr Lys Phe Tyr Leu Glu Phe His Ser
                            35                  40                 45

Ser Cys Leu Glu Ser Phe Val Lys Ser Gln Glu Gly Glu Asn Glu Glu
                            50                  55                 60

Gly Ser Glu Gly Glu Leu Val Val Arg Phe Gly Glu Thr Leu Pro Lys
              65                        70                  75                 80

Leu Lys Pro Ile Ile Ser Asp Pro Glu Tyr Leu Leu Asp Gln His Ile
                                  85                  90                 95

Leu Ile Ser Ile Lys Ser Ser Asp Ser Asp Glu Ser Tyr Gly Glu Gly
                            100                 105                110

Cys Ile Ala Leu Arg Leu Glu Thr Glu Ala Gln His Pro Ile Tyr
                            115                 120                125

Thr Pro Leu Thr His His Gly Glu Met Thr Gly His Phe Arg Gly Glu
                            130                 135                140

Ile Lys Leu Gln Thr Ser Gln Gly Lys Met
              145                       150

<210> SEQ ID NO 17
<211> LENGTH: 154
<212> TYPE: PRT
<213> ORGANISM: Rattus norvegicus

<400> SEQUENCE: 17

Thr Phe Glu Ala Gly Val Thr Ser Gln Phe Val Ser Lys Asn Gly Pro
              1               5                  10                 15

Gly Ala Val Asp Ser Gln Gly Gln Ile Glu Phe Leu Ala Cys Tyr Ala
                            20                  25                 30

Thr Leu Lys Thr Lys Ser Gln Thr Lys Phe Tyr Leu Glu Leu His Ser
                            35                  40                 45

Ser Cys Leu Glu Ser Phe Val Lys Ser Gln Glu Gly Glu Asn Glu Glu
                            50                  55                 60

Gly Asp Glu Gly Glu Leu Val Val Arg Phe Gly Glu Thr Leu Pro Lys
              65                        70                  75                 80

Leu Lys Pro Ile Ile Ser Asp Pro Glu Tyr Leu Leu Asp Gln His Ile
                                  85                  90                 95

Leu Ile Ser Ile Lys Ser Ser Asp Ser Asp Glu Ser Tyr Gly Glu Gly
                            100                 105                110

Cys Ile Ala Leu Arg Leu Glu Thr Glu Ser Gln Leu Pro Ile Tyr
                            115                 120                125

Thr Pro Leu Thr His His Gly Glu Met Thr Gly His Phe Arg Gly Glu
                            130                 135                140

Ile Lys Leu Gln Thr Ser Glu Gly Lys Met
              145                       150

<210> SEQ ID NO 18
<211> LENGTH: 154
<212> TYPE: PRT
<213> ORGANISM: Homo sapiens

<400> SEQUENCE: 18

Thr Phe Glu Ala Gly Val Thr Ser Gln Phe Val Ser Lys Asn Gly Pro
              1               5                  10                 15

Gly Thr Val Asp Ser Gln Gly Gln Ile Glu Phe Leu Arg Cys Tyr Ala
```

```
                    20                  25                  30

Thr Leu Lys Thr Lys Ser Gln Thr Lys Phe Tyr Leu Glu Phe His Ser
            35                  40                  45

Ser Cys Leu Glu Ser Phe Val Lys Ser Gln Glu Gly Glu Asn Glu Glu
    50                  55                  60

Gly Ser Glu Gly Glu Leu Val Val Lys Phe Gly Thr Leu Pro Lys
65                  70                  75                  80

Leu Lys Pro Ile Ile Ser Asp Pro Glu Tyr Leu Leu Asp Gln His Ile
                85                  90                  95

Leu Ile Ser Ile Lys Ser Ser Asp Ser Asp Glu Ser Tyr Gly Glu Gly
            100                 105                 110

Cys Ile Ala Leu Arg Leu Glu Ala Thr Glu Thr Gln Leu Pro Ile Tyr
                115                 120                 125

Thr Pro Leu Thr His His Gly Glu Leu Thr Gly His Phe Gln Gly Glu
            130                 135                 140

Ile Lys Leu Gln Thr Ser Gln Gly Lys Thr
145                 150

<210> SEQ ID NO 19
<211> LENGTH: 154
<212> TYPE: PRT
<213> ORGANISM: Pan troglodytes

<400> SEQUENCE: 19

Thr Phe Glu Ala Gly Val Thr Ser Gln Phe Val Ser Lys Asn Gly Pro
1               5                   10                  15

Gly Thr Val Asp Ser Gln Gly Gln Ile Glu Phe Leu Arg Cys Tyr Ala
            20                  25                  30

Thr Leu Lys Thr Lys Ser Gln Thr Lys Phe Tyr Leu Glu Phe His Ser
            35                  40                  45

Ser Cys Leu Glu Ser Phe Val Lys Ser Gln Glu Gly Glu Asn Glu Glu
    50                  55                  60

Gly Ser Glu Gly Glu Leu Val Val Lys Phe Gly Thr Leu Pro Lys
65                  70                  75                  80

Leu Lys Pro Ile Ile Ser Asp Pro Glu Tyr Leu Leu Asp Gln His Ile
                85                  90                  95

Leu Ile Ser Ile Lys Ser Ser Asp Ser Asp Glu Ser Tyr Gly Glu Gly
            100                 105                 110

Cys Ile Ala Leu Arg Leu Glu Ala Thr Glu Thr Gln Leu Pro Ile Tyr
                115                 120                 125

Thr Pro Leu Thr His His Gly Glu Leu Thr Gly His Phe Gln Gly Glu
            130                 135                 140

Ile Lys Leu Gln Thr Ser Gln Gly Lys Thr
145                 150

<210> SEQ ID NO 20
<211> LENGTH: 154
<212> TYPE: PRT
<213> ORGANISM: Bos taurus

<400> SEQUENCE: 20

Thr Phe Glu Ala Gly Val Thr Ser Gln Phe Val Ser Lys Asn Gly Pro
1               5                   10                  15

Gly Thr Thr Asp Ser Gln Gly Gln Ile Glu Phe Leu Gly Cys Tyr Ala
            20                  25                  30

Thr Leu Lys Thr Lys Ser Gln Thr Lys Phe Tyr Leu Glu Phe His Ser
```

```
                35                  40                  45

Ser Cys Leu Glu Ser Phe Val Lys Ser Gln Glu Gly Glu Asn Glu Glu
            50                  55                  60

Gly Ser Glu Gly Glu Leu Val Val Lys Phe Gly Thr Leu Pro Lys
65                  70                  75                  80

Leu Lys Pro Ile Ile Ser Asp Pro Glu Tyr Leu Leu Asp Gln His Ile
                85                  90                  95

Leu Ile Ser Ile Lys Ser Ser Asp Ser Asp Glu Ser Tyr Gly Glu Gly
                100                 105                 110

Cys Ile Ala Leu Arg Leu Glu Ala Thr Glu Thr Gln Leu Pro Ile Tyr
                115                 120                 125

Thr Pro Leu Thr His His Gly Glu Met Thr Gly His Phe Arg Gly Asn
                130                 135                 140

Ile Lys Leu Gln Thr Ser Gln Gly Lys Met
145                 150

<210> SEQ ID NO 21
<211> LENGTH: 154
<212> TYPE: PRT
<213> ORGANISM: Monodelphis domestica

<400> SEQUENCE: 21

Thr Phe Glu Val Gly Val Thr Ser Gln Phe Val Ser Lys Asn Gly Pro
1               5                   10                  15

Gly Asn Val Asp Ser Gln Gly Gln Ile Glu Phe Leu Asn Cys Tyr Ala
                20                  25                  30

Thr Leu Lys Thr Lys Ser Gln Thr Lys Phe Tyr Leu Glu Phe His Ser
                35                  40                  45

Ser Cys Leu Glu Ser Phe Val Lys Ser Gln Gly Glu Asn Glu Glu
            50                  55                  60

Gly Thr Glu Gly Glu Leu Val Val Lys Phe Ala Asp Asp Leu Pro Lys
65                  70                  75                  80

Leu Thr Pro Ile Ile Ser Asp Pro Glu Tyr Leu Leu Asp Gln His Ile
                85                  90                  95

Leu Ile Ser Ile Lys Ser Ser Asp Ser Asp Glu Ser Tyr Gly Glu Gly
                100                 105                 110

Cys Ile Ala Leu Arg Ser Glu Ala Ile Glu Ser Leu Val Pro Ile Tyr
                115                 120                 125

Thr Ala Leu Thr His His Gly Glu Met Met Gly His Phe Arg Gly Glu
                130                 135                 140

Ile Lys Leu Gln Thr Ser Gln Gly Lys Lys
145                 150

<210> SEQ ID NO 22
<211> LENGTH: 154
<212> TYPE: PRT
<213> ORGANISM: Gallus gallus

<400> SEQUENCE: 22

Thr Phe Glu Val Gly Val Thr Ser Gln Phe Val Ser Lys Asn Asp Ser
1               5                   10                  15

Lys Tyr Met Asn Thr Gln Gly Glu Ile Glu Phe Leu His Cys Phe Ala
                20                  25                  30

Thr Leu Lys Thr Lys Ser Gln Thr Lys Phe Tyr Ile Glu Phe His Ser
                35                  40                  45

Ser Cys Leu Glu Ser Phe Val Lys Ser Gln Glu Gly Glu Asn Glu Asp
```

```
Gly Ser Glu Gly Glu Leu Val Val Lys Phe Val Asp Ala Leu Pro Lys
 65                  70                  75                  80

Leu Thr Pro Ile Ile Ser Asp Pro Glu Tyr Leu Leu Asp Gln His Ile
                 85                  90                  95

Leu Ile Ser Ile Lys Ser Ser Asp Ser Asp Glu Ser Tyr Gly Glu Gly
            100                 105                 110

Cys Ile Ala Leu Arg Ile Glu Ala Thr Glu Ser Leu Val Pro Ile His
        115                 120                 125

Thr Val Leu Thr His His Gly Glu Lys Thr Gly Val Phe Gln Gly Glu
    130                 135                 140

Ile Lys Leu Gln Thr Ser Gln Gly Lys Gln
145                 150
```

<210> SEQ ID NO 23
<211> LENGTH: 156
<212> TYPE: PRT
<213> ORGANISM: Xenopus laevis

<400> SEQUENCE: 23

```
Thr Phe Gln Val Gly Val Thr Ser Gln Phe Val Ser Lys Asn Asn Pro
  1               5                  10                  15

Gly Asp Ser Gly Asp Leu Glu Ala Gln Gly His Ile Glu Leu Met Asn
             20                  25                  30

Cys Lys Ala Thr Leu Tyr Thr Lys Ser His Thr Lys Phe Tyr Ile Glu
         35                  40                  45

Phe His Ser Pro Cys Leu Glu Asn Met Val Lys Ser Glu Ala Glu
     50                  55                  60

Asp Gln Glu Gly Asn Asn Gly Thr Leu Val Val Lys Phe Gly Val Leu
 65                  70                  75                  80

Pro Lys Leu Thr Pro Ile Ile Ser Asp Leu Glu Tyr Leu Leu Asp Gln
                 85                  90                  95

His Leu Leu Ile Cys Ile Lys Ser Ser Asp Thr Asp Glu Ser Tyr Gly
            100                 105                 110

Glu Gly Cys Ile Ala Leu Arg Lys Glu Asp Thr Glu Gln Gln Phe Pro
        115                 120                 125

Phe Cys Thr Ile Leu Thr His His Gly Glu Glu Thr Gly Leu Phe Cys
    130                 135                 140

Gly Glu Ile Cys Leu Pro Ala Ser Gly Gly Lys Gln
145                 150                 155
```

<210> SEQ ID NO 24
<211> LENGTH: 158
<212> TYPE: PRT
<213> ORGANISM: Rattus norvegicus

<400> SEQUENCE: 24

```
Thr Phe Glu Val Gly Val Thr Ser Gln Phe Ile Ser Lys Lys Gly Leu
  1               5                  10                  15

Ser Lys Thr Ser Asp Gln Ala Tyr Ile Glu Phe Glu Ser Ile Glu Ala
             20                  25                  30

Ile Val Lys Thr Ala Ser Arg Thr Lys Phe Phe Ile Glu Phe Tyr Ser
         35                  40                  45

Thr Cys Leu Glu Glu Tyr Lys Lys Ser Phe Glu Asn Asp Ala Gln Ser
     50                  55                  60

Ser Asp Asn Ile Asn Phe Leu Lys Val Gln Trp Ser Ser Arg Gln Leu
```

```
                65                  70                  75                  80
Pro Thr Leu Lys Pro Ile Leu Ala Asp Ile Glu Tyr Leu Gln Asp Gln
                85                  90                  95

His Leu Leu Leu Thr Val Lys Ser Met Asp Gly Tyr Glu Ser Tyr Gly
            100                 105                 110

Glu Cys Val Val Ala Leu Lys Ser Met Ile Gly Ser Thr Ala Gln Gln
            115                 120                 125

Phe Leu Thr Phe Leu Ser His Arg Gly Glu Glu Thr Gly Asn Ile Arg
        130                 135                 140

Gly Ser Met Lys Val Arg Val Pro Thr Glu Arg Leu Gly Thr
145                 150                 155

<210> SEQ ID NO 25
<211> LENGTH: 158
<212> TYPE: PRT
<213> ORGANISM: Mus musculus

<400> SEQUENCE: 25

Thr Phe Glu Val Gly Val Thr Ser Gln Phe Ile Ser Lys Lys Gly Leu
1               5                   10                  15

Ser Lys Thr Ser Asp Gln Ala Tyr Ile Glu Phe Glu Ser Ile Glu Ala
            20                  25                  30

Ile Val Lys Thr Ala Ser Arg Thr Lys Phe Phe Ile Glu Phe Tyr Ser
        35                  40                  45

Thr Cys Leu Glu Glu Tyr Lys Lys Ser Phe Glu Asn Asp Ala Gln Ser
    50                  55                  60

Ser Asp Asn Ile Asn Phe Leu Lys Val Gln Trp Ser Ser Arg Gln Leu
65                  70                  75                  80

Pro Thr Leu Lys Pro Ile Leu Ala Asp Ile Glu Tyr Leu Gln Asp Gln
                85                  90                  95

His Leu Leu Leu Thr Val Lys Ser Met Asp Gly Tyr Glu Ser Tyr Gly
            100                 105                 110

Glu Cys Val Val Ala Leu Lys Ser Met Ile Gly Ser Thr Ala Gln Gln
            115                 120                 125

Phe Leu Thr Phe Leu Ser His Arg Gly Glu Glu Thr Gly Asn Ile Arg
        130                 135                 140

Gly Ser Met Lys Val Arg Val Pro Thr Glu Arg Leu Gly Thr
145                 150                 155

<210> SEQ ID NO 26
<211> LENGTH: 158
<212> TYPE: PRT
<213> ORGANISM: Homo sapiens

<400> SEQUENCE: 26

Thr Phe Glu Val Gly Val Thr Ser Gln Phe Ile Ser Lys Lys Gly Leu
1               5                   10                  15

Ser Lys Thr Ser Asp Gln Ala Tyr Ile Glu Phe Glu Ser Ile Glu Ala
            20                  25                  30

Ile Val Lys Thr Ala Ser Arg Thr Lys Phe Phe Ile Glu Phe Tyr Ser
        35                  40                  45

Thr Cys Leu Glu Glu Tyr Lys Lys Ser Phe Glu Asn Asp Ala Gln Ser
    50                  55                  60

Ser Asp Asn Ile Asn Phe Leu Lys Val Gln Trp Ser Ser Arg Gln Leu
65                  70                  75                  80

Pro Thr Leu Lys Pro Ile Leu Ala Asp Ile Glu Tyr Leu Gln Asp Gln
```

```
                    85                  90                  95

His Leu Leu Leu Thr Val Lys Ser Met Asp Gly Tyr Glu Ser Tyr Gly
                100                 105                 110

Glu Cys Val Ala Leu Lys Ser Met Ile Gly Ser Thr Ala Gln Gln
            115                 120                 125

Phe Leu Thr Phe Leu Ser His Arg Gly Glu Glu Thr Gly Asn Ile Arg
    130                 135                 140

Gly Ser Met Lys Val Arg Val Pro Thr Glu Arg Leu Gly Thr
145                 150                 155

<210> SEQ ID NO 27
<211> LENGTH: 158
<212> TYPE: PRT
<213> ORGANISM: Danio rerio

<400> SEQUENCE: 27

Thr Phe Glu Val Gly Val Thr Ser Gln Phe Val Ser Lys Lys Gly Leu
1               5                   10                  15

Pro Lys Ser Ser Glu Gln Ala Tyr Ile Glu Phe Glu Asn Ile Glu Ala
            20                  25                  30

Ile Val Lys Thr Ala Ser Arg Thr Lys Phe Phe Ile Glu Phe Tyr Ser
        35                  40                  45

Thr Cys Leu Glu Glu Phe Lys Lys Ser Tyr Glu Asn Asp Thr Gln Ser
    50                  55                  60

Ser Asp Asn Val Asn Phe Leu Arg Val Gly Trp Ser Ser Lys Gln Leu
65                  70                  75                  80

Thr Thr Leu Lys Pro Ile Leu Ser Asp Ile Glu Tyr Leu Gln Asp Gln
                85                  90                  95

His Leu Leu Leu Thr Val Lys Ser Leu Asp Gly Tyr Glu Ser Tyr Gly
                100                 105                 110

Glu Cys Val Leu Ala Leu Lys Ser Met Ile Gly Ser Thr Ala Gln Gln
            115                 120                 125

Phe His Thr Tyr Leu Ser His Arg Gly Glu Glu Thr Gly Asn Ile Arg
    130                 135                 140

Gly Ser Met Arg Val Arg Val Pro Ser Glu Arg Met Gly Thr
145                 150                 155

<210> SEQ ID NO 28
<211> LENGTH: 139
<212> TYPE: PRT
<213> ORGANISM: Artificial
<220> FEATURE:
<223> OTHER INFORMATION: C2 domain of SHIP1

<400> SEQUENCE: 28

Pro Gly Thr Val Asp Ser Gln Gly Gln Ile Glu Phe Leu Ala Cys Tyr
1               5                   10                  15

Ala Thr Leu Lys Thr Lys Ser Gln Thr Lys Phe Tyr Leu Glu Phe His
            20                  25                  30

Ser Ser Cys Leu Glu Ser Phe Val Lys Ser Gln Glu Gly Glu Asn Glu
        35                  40                  45

Glu Gly Ser Glu Gly Glu Leu Val Val Arg Phe Gly Glu Thr Leu Pro
    50                  55                  60

Lys Leu Lys Pro Ile Ile Ser Asp Pro Glu Tyr Leu Leu Asp Gln His
65                  70                  75                  80

Ile Leu Ile Ser Ile Lys Ser Ser Asp Ser Asp Glu Ser Tyr Gly Glu
                85                  90                  95
```

Gly Cys Ile Ala Leu Arg Leu Glu Thr Thr Glu Ala Gln His Pro Ile
            100                 105                 110

Tyr Thr Pro Leu Thr His His Gly Glu Met Thr Gly His Phe Arg Gly
            115                 120                 125

Glu Ile Lys Leu Gln Thr Ser Gln Gly Lys Met
        130                 135

<210> SEQ ID NO 29
<211> LENGTH: 139
<212> TYPE: PRT
<213> ORGANISM: Artificial
<220> FEATURE:
<223> OTHER INFORMATION: C2 domain of SHIP1

<400> SEQUENCE: 29

Pro Gly Thr Val Asp Ser Gln Gly Gln Ile Glu Phe Leu Arg Cys Tyr
1               5                   10                  15

Ala Thr Leu Lys Thr Lys Ser Gln Thr Lys Phe Tyr Leu Glu Phe His
            20                  25                  30

Ser Ser Cys Leu Glu Ser Phe Val Lys Ser Gln Glu Gly Glu Asn Glu
        35                  40                  45

Glu Gly Ser Glu Gly Glu Leu Val Val Lys Phe Gly Glu Thr Leu Pro
    50                  55                  60

Lys Leu Lys Pro Ile Ile Ser Asp Pro Glu Tyr Leu Leu Asp Gln His
65                  70                  75                  80

Ile Leu Ile Ser Ile Lys Ser Ser Asp Ser Asp Glu Ser Tyr Gly Glu
                85                  90                  95

Gly Cys Ile Ala Leu Arg Leu Glu Ala Thr Glu Thr Gln Leu Pro Ile
            100                 105                 110

Tyr Thr Pro Leu Thr His His Gly Glu Leu Thr Gly His Phe Gln Gly
            115                 120                 125

Glu Ile Lys Leu Gln Thr Ser Gln Gly Lys Thr
        130                 135

<210> SEQ ID NO 30
<211> LENGTH: 149
<212> TYPE: PRT
<213> ORGANISM: Artificial
<220> FEATURE:
<223> OTHER INFORMATION: C2 domain of SHIP1

<400> SEQUENCE: 30

Val Thr Ser Gln Phe Val Ser Lys Asn Gly Pro Gly Thr Val Asp Ser
1               5                   10                  15

Gln Gly Gln Ile Glu Phe Leu Ala Cys Tyr Ala Thr Leu Lys Thr Lys
            20                  25                  30

Ser Gln Thr Lys Phe Tyr Leu Glu Phe His Ser Ser Cys Leu Glu Ser
        35                  40                  45

Phe Val Lys Ser Gln Glu Gly Glu Asn Glu Glu Gly Ser Glu Gly Glu
    50                  55                  60

Leu Val Val Arg Phe Gly Glu Thr Leu Pro Lys Leu Lys Pro Ile Ile
65                  70                  75                  80

Ser Asp Pro Glu Tyr Leu Leu Asp Gln His Ile Leu Ile Ser Ile Lys
                85                  90                  95

Ser Ser Asp Ser Asp Glu Ser Tyr Gly Glu Gly Cys Ile Ala Leu Arg
            100                 105                 110

Leu Glu Thr Thr Glu Ala Gln His Pro Ile Tyr Thr Pro Leu Thr His

```
                115                 120                 125
His Gly Glu Met Thr Gly His Phe Arg Gly Glu Ile Lys Leu Gln Thr
    130                 135                 140

Ser Gln Gly Lys Met
145
```

<210> SEQ ID NO 31
<211> LENGTH: 151
<212> TYPE: PRT
<213> ORGANISM: Artificial
<220> FEATURE:
<223> OTHER INFORMATION: C2 domain of SHIP1

<400> SEQUENCE: 31

```
Thr Phe Glu Ala Gly Val Thr Ser Gln Phe Val Ser Lys Asn Gly Pro
1               5                   10                  15

Gly Thr Val Asp Ser Gln Gly Gln Ile Glu Phe Leu Arg Cys Tyr Ala
            20                  25                  30

Thr Leu Lys Thr Lys Ser Gln Thr Lys Phe Tyr Leu Glu Phe His Ser
        35                  40                  45

Ser Cys Leu Glu Ser Phe Val Lys Ser Gln Glu Gly Glu Asn Glu Glu
    50                  55                  60

Gly Ser Glu Gly Glu Leu Val Val Lys Phe Gly Glu Thr Leu Pro Lys
65                  70                  75                  80

Leu Lys Pro Ile Ile Ser Asp Pro Glu Tyr Leu Leu Asp Gln His Ile
                85                  90                  95

Leu Ile Ser Ile Lys Ser Ser Asp Ser Asp Glu Ser Tyr Gly Glu Gly
            100                 105                 110

Cys Ile Ala Leu Arg Leu Glu Ala Thr Glu Thr Gln Leu Pro Ile Tyr
        115                 120                 125

Thr Pro Leu Thr His His Gly Glu Leu Thr Gly His Phe Gln Gly Glu
    130                 135                 140

Ile Lys Leu Gln Thr Ser Gln
145                 150
```

<210> SEQ ID NO 32
<211> LENGTH: 146
<212> TYPE: PRT
<213> ORGANISM: Artificial
<220> FEATURE:
<223> OTHER INFORMATION: C2 domain of SHIP1

<400> SEQUENCE: 32

```
Val Thr Ser Gln Phe Val Ser Lys Asn Gly Pro Gly Thr Val Asp Ser
1               5                   10                  15

Gln Gly Gln Ile Glu Phe Leu Ala Cys Tyr Ala Thr Leu Lys Thr Lys
            20                  25                  30

Ser Gln Thr Lys Phe Tyr Leu Glu Phe His Ser Ser Cys Leu Glu Ser
        35                  40                  45

Phe Val Lys Ser Gln Glu Gly Glu Asn Glu Glu Gly Ser Glu Gly Glu
    50                  55                  60

Leu Val Val Arg Phe Gly Glu Thr Leu Pro Lys Leu Lys Pro Ile Ile
65                  70                  75                  80

Ser Asp Pro Glu Tyr Leu Leu Asp Gln His Ile Leu Ile Ser Ile Lys
                85                  90                  95

Ser Ser Asp Ser Asp Glu Ser Tyr Gly Glu Gly Cys Ile Ala Leu Arg
            100                 105                 110
```

Leu Glu Thr Thr Glu Ala Gln His Pro Ile Tyr Thr Pro Leu Thr His
            115                 120                 125

His Gly Glu Met Thr Gly His Phe Arg Gly Glu Ile Lys Leu Gln Thr
    130                 135                 140

Ser Gln
145

<210> SEQ ID NO 33
<211> LENGTH: 154
<212> TYPE: PRT
<213> ORGANISM: Artificial
<220> FEATURE:
<223> OTHER INFORMATION: C2 domain of SHIP1

<400> SEQUENCE: 33

Thr Phe Glu Ala Gly Val Thr Ser Gln Phe Val Ser Lys Asn Gly Pro
1               5                   10                  15

Gly Thr Val Asp Ser Gln Gly Gln Ile Glu Phe Leu Arg Cys Tyr Ala
            20                  25                  30

Thr Leu Lys Thr Lys Ser Gln Thr Lys Phe Tyr Leu Glu Phe His Ser
        35                  40                  45

Ser Cys Leu Glu Ser Phe Val Lys Ser Gln Glu Gly Glu Asn Glu Glu
    50                  55                  60

Gly Ser Glu Gly Glu Leu Val Val Lys Phe Gly Glu Thr Leu Pro Lys
65                  70                  75                  80

Leu Lys Pro Ile Ile Ser Asp Pro Glu Tyr Leu Leu Asp Gln His Ile
                85                  90                  95

Leu Ile Ser Ile Lys Ser Ser Asp Ser Asp Glu Ser Tyr Gly Glu Gly
            100                 105                 110

Cys Ile Ala Leu Arg Leu Glu Ala Thr Glu Thr Gln Leu Pro Ile Tyr
        115                 120                 125

Thr Pro Leu Thr His His Gly Glu Leu Thr Gly His Phe Gln Gly Glu
    130                 135                 140

Ile Lys Leu Gln Thr Ser Gln Gly Lys Met
145                 150

<210> SEQ ID NO 34
<211> LENGTH: 168
<212> TYPE: PRT
<213> ORGANISM: Artificial
<220> FEATURE:
<223> OTHER INFORMATION: C2 domain of SHIP1

<400> SEQUENCE: 34

Thr Phe Glu Ala Gly Val Thr Ser Gln Phe Val Ser Lys Asn Gly Pro
1               5                   10                  15

Gly Thr Val Asp Ser Gln Gly Gln Ile Glu Phe Leu Arg Cys Tyr Ala
            20                  25                  30

Thr Leu Lys Thr Lys Ser Gln Thr Lys Phe Tyr Leu Glu Phe His Ser
        35                  40                  45

Ser Cys Leu Glu Ser Phe Val Lys Ser Gln Glu Gly Glu Asn Glu Glu
    50                  55                  60

Gly Ser Glu Gly Glu Leu Val Val Lys Phe Gly Glu Thr Leu Pro Lys
65                  70                  75                  80

Leu Lys Pro Ile Ile Ser Asp Pro Glu Tyr Leu Leu Asp Gln His Ile
                85                  90                  95

Leu Ile Ser Ile Lys Ser Ser Asp Ser Asp Glu Ser Tyr Gly Glu Gly
            100                 105                 110

```
Cys Ile Ala Leu Arg Leu Glu Ala Thr Glu Thr Gln Leu Pro Ile Tyr
            115                 120                 125

Thr Pro Leu Thr His His Gly Glu Leu Thr Gly His Phe Gln Gly Glu
        130                 135                 140

Ile Lys Leu Gln Thr Ser Gln Gly Lys Thr Arg Glu Lys Leu Tyr Asp
145                 150                 155                 160

Phe Val Lys Thr Glu Arg Asp Glu
                165

<210> SEQ ID NO 35
<211> LENGTH: 112
<212> TYPE: PRT
<213> ORGANISM: Artificial
<220> FEATURE:
<223> OTHER INFORMATION: PH domain of SHIP1

<400> SEQUENCE: 35

Ser Thr Asn Arg Arg Ser Leu Ile Pro Pro Val Thr Phe Glu Val Lys
1               5                   10                  15

Ser Glu Ser Leu Gly Ile Pro Gln Lys Met His Leu Lys Val Asp Val
            20                  25                  30

Glu Ser Gly Lys Leu Ile Val Lys Ser Lys Asp Gly Ser Glu Asp
        35                  40                  45

Lys Phe Tyr Ser His Lys Lys Ile Leu Gln Leu Ile Lys Ser Gln Lys
50                  55                  60

Phe Leu Asn Lys Leu Val Ile Leu Val Glu Thr Glu Lys Glu Lys Ile
65                  70                  75                  80

Leu Arg Lys Glu Tyr Val Phe Ala Asp Ser Lys Lys Arg Glu Gly Phe
                85                  90                  95

Cys Gln Leu Leu Gln Gln Met Lys Asn Lys His Ser Glu Gln Pro Glu
            100                 105                 110

<210> SEQ ID NO 36
<211> LENGTH: 112
<212> TYPE: PRT
<213> ORGANISM: Artificial
<220> FEATURE:
<223> OTHER INFORMATION: PH domain of SHIP1

<400> SEQUENCE: 36

Ser Pro His Arg Pro Ser Leu Ile Pro Pro Val Thr Phe Glu Val Lys
1               5                   10                  15

Ala Glu Ser Leu Gly Ile Pro Gln Lys Met Gln Leu Lys Val Asp Val
            20                  25                  30

Glu Ser Gly Lys Leu Ile Ile Lys Lys Ser Lys Asp Gly Ser Glu Asp
        35                  40                  45

Lys Phe Tyr Ser His Lys Lys Ile Leu Gln Leu Ile Lys Ser Gln Lys
50                  55                  60

Phe Leu Asn Lys Leu Val Ile Leu Val Glu Thr Glu Lys Glu Lys Ile
65                  70                  75                  80

Leu Arg Lys Glu Tyr Val Phe Ala Asp Ser Lys Lys Arg Glu Gly Phe
                85                  90                  95

Cys Gln Leu Leu Gln Gln Met Lys Asn Lys His Ser Glu Gln Pro Glu
            100                 105                 110

<210> SEQ ID NO 37
<211> LENGTH: 312
<212> TYPE: PRT
```

<213> ORGANISM: Artificial
<220> FEATURE:
<223> OTHER INFORMATION: SHIP phosphatase domain

<400> SEQUENCE: 37

```
Asp Met Ile Thr Ile Phe Ile Gly Thr Trp Asn Met Gly Asn Ala Pro
1               5                   10                  15
Pro Pro Lys Lys Ile Thr Ser Trp Phe Leu Ser Lys Gly Gln Gly Lys
            20                  25                  30
Thr Arg Asp Asp Ser Ala Asp Tyr Ile Pro His Asp Ile Tyr Val Ile
        35                  40                  45
Gly Thr Gln Glu Asp Pro Leu Ser Glu Lys Glu Trp Leu Glu Ile Leu
    50                  55                  60
Lys His Ser Leu Gln Glu Ile Thr Ser Val Thr Phe Lys Thr Val Ala
65                  70                  75                  80
Ile His Thr Leu Trp Asn Ile Arg Ile Val Val Leu Ala Lys Pro Glu
                85                  90                  95
His Glu Asn Arg Ile Ser His Ile Cys Thr Asp Asn Val Lys Thr Gly
            100                 105                 110
Ile Ala Asn Thr Leu Gly Asn Lys Gly Ala Val Gly Val Ser Phe Met
        115                 120                 125
Phe Asn Gly Thr Ser Leu Gly Phe Val Asn Ser His Leu Thr Ser Gly
    130                 135                 140
Ser Glu Lys Lys Leu Arg Arg Asn Gln Asn Tyr Met Asn Ile Leu Arg
145                 150                 155                 160
Phe Leu Ala Leu Gly Asp Lys Lys Leu Ser Pro Phe Asn Ile Thr His
                165                 170                 175
Arg Phe Thr His Leu Phe Trp Phe Gly Asp Leu Asn Tyr Arg Val Asp
            180                 185                 190
Leu Pro Thr Trp Glu Ala Glu Thr Ile Ile Gln Lys Ile Lys Gln Gln
        195                 200                 205
Gln Tyr Ala Asp Leu Leu Ser His Asp Gln Leu Leu Thr Glu Arg Arg
    210                 215                 220
Glu Gln Lys Val Phe Leu His Phe Glu Glu Glu Glu Ile Thr Phe Ala
225                 230                 235                 240
Pro Thr Tyr Arg Phe Glu Arg Leu Thr Arg Asp Lys Tyr Ala Tyr Thr
                245                 250                 255
Lys Gln Lys Ala Thr Gly Met Lys Tyr Asn Leu Pro Ser Trp Cys Asp
            260                 265                 270
Arg Val Leu Trp Lys Ser Tyr Pro Leu Val His Val Val Cys Gln Ser
        275                 280                 285
Tyr Gly Ser Thr Ser Asp Ile Met Thr Ser Asp His Ser Pro Val Phe
    290                 295                 300
Ala Thr Phe Glu Ala Gly Val Thr
305                 310
```

<210> SEQ ID NO 38
<211> LENGTH: 21
<212> TYPE: DNA
<213> ORGANISM: Artificial
<220> FEATURE:
<223> OTHER INFORMATION: SHIP1 Delta C2 Upstream Fragment Sense Primer

<400> SEQUENCE: 38
ttcatgttca ttggaacctc c          21

```
<210> SEQ ID NO 39
<211> LENGTH: 32
<212> TYPE: DNA
<213> ORGANISM: Artificial
<220> FEATURE:
<223> OTHER INFORMATION: SHIP1 Delta C2 Upstream Fragment Anti-Sense
      Primer

<400> SEQUENCE: 39
tttgcggccg caccattctt ggagacgaat tg                                32

<210> SEQ ID NO 40
<211> LENGTH: 32
<212> TYPE: DNA
<213> ORGANISM: Artificial
<220> FEATURE:
<223> OTHER INFORMATION: SHIP1 Delta C2 Downstream Fragment Sense
      Primer

<400> SEQUENCE: 40
ttgcggccgc tagggagaag ctctatgact tt                                32

<210> SEQ ID NO 41
<211> LENGTH: 32
<212> TYPE: DNA
<213> ORGANISM: Artificial
<220> FEATURE:
<223> OTHER INFORMATION: SHIP1 Delta C2 Downstream Fragment Anti-Sense
      Primer

<400> SEQUENCE: 41
tttctagatt acatggcagt cctgccaagc ag                                32

<210> SEQ ID NO 42
<211> LENGTH: 33
<212> TYPE: DNA
<213> ORGANISM: Artificial
<220> FEATURE:
<223> OTHER INFORMATION: C2 Domain Sense Primer

<400> SEQUENCE: 42
aaatttcata tgcctggcac tgtagatagc caa                               33

<210> SEQ ID NO 43
<211> LENGTH: 33
<212> TYPE: DNA
<213> ORGANISM: Artificial
<220> FEATURE:
<223> OTHER INFORMATION: C2 Domain Anti-Sense Primer

<400> SEQUENCE: 43
tatgaattct tacatcttgc cctgggaggt ctg                               33

<210> SEQ ID NO 44
<211> LENGTH: 21
<212> TYPE: DNA
<213> ORGANISM: Artificial
<220> FEATURE:
<223> OTHER INFORMATION: SHIP1 (delta) PH Upstream Fragment Sense Primer

<400> SEQUENCE: 44
gtagaaagtg tcatgtcacc a                                            21

<210> SEQ ID NO 45
<211> LENGTH: 32
<212> TYPE: DNA
<213> ORGANISM: Artificial
```

```
<220> FEATURE:
<223> OTHER INFORMATION: SHIP1 (delta) PH Upstream Fragment Anti-Sense
      Primer

<400> SEQUENCE: 45
ttagcggccg cttctgagcc ctcgtgcagc aa                                       32

<210> SEQ ID NO 46
<211> LENGTH: 32
<212> TYPE: DNA
<213> ORGANISM: Artificial
<220> FEATURE:
<223> OTHER INFORMATION: SHIP1 (delta) PH Downstream Fragment Sense
      Primer

<400> SEQUENCE: 46
ttgcggccgc tcctgacatg atcaccatct tc                                       32

<210> SEQ ID NO 47
<211> LENGTH: 21
<212> TYPE: DNA
<213> ORGANISM: Artificial
<220> FEATURE:
<223> OTHER INFORMATION: SHIP1 (delta) PH Downstream Fragment Anti-Sense
      Primer

<400> SEQUENCE: 47
tgcatacttg tcccgggtca g                                                   21

<210> SEQ ID NO 48
<211> LENGTH: 33
<212> TYPE: DNA
<213> ORGANISM: Artificial
<220> FEATURE:
<223> OTHER INFORMATION: PH Domain Sense Primer

<400> SEQUENCE: 48
aaatttcata tgtctaccaa caggcgttcc ctt                                      33

<210> SEQ ID NO 49
<211> LENGTH: 33
<212> TYPE: DNA
<213> ORGANISM: Artificial
<220> FEATURE:
<223> OTHER INFORMATION: PH Domain Anti-Sense Primer

<400> SEQUENCE: 49
tatgaattct tactctggct gctccgaatg ctt                                      33

<210> SEQ ID NO 50
<211> LENGTH: 1258
<212> TYPE: PRT
<213> ORGANISM: Homo sapiens

<400> SEQUENCE: 50

Met Ala Ser Ala Cys Gly Ala Pro Gly Pro Gly Gly Ala Leu Gly Ser
1               5                   10                  15

Gln Ala Pro Ser Trp Tyr His Arg Asp Leu Ser Arg Ala Ala Ala Glu
            20                  25                  30

Glu Leu Leu Ala Arg Ala Gly Arg Asp Gly Ser Phe Leu Val Arg Asp
        35                  40                  45

Ser Glu Ser Val Ala Gly Ala Phe Ala Leu Cys Val Leu Tyr Gln Lys
    50                  55                  60

His Val His Thr Tyr Arg Ile Leu Pro Asp Gly Glu Asp Phe Leu Ala
```

-continued

```
              65                  70                  75                  80
Val Gln Thr Ser Gln Gly Val Pro Val Arg Arg Phe Gln Thr Leu Gly
                      85                  90                  95
Glu Leu Ile Gly Leu Tyr Ala Gln Pro Asn Gln Gly Leu Val Cys Ala
                100                 105                 110
Leu Leu Leu Pro Val Glu Gly Glu Arg Glu Pro Asp Pro Pro Asp Asp
            115                 120                 125
Arg Asp Ala Ser Asp Gly Glu Asp Glu Lys Pro Pro Leu Pro Pro Arg
        130                 135                 140
Ser Gly Ser Thr Ser Ile Ser Ala Pro Thr Gly Pro Ser Ser Pro Leu
145                 150                 155                 160
Pro Ala Pro Glu Thr Pro Thr Ala Pro Ala Glu Ser Ala Pro Asn
                165                 170                 175
Gly Leu Ser Thr Val Ser His Asp Tyr Leu Lys Gly Ser Tyr Gly Leu
                180                 185                 190
Asp Leu Glu Ala Val Arg Gly Gly Ala Ser His Leu Pro His Leu Thr
            195                 200                 205
Arg Thr Leu Ala Thr Ser Cys Arg Arg Leu His Ser Glu Val Asp Lys
        210                 215                 220
Val Leu Ser Gly Leu Glu Ile Leu Ser Lys Val Phe Asp Gln Gln Ser
225                 230                 235                 240
Ser Pro Met Val Thr Arg Leu Leu Gln Gln Asn Leu Pro Gln Thr
                245                 250                 255
Gly Glu Gln Glu Leu Glu Ser Leu Val Leu Lys Leu Ser Val Leu Lys
                260                 265                 270
Asp Phe Leu Ser Gly Ile Gln Lys Lys Ala Leu Lys Ala Leu Gln Asp
            275                 280                 285
Met Ser Ser Thr Ala Pro Pro Ala Pro Gln Pro Ser Thr Arg Lys Ala
        290                 295                 300
Lys Thr Ile Pro Val Gln Ala Phe Glu Val Lys Leu Asp Val Thr Leu
305                 310                 315                 320
Gly Asp Leu Thr Lys Ile Gly Lys Ser Gln Lys Phe Thr Leu Ser Val
                325                 330                 335
Asp Val Glu Gly Gly Arg Leu Val Leu Leu Arg Arg Gln Arg Asp Ser
                340                 345                 350
Gln Glu Asp Trp Thr Thr Phe Thr His Asp Arg Ile Arg Gln Leu Ile
            355                 360                 365
Lys Ser Gln Arg Val Gln Asn Lys Leu Gly Val Val Phe Glu Lys Glu
        370                 375                 380
Lys Asp Arg Thr Gln Arg Lys Asp Phe Ile Phe Val Ser Ala Arg Lys
385                 390                 395                 400
Arg Glu Ala Phe Cys Gln Leu Leu Gln Leu Met Lys Asn Lys His Ser
                405                 410                 415
Lys Gln Asp Glu Pro Asp Met Ile Ser Val Phe Ile Gly Thr Trp Asn
                420                 425                 430
Met Gly Ser Val Pro Pro Pro Lys Asn Val Thr Ser Trp Phe Thr Ser
            435                 440                 445
Lys Gly Leu Gly Lys Thr Leu Asp Glu Val Thr Val Thr Ile Pro His
        450                 455                 460
Asp Ile Tyr Val Phe Gly Thr Gln Glu Asn Ser Val Gly Asp Arg Glu
465                 470                 475                 480
Trp Leu Asp Leu Leu Arg Gly Gly Leu Lys Glu Leu Thr Asp Leu Asp
                485                 490                 495
```

```
Tyr Arg Pro Ile Ala Met Gln Ser Leu Trp Asn Ile Lys Val Ala Val
            500                 505                 510

Leu Val Lys Pro Glu His Glu Asn Arg Ile Ser His Val Ser Thr Ser
        515                 520                 525

Ser Val Lys Thr Gly Ile Ala Asn Thr Leu Gly Asn Lys Gly Ala Val
    530                 535                 540

Gly Val Ser Phe Met Phe Asn Gly Thr Ser Phe Gly Phe Val Asn Cys
545                 550                 555                 560

His Leu Thr Ser Gly Asn Glu Lys Thr Ala Arg Arg Asn Gln Asn Tyr
                565                 570                 575

Leu Asp Ile Leu Arg Leu Leu Ser Leu Gly Asp Arg Gln Leu Asn Ala
            580                 585                 590

Phe Asp Ile Ser Leu Arg Phe Thr His Leu Phe Trp Phe Gly Asp Leu
        595                 600                 605

Asn Tyr Arg Leu Asp Met Asp Ile Gln Glu Ile Leu Asn Tyr Ile Ser
    610                 615                 620

Arg Lys Glu Phe Glu Pro Leu Leu Arg Val Asp Gln Leu Asn Leu Glu
625                 630                 635                 640

Arg Glu Lys His Lys Val Phe Leu Arg Phe Ser Glu Glu Ile Ser
                645                 650                 655

Phe Pro Pro Thr Tyr Arg Tyr Glu Arg Gly Ser Arg Asp Thr Tyr Ala
            660                 665                 670

Trp His Lys Gln Lys Pro Thr Gly Val Arg Thr Asn Val Pro Ser Trp
        675                 680                 685

Cys Asp Arg Ile Leu Trp Lys Ser Tyr Pro Glu Thr His Ile Ile Cys
    690                 695                 700

Asn Ser Tyr Gly Cys Thr Asp Asp Ile Val Thr Ser Asp His Ser Pro
705                 710                 715                 720

Val Phe Gly Thr Phe Glu Val Gly Val Thr Ser Gln Phe Ile Ser Lys
                725                 730                 735

Lys Gly Leu Ser Lys Thr Ser Asp Gln Ala Tyr Ile Glu Phe Glu Ser
            740                 745                 750

Ile Glu Ala Ile Val Lys Thr Ala Ser Arg Thr Lys Phe Phe Ile Glu
        755                 760                 765

Phe Tyr Ser Thr Cys Leu Glu Glu Tyr Lys Lys Ser Phe Glu Asn Asp
    770                 775                 780

Ala Gln Ser Ser Asp Asn Ile Asn Phe Leu Lys Val Gln Trp Ser Ser
785                 790                 795                 800

Arg Gln Leu Pro Thr Leu Lys Pro Ile Leu Ala Asp Ile Glu Tyr Leu
                805                 810                 815

Gln Asp Gln His Leu Leu Leu Thr Val Lys Ser Met Asp Gly Tyr Glu
            820                 825                 830

Ser Tyr Gly Glu Cys Val Val Ala Leu Lys Ser Met Ile Gly Ser Thr
        835                 840                 845

Ala Gln Gln Phe Leu Thr Phe Leu Ser His Arg Gly Glu Glu Thr Gly
    850                 855                 860

Asn Ile Arg Gly Ser Met Lys Val Arg Val Pro Thr Glu Arg Leu Gly
865                 870                 875                 880

Thr Arg Glu Arg Leu Tyr Glu Trp Ile Ser Ile Asp Lys Asp Glu Ala
                885                 890                 895

Gly Ala Lys Ser Lys Ala Pro Ser Val Ser Arg Gly Ser Gln Glu Pro
            900                 905                 910
```

Arg Ser Gly Ser Arg Lys Pro Ala Phe Thr Glu Ala Ser Cys Pro Leu
             915                 920                 925

Ser Arg Leu Phe Glu Glu Pro Glu Lys Pro Pro Thr Gly Arg Pro
    930                 935                 940

Pro Ala Pro Pro Arg Ala Ala Pro Arg Glu Glu Pro Leu Thr Pro Arg
945                 950                 955                 960

Leu Lys Pro Glu Gly Ala Pro Glu Pro Glu Gly Val Ala Ala Pro Pro
                965                 970                 975

Pro Lys Asn Ser Phe Asn Pro Ala Tyr Tyr Val Leu Glu Gly Val
            980                 985                 990

Pro His Gln Leu Leu Pro Glu Pro Pro Ser Pro Ala Arg Ala Pro
        995                 1000                1005

Val Pro Ser Ala Thr Lys Asn Lys Val Ala Ile Thr Val Pro Ala
    1010                1015                1020

Pro Gln Leu Gly His His Arg His Pro Arg Val Gly Glu Gly Ser
    1025                1030                1035

Ser Ser Asp Glu Glu Ser Gly Gly Thr Leu Pro Pro Pro Asp Phe
    1040                1045                1050

Pro Pro Pro Pro Leu Pro Asp Ser Ala Ile Phe Leu Pro Pro Ser
    1055                1060                1065

Leu Asp Pro Leu Pro Gly Pro Val Val Arg Gly Arg Gly Gly Ala
    1070                1075                1080

Glu Ala Arg Gly Pro Pro Pro Lys Ala His Pro Arg Pro Pro
    1085                1090                1095

Leu Pro Pro Gly Pro Ser Pro Ala Ser Thr Phe Leu Gly Glu Val
    1100                1105                1110

Gly Ser Gly Asp Asp Arg Ser Cys Ser Val Leu Gln Met Ala Lys
    1115                1120                1125

Thr Leu Ser Glu Val Asp Tyr Ala Pro Ala Gly Pro Ala Arg Ser
    1130                1135                1140

Ala Leu Leu Pro Gly Pro Leu Glu Leu Gln Pro Pro Arg Gly Leu
    1145                1150                1155

Pro Ser Asp Tyr Gly Arg Pro Leu Ser Phe Pro Pro Pro Arg Ile
    1160                1165                1170

Arg Glu Ser Ile Gln Glu Asp Leu Ala Glu Ala Pro Cys Leu
    1175                1180                1185

Gln Gly Gly Arg Ala Ser Gly Leu Gly Glu Ala Gly Met Ser Ala
    1190                1195                1200

Trp Leu Arg Ala Ile Gly Leu Glu Arg Tyr Glu Glu Gly Leu Val
    1205                1210                1215

His Asn Gly Trp Asp Asp Leu Glu Phe Leu Ser Asp Ile Thr Glu
    1220                1225                1230

Glu Asp Leu Glu Glu Ala Gly Val Gln Asp Pro Ala His Lys Arg
    1235                1240                1245

Leu Leu Leu Asp Thr Leu Gln Leu Ser Lys
    1250                1255

<210> SEQ ID NO 51
<211> LENGTH: 928
<212> TYPE: PRT
<213> ORGANISM: Mus musculus

<400> SEQUENCE: 51

Met Val Ala Lys Leu Ser Gln Leu Thr Ser Leu Leu Ser Ser Ile Glu
1               5                   10                  15

```
Asp Lys Val Lys Ser Leu Leu His Glu Gly Ser Glu Ser Thr Asn Arg
            20                  25                  30

Arg Ser Leu Ile Pro Pro Val Thr Phe Glu Val Lys Ser Glu Ser Leu
        35                  40                  45

Gly Ile Pro Gln Lys Met His Leu Lys Val Asp Val Glu Ser Gly Lys
50                  55                  60

Leu Ile Val Lys Ser Lys Asp Gly Ser Glu Asp Lys Phe Tyr Ser
65                  70                  75                  80

His Lys Lys Ile Leu Gln Leu Ile Lys Ser Gln Lys Phe Leu Asn Lys
                    85                  90                  95

Leu Val Ile Leu Val Glu Thr Glu Lys Glu Lys Ile Leu Arg Lys Glu
                100                 105                 110

Tyr Val Phe Ala Asp Ser Lys Lys Arg Glu Gly Phe Cys Gln Leu Leu
            115                 120                 125

Gln Gln Met Lys Asn Lys His Ser Glu Gln Pro Glu Pro Asp Met Ile
130                 135                 140

Thr Ile Phe Ile Gly Thr Trp Asn Met Gly Asn Ala Pro Pro Pro Lys
145                 150                 155                 160

Lys Ile Thr Ser Trp Phe Leu Ser Lys Gly Gln Gly Lys Thr Arg Asp
                165                 170                 175

Asp Ser Ala Asp Tyr Ile Pro His Asp Ile Tyr Val Ile Gly Thr Gln
            180                 185                 190

Glu Asp Pro Leu Gly Glu Lys Glu Trp Leu Glu Leu Leu Arg His Ser
        195                 200                 205

Leu Gln Glu Val Thr Ser Met Thr Phe Lys Thr Val Ala Ile His Thr
    210                 215                 220

Leu Trp Asn Ile Arg Ile Val Val Leu Ala Lys Pro Glu His Glu Asn
225                 230                 235                 240

Arg Ile Ser His Ile Cys Thr Asp Asn Val Lys Thr Gly Ile Ala Asn
                245                 250                 255

Thr Leu Gly Asn Lys Gly Ala Val Gly Val Ser Phe Met Phe Asn Gly
            260                 265                 270

Thr Ser Leu Gly Phe Val Asn Ser His Leu Thr Ser Gly Ser Glu Lys
        275                 280                 285

Lys Leu Arg Arg Asn Gln Asn Tyr Met Asn Ile Leu Arg Phe Leu Ala
    290                 295                 300

Leu Gly Asp Lys Lys Leu Ser Pro Phe Asn Ile Thr His Arg Phe Thr
305                 310                 315                 320

His Leu Phe Trp Leu Gly Asp Leu Asn Tyr Arg Val Glu Leu Pro Thr
                325                 330                 335

Trp Glu Ala Glu Ala Ile Ile Gln Lys Ile Lys Gln Gln Gln Tyr Ser
            340                 345                 350

Asp Leu Leu Ala His Asp Gln Leu Leu Leu Glu Arg Lys Asp Gln Lys
        355                 360                 365

Val Phe Leu His Phe Glu Glu Glu Ile Thr Phe Ala Pro Thr Tyr
    370                 375                 380

Arg Phe Glu Arg Leu Thr Arg Asp Lys Tyr Ala Tyr Thr Lys Gln Lys
385                 390                 395                 400

Ala Thr Gly Met Lys Tyr Asn Leu Pro Ser Trp Cys Asp Arg Val Leu
                405                 410                 415

Trp Lys Ser Tyr Pro Leu Val His Val Val Cys Gln Ser Tyr Gly Ser
            420                 425                 430
```

```
Thr Ser Asp Ile Met Thr Ser Asp His Ser Pro Val Phe Ala Thr Phe
            435                 440                 445

Glu Ala Gly Val Thr Ser Gln Phe Val Ser Lys Asn Gly Pro Gly Thr
        450                 455                 460

Val Asp Ser Gln Gly Gln Ile Glu Phe Leu Ala Cys Tyr Ala Thr Leu
465                 470                 475                 480

Lys Thr Lys Ser Gln Thr Lys Phe Tyr Leu Glu Phe His Ser Ser Cys
                485                 490                 495

Leu Glu Ser Phe Val Lys Ser Gln Glu Gly Asn Glu Glu Gly Ser
            500                 505                 510

Glu Gly Glu Leu Val Val Arg Phe Gly Glu Thr Leu Pro Lys Leu Lys
            515                 520                 525

Pro Ile Ile Ser Asp Pro Glu Tyr Leu Leu Asp Gln His Ile Leu Ile
        530                 535                 540

Ser Ile Lys Ser Ser Asp Ser Asp Glu Ser Tyr Gly Glu Gly Cys Ile
545                 550                 555                 560

Ala Leu Arg Leu Glu Thr Thr Glu Ala Gln His Pro Ile Tyr Thr Pro
                565                 570                 575

Leu Thr His His Gly Glu Met Thr Gly His Phe Arg Gly Glu Ile Lys
            580                 585                 590

Leu Gln Thr Ser Gln Gly Lys Met Arg Glu Lys Leu Tyr Asp Phe Val
        595                 600                 605

Lys Thr Glu Arg Asp Glu Ser Ser Gly Met Lys Cys Leu Lys Asn Leu
        610                 615                 620

Thr Ser His Asp Pro Met Arg Gln Trp Glu Pro Ser Gly Arg Val Pro
625                 630                 635                 640

Ala Cys Gly Val Ser Ser Leu Asn Glu Met Ile Asn Pro Asn Tyr Ile
                645                 650                 655

Gly Met Gly Pro Phe Gly Gln Pro Leu His Gly Lys Ser Thr Leu Ser
            660                 665                 670

Pro Asp Gln Gln Leu Thr Ala Trp Ser Tyr Asp Gln Leu Pro Lys Asp
        675                 680                 685

Ser Ser Leu Gly Pro Gly Arg Gly Glu Gly Pro Thr Pro Pro Ser
690                 695                 700

Gln Pro Pro Leu Ser Pro Lys Lys Phe Ser Ser Thr Ala Asn Arg
705                 710                 715                 720

Gly Pro Cys Pro Arg Val Gln Glu Ala Arg Pro Gly Asp Leu Gly Lys
                725                 730                 735

Val Glu Ala Leu Leu Gln Glu Asp Leu Leu Thr Lys Pro Glu Met
            740                 745                 750

Phe Glu Asn Pro Leu Tyr Gly Ser Val Ser Ser Phe Pro Lys Leu Val
            755                 760                 765

Pro Arg Lys Glu Gln Glu Ser Pro Lys Met Leu Arg Lys Glu Pro Pro
        770                 775                 780

Pro Cys Pro Asp Pro Gly Ile Ser Ser Pro Ser Ile Val Leu Pro Lys
785                 790                 795                 800

Ala Gln Glu Val Glu Ser Val Lys Gly Thr Ser Lys Gln Ala Pro Val
                805                 810                 815

Pro Val Leu Gly Pro Thr Pro Arg Ile Arg Ser Phe Thr Cys Ser Ser
            820                 825                 830

Ser Ala Glu Gly Arg Met Thr Ser Gly Asp Lys Ser Gln Gly Lys Pro
            835                 840                 845

Lys Ala Ser Ala Ser Ser Gln Ala Pro Val Pro Val Lys Arg Pro Val
```

-continued

```
            850                 855                 860
Lys Pro Ser Arg Ser Glu Met Ser Gln Gln Thr Thr Pro Ile Pro Ala
865                     870                 875                 880

Pro Arg Pro Pro Leu Pro Val Lys Ser Pro Ala Val Leu Gln Leu Gln
                885                 890                 895

His Ser Lys Gly Arg Asp Tyr Arg Asp Asn Thr Glu Leu Pro His His
            900                 905                 910

Gly Lys His Arg Gln Glu Glu Gly Leu Leu Gly Arg Thr Ala Met Gln
            915                 920                 925
```